United States Patent
Posner et al.

(10) Patent No.: US 9,487,538 B2
(45) Date of Patent: Nov. 8, 2016

(54) TWO-CARBON LINKED ARTEMISININ-DERIVED TRIOXANE DIMERS

(71) Applicant: THE JOHNS HOPKINS UNIVERSITY, Baltimore, MD (US)

(72) Inventors: Gary H. Posner, Baltimore, MD (US); Bryan T. Mott, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/761,699

(22) PCT Filed: Jan. 22, 2014

(86) PCT No.: PCT/US2014/012452
§ 371 (c)(1),
(2) Date: Jul. 17, 2015

(87) PCT Pub. No.: WO2014/116642
PCT Pub. Date: Jul. 31, 2014

(65) Prior Publication Data
US 2015/0361088 A1    Dec. 17, 2015

Related U.S. Application Data

(60) Provisional application No. 61/755,199, filed on Jan. 22, 2013.

(51) Int. Cl.
A61K 31/352    (2006.01)
C07D 493/18    (2006.01)
(Continued)

(52) U.S. Cl.
CPC ........... *C07D 493/18* (2013.01); *A61K 31/357* (2013.01); *A61K 31/4433* (2013.01);
(Continued)

(58) Field of Classification Search
CPC ............. A61K 31/352; A61K 31/357; C07D 321/02; C07D 321/06; C07D 493/18; C07D 519/00
USPC ............... 514/86, 100, 263.31, 450; 549/348
See application file for complete search history.

(56) References Cited

U.S. PATENT DOCUMENTS 5,677,468 A    10/1997   Zheng et al.
6,586,464 B2   7/2003    Posner et al.
(Continued)

FOREIGN PATENT DOCUMENTS

WO    9933461 A1    7/1999
WO    0042046 A1    7/2000
(Continued)

OTHER PUBLICATIONS

International Search Report and Written Opinion dated May 5, 2014 from PCT International Application No. PCT/US14/12452.
(Continued)

*Primary Examiner* — Kamal Saeed
*Assistant Examiner* — Janet L Coppins
(74) *Attorney, Agent, or Firm* — Ward and Smith, P.A.

(57) ABSTRACT

Two-carbon linked artemisinin-derived trioxane dimers and methods of their use for treating subjects infected with malaria or other parasitic infectious diseases including, but not limited to, toxoplasmic infection; subjects afflicted with psychiatric conditions associated with toxoplasmic infection; and subjects afflicted with cancer.

14 Claims, 7 Drawing Sheets

(51) Int. Cl.
| | |
|---|---|
| A61K 31/357 | (2006.01) |
| A61K 31/4433 | (2006.01) |
| A61K 31/683 | (2006.01) |
| A61K 45/06 | (2006.01) |
| C07F 9/655 | (2006.01) |
| C07D 321/02 | (2006.01) |
| C07D 519/00 | (2006.01) |

(52) U.S. Cl.
CPC ............ *A61K31/683* (2013.01); *A61K 45/06* (2013.01); *C07F 9/65527* (2013.01); *C07D 321/02* (2013.01); *C07D 519/00* (2013.01)

(56) References Cited

U.S. PATENT DOCUMENTS

| | | | |
|---|---|---|---|
| 7,098,242 B2 | 8/2006 | Elsohly et al. | |
| 7,417,156 B2 | 8/2008 | Posner et al. | |
| 8,884,032 B2* | 11/2014 | Posner ................. | C07D 493/18 549/348 |

FOREIGN PATENT DOCUMENTS

| | | |
|---|---|---|
| WO | 2004028476 A2 | 4/2004 |
| WO | 2011071981 A2 | 6/2011 |

OTHER PUBLICATIONS

Mott et al. 'Synthesis and Antimalarial Efficacy of Two-Carbon Linked, Artemisinin-Derived,Trioxane Dimers in Combination with Known Antimalarial Drugs', J. Med. Chem. Mar. 28, 2013, 1-16 vol. 56(6), pp. 2630-2641.
W.H.O. Malaria fact sheet No. 94. http://www.who.int/mediacentre/factsheets/ fs094/en/index.html (accessed Aug. 13, 2012).
Frey, C.; Traore, C.; De Allegri, M.; Kouyate, B.; Muller, 0., Compliance of young children with ITN protection in rural Burkina Faso. Malaria J. 2006, 5 (70).
The RTS, S.; Clincal; Trials; Partnership, First Results of Phase 3 Trial of RTS,S/ASOI Malaria Vaccine in African Children. N Engl J Med 2011, 365 (20), 1863-1875.
Schlitzer, M., Malaria chemotherapeutics. Part I: History of antimalarial drug development, currently used therapeutics, and drugs in clinical development. Chem. Med. Chem. 2007, 2, 944-986.
Miller, L. H.; Su, X.-z., Artemisinin: Discovery from the Chinese Herbal Garde. Cell 2011, 146, 855-858.
He, R.; Mott, B. T.; Rosenthal, A. S.; Genna, D. T.; Posner, G. H.; Arav- Boger, R., An Artemisinin-Derived Dimer Has Highly Potent Anti-Cytomegalovirus (CMV) and Anti-Cancer Activities. PLoS One 2011, 6 (8), e24334.
Kyle, D. E.; Teja-Isavadharm, P.; Li, Q.; Leo, K., Pharmacokinetics and pharmacodynamics of qinghaosu derivatives: how do they impact on the choice of drug and the dosage regimens? Med. Trap. 1998, 58, 38-44.
Karplus, M., Contact Electron-Spin Coupling of Nuclear Magnetic Moments. J. Chem. Phys. 1959, 30, 11-15.
Haynes, R. K. et al. Artemisone—a highly active antimalarial drug of the artemisinin class. Angew. Chem. Int. Ed. 2006, 45, 2082-2088.
Araujo, N. C. P. et al. Semi-synthetic and synthetic 1,2,4-trioxaquines and 1,2,4-trioxolaquines: synthesis, preliminary SAR and comparison with acridine endoperoxide conjugates. Bioorg. Med. Chem. Lett. 2009, 19, 2038-2043.
Pacorel, B.; Leung, S. C.; Stachulski, A. V.; Davies, J.; Vivas, L.; Lander, H.; Ward, S. A.; Kaiser, M.; Brun, R.; O'Neill, P. M., Modular Synthesis and in Vitro and in Vivo Antimalarial Assessment of C-10 Pyrrole Mannich Base Derivatives of Artemisinin. J. Med. Chem. 2010, 53, 633-640.
Chadwick, J.; Jones, M.; Mercer, A. E.; Stocks, P.A.; Ward, S. A.; Park, B. K.; O'Neill, P. M., Design, synthesis and antimalarial/anticancer evaluation of spermidine linked artemisinin conjugates designed to exploit polyamine transporters in Plasmodium falciparum and HL-60 cancer cell lines. Bioorg. Med. Chem. 2010, 18, 2586-2597.
Begue, J.P.; Bonnet-Delpon, D., Fluoroartemisinins: metabolically more stable antimalarial artemisinin derivatives. Chem. Med. Chem. 2007, 2, 608-624.
Singh, C.; Hassam, M.; Verma, V. P.; Singh, A. S.; Naikade, N. K.; Puri, S. K.; Maulik, P.R.; Kant, R., Bile Acid-Based 1,2,4-Trioxanes: Synthesis and Antimalarial Assessment. J. Med. Chem. 2012, 55, 10662-10673.
Dong, Y. et al. Spiro and Dispiro-1,2,4-trioxolanes as Antimalarial Peroxides: Charting a Workable Structure Activity Relationship Using Simple Prototypes. J. Med. Chem. 2005, 48, 4953-4961.
Charman, S. A., et al. Synthetic ozonide drug candidate OZ439 offers new hope for a single-dose cure of uncomplicated malaria. Proc. Nat. Acad. Sci. 2011, 108, 4400-4405.
Slack, R. D.; Jacobine, A. M.; Posner, G. H., Antimalarial peroxides: advances in drug discovery and design. Med. Chem. Commun. 2012, 3 (281-297).
Moon, D. K.; Tripathi, A.; Sullivan, D.; Siegler, M.A.; Parkin, S.; Posner, G. H., A single, low, oral dose of a 5-carbon-linked trioxane dimer orthoester plus mefloquine cures malaria-infected mice. Bioorg. Med. Chem. Lett. 2011, 21, 2773-2775.
Paik, I.-H.; Xie, S.; Shapiro, T. A.; Labonte, T.; Narducci-Sarjeant, A. A.; Baege, A. C.; Posner, G. H., Second Generation, Orally Active, Antimalarial, Artemisinin-Derived Trioxane Dimers with High Stability, Efficacy, and Anticancer 10 Activity. J. Med. Chem. 2006, 49, 2731-2734.
Rosenthal, A. S.; Chen, X.; Liu, J. O.; West, D. C.; Hergenrother, P. J.; Shapiro, T. A.; Posner, G. H., Malaria-Infected Mice Are Cured by a Single Oral Dose of New Dimeric Trioxane Sulfones Which Are Also Selectively and Powerfully Cytotoxic to Cancer Cells. J. Med. Chem. 2009, 52, 1198-1203.
Woodard, L. E.; Chang, W.; Chen, X.; Liu, J. O.; Shapiro, T. A.; Posner, G. H., Malaria-Infected Mice Live until at Least Day 30 after a New Monomeric Trioxane Combined with Mefloquine Are Administered Together in a Single Low Oral Dose. J. Med. Chem. 2009, 52, 7458-7462.
Svennas, K.L., MacDonald, S.J. F., Willis 2012 Small molecule anti-malarial patents: a review. Expert Opinion on Therapeutic. 22(6), p. 607-643.
Galal, A. M.; Ahmad, M. S.; El-Feraly, F. S.; McPhail, A. T., Preparation and Characterization of a New Artemisinin-Derived Dimer. J. Nat. Prod. 1996, 59, 917-920.
Pu, Y. M.; Ziffer, H., Synthesis and Antimalarial Activities of 12.beta.-Allyldeoxoartemisinin and Its Derivatives. J. Med. Chem. 1995, 38, 613-616.
Jung, M.; Lee, K.; Kendrick, H.; Robinson, B. L.; Croft, S. L., Synthesis, Stability, and Antimalarial Activity of New Hydrolytically Stable and Water-Soluble(+)-Deoxoartelinic Acid. J. Med. Chem. 2002, 45, 4940-4944.
Posner, G. H.; Ploypradith, P.; Parker, M. H.; O'Dowd, H.; Woo, S.-H.; Northrop, J.; Krasavin, M.; Dolan, P.; Kensler, T. W.; Xie, S.; Shapiro, T. A.Antimalarial, Antiproliferative, and Antitumor Activities of Artemisinin-Derived, Chemically Robust, Trioxane Dimers. J. Med. Chem. 1999, 42, 4275-4280.
Hevia, E.; Chua, J. Z.; Garcia-Alvarez, P.; Kennedy, A. R.; McCall, M. D, Exposing the hidden complexity of stoichiometric and catalytic metathesis reactions by elucidation of Mg—Zn hybrids. Proc. Nat. Acad. Sci. 2010, 107, 5294-5299.
Hatano, M.; Suzuki, S.; Ishihara, K., Highly Chemoselective Stoichiometric Alkylation of Ketones with Grignard Reagent Derived Zinc(II) Ate Complexes. Synlett 2010, 2, 321-324.
Lepore, S. D.; Mondal, D., Recent advances in heterolytic nucleofugal leaving groups. Tetrahedron 2007, 63, 5103-5122.
Krivogorksy, B.; Grundt, P.; Yolken, R.; Jones-Brando, L., Inhibition of Toxoplasma gondii by Indirubin and Tryptanthrin Analogs. Antimicrob. Agents Chemother. 2008, 52, 4466-4469.
M.M.V. Pyramax® (pyronaridine-artesunate). http://www.mmv.org/researchdevelopment/project-portfolio/pyramax%C2%AE-pyronaridine-artesunate (accessed 30 Sep. 6, 2012).

(56) References Cited

OTHER PUBLICATIONS

Ma, J.; Katz, E.; Kyle, D. E.; Ziffer, H., Syntheses and Antimalarial Activities of 10-Substituted Deoxoartemisinins. J. Med. Chem. 2000, 43, 4228-4232.

Corey, E. J.; Bakshi, R. K.; Shibata, S., Highly Enantioselective Borane Reduction of Ketones Catalyzed by Chiral Oxazaborolidines. Mechanism and Synthetic Implications. J. Am. Chem. Soc. 1987, 109, 5551-5553.

Musilek, K.; Dolezal, M.; Gunn-Moore, F.; Kuca, K., Design, evaluation and structure-activity relationship studies of the AChE reactivators against organophosphorus pesticides. Med. Res. Rev. 2009, 31, 548-575.

Gibson, C. L.; Huggan, J. K.; Kennedy, A.; Kiefer, L.; Lee, J. H.; Suckling, C. J.; Clements, C.; Harvey, A. L.; Hunter, W. N.; Tulloch, L.B., Diversity oriented syntheses of fused pyrimidines designed as potential antifolates. Org. Biomol. Chem. 2009, 7, 1829-1842.

Huttunen, K. M.; Kumpulainen, H.; Leppanen, J.; Rautio, J.; Jarvinen, T.; Vepsalainen, J., Efficient strategy to prepare water-soluble prodrugs of ketones. Synlett 2006, 5, 701-704.

Venhuis, B. J.; Dijkstra, D.; Wustrow, D.; Meltzer, L. T.; Wise, L. D.; Johnson, S. J.; Wikstrom, H. V., Orally Active Oxime Derivatives of the Dopaminergic Prodrug 6-(N,N-Di-n-propyl-amino )-3,4,5,6, 7,8-hexahydro-2H-naphthalen-1-one. Synthesis and Pharmacological Activity. J. Med. Chem. 2003, 46,4136-4140.

Kumpulainen, H.; Mahonen, N.; Laitinen, M.-L.; Jaurakkajarvi, M.; Raunio, H.; Juvonen, R. O.; Vepsalainen, J.; Jarvinen, T.; Rautio, J., Evaluation of Hydroxyimine as Cytochrome P450-Selective Prodrug Structure. J. Med. Chem. 2006, 49, 1207-1211.

Prokai, L.; Wu, W.-M.; Somogyi, G.; Bodor, N., Ocular Delivery of the~Adrenergic Antagonist Alprenolol by Sequential Bioactivation of Its Methoxime Analogue. J. Med. Chem. 1995, 38, 2018-2020.

Haynes, R. K.; Chan, H.-W.; Cheung, M.-K.; Lam, W.-L.; Soo, M.-K.; Tsang, H.-W.; Voerste, A.; Williams, I. D., C-10 Ester and Ether Derivatives of Dihydroartemisinin—10-a Artesunate, Preparation of Authentic 10-a Artesunate, and of Other Ester and Ether Derivatives Bearing Potential Aromatic Intercalating Groups at C-10. Eur. J. Org. Chem. 2002, 2002, 113-132.

\* cited by examiner

TWO-CARBON LINKED ARTEMISININ-DERIVED TRIOXANE DIMERS

CROSS REFERENCE TO RELATED APPLICATIONS

This application is a 35 U.S.C. §371 National Stage Entry of International Application No. PCT/US2014/012452 having an international filing date of Jan. 22, 2014, which claims the benefit of U.S. Provisional Application No. 61/755,199, filed Jan. 22, 2013, the content of each of the aforementioned applications is herein incorporated by reference in its entirety.

FEDERALLY SPONSORED RESEARCH OR DEVELOPMENT

This invention was made with government support under AI 34885 awarded by the National Institutes of Health. The government has certain rights in the invention.

BACKGROUND

As the landscape of therapeutic treatment advances, orally available small molecule inhibitors remain a prominent weapon in the fight against disease. Perhaps nowhere is this approach more important than in the treatment of malaria, whose parasites infected over 200 million people and killed approximately 655,000 people in 2010. W.H.O., 2012. Prevention of malaria caused by the *Plasmodium* parasites has centered on the use of bed netting (which suffers from poor compliance), Frey, et al., 2006, and attempts to develop a vaccine (which has recently seen a breakthrough, albeit marginal), see The RTS, S., 2011, but the large number of people who still become infected continues to keep small molecule therapeutic treatment of paramount importance.

The history of malaria therapy is long and dozens of small molecules have been the treatment of choice at some point. Schlitzer, 2007. Well known examples include quinine, chloroquine, and atovaquone (compounds 1-3, respectively, FIG. 1). Each of these molecules (and others) has fallen from prominence, due either to significant side effects or to the development of parasite resistance, or both. Schlitzer, 2007. These chemical entities have been largely replaced by treatments containing the natural product artemisinin.

Artemisinin (4a, FIG. 2) could be considered one of the most significant natural product small molecule discoveries over the past 40 years. The molecule was first isolated from its natural source, *Artemisia annua*, in 1972 by a team under the direction of Dr. Youyou Tu. Miller and Su, 2011. It contains a surprisingly stable endoperoxide linkage that is essential for the demonstrated activity in a variety of diseases, most notably malaria and, more recently, several types of cancers and cytomegalovirus. He, et al., 2011. Unfortunately the molecule has poor bioavailability and is rapidly cleared from the body. Kyle, et al., 1998. First generation derivatives that attempt to circumvent this issue include lipid-soluble artemether (4b) and water-soluble artesunate (4c), and these molecules are now part of the first line of antimalarial treatment known as artemisinin combination therapy (ACT). Example combinations are Coartem® (artemether 4b plus lumefantrine 5, FIG. 3), Artequin® (artesunate 4c plus mefloquine 6, FIG. 3) and the recently FDA-approved Pyramax® (artesunate 4c plus pyronaridine 7, FIG. 3). Both artemether and artesunate, however, still have significant metabolic liabilities and short half-lives, so most new candidate drug combinations pair an artemisinin-derived analog with a drug that has better physical properties and a longer duration of activity. Further structure-activity relationships (SAR) have been explored around this peroxide linkage and have ranged from functionalization of the natural product, Haynes, et al., 2006; Araujo, N. C. P., et al., 2009; Pacorel, B., et al., 2010; Chadwick, et al., 2010; and Begue and Bonnet-Delpon, 2007; to completely synthetic peroxide structures. Singh, et al., 2012.; Dong, et al., 2005; Charman, et al., 2011; and Slack, R. D. et al., 2012. The pursuit of highly efficacious artemisinin derivatives and novel drug combinations continues.

SUMMARY

The presently disclosed subject matter provides two-carbon linked artemisinin-derived trioxane dimers and methods of their use for treating subjects infected with malaria or other parasitic infectious diseases including, but not limited to, toxoplasmic infection; subjects afflicted with psychiatric conditions associated with toxoplasmic infection; and subjects afflicted with cancer.

In some aspects, a compound of Formula (I) is provided:

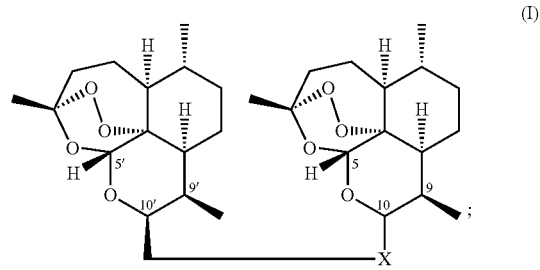

wherein:

X is selected from the group consisting of $C(=O)$; $C=NR_1$; $C=NOR_2$; $C=NNHR_3$; and $CH-O-R_4$;

$R_1$ is selected from the group consisting of substituted or unsubstituted linear or branched alkyl, substituted or unsubstituted cycloalkyl, substituted or unsubstituted cycloheteroalkyl, substituted or unsubstituted aryl, and substituted or unsubstituted heteroaryl;

$R_2$ is selected from the group consisting of H, substituted or unsubstituted linear or branched alkyl, substituted or unsubstituted alkenyl, substituted or unsubstituted alkynyl, $-P(=O)(OR_5)(OR_5)$, wherein each $R_5$ is independently lower linear or branched alkyl, aryl or heteroaryl, and $-C(=O)R_6$, wherein $R_6$ is substituted or unsubstituted linear or branched alkyl, substituted or unsubstituted cycloalkyl, alkoxyl, aryloxyl, substituted or unsubstituted cycloheteroalkyl, substituted or unsubstituted aryl, substituted or unsubstituted heteroaryl, and $NR_7R_8$, wherein $R_7$ and $R_8$ are each independently selected from the group consisting of H, substituted or unsubstituted linear or branched alkyl, substituted or unsubstituted cycloalkyl, substituted or unsubstituted cycloheteroalkyl, substituted or unsubstituted aryl, substituted or unsubstituted heteroaryl;

$R_3$ is selected from the group consisting of substituted or unsubstituted linear or branched alkyl, substituted or unsubstituted cycloalkyl, substituted or unsubstituted cycloheteroalkyl, substituted or unsubstituted aryl, substituted or unsubstituted heteroaryl, and $-C(=O)R_9$, wherein $R_9$ is selected from the group consisting of substituted or unsubstituted linear or branched alkyl, substituted or unsubstituted cycloalkyl, substituted or unsubstituted cycloheteroalkyl, substituted or unsubstituted aryl, substituted or unsubstituted heteroaryl;

$R_4$ is selected from the group consisting of H, substituted or unsubstituted linear or branched alkyl, substituted or unsubstituted alkenyl, substituted or unsubstituted alkynyl, substituted or unsubstituted aryl, substituted or unsubstituted heteroaryl, —P(=O)(OR$_5$)(OR$_5$), wherein each $R_5$ is independently lower linear or branched alkyl, aryl or heteroaryl, and —C(=O)R$_{10}$, wherein $R_{10}$ is substituted or unsubstituted linear or branched alkyl, substituted or unsubstituted cycloalkyl, alkoxyl, aryloxyl, substituted or unsubstituted cycloheteroalkyl, substituted or unsubstituted aryl, substituted or unsubstituted heteroaryl, and NR$_{11}$R$_{12}$, wherein R$_{11}$ and R$_{12}$ are each independently selected from the group consisting of H, substituted or unsubstituted linear or branched alkyl, substituted or unsubstituted cycloalkyl, substituted or unsubstituted cycloheteroalkyl, substituted or unsubstituted aryl, substituted or unsubstituted heteroaryl;

or an enantiomer, diastereomer, racemate or pharmaceutically acceptable salt, prodrug, or solvate thereof.

In certain aspects, the presently disclosed compounds of Formula (I) can be used for preventing, controlling or treating an infectious disease in a subject in need of treatment thereof.

In particular aspects, the infectious disease includes a parasitic disease selected from the group consisting of a plasmodia parasite infection, a *T. gondii* infection, a trypanosome parasite infection, and a *Cryptosporidium* parasite infection.

In other aspects, the method of treatment further comprises administering to the subject a quinoline anti-malarial drug including, but not limited to, chloroquine, quinine, mefloquine, and primaquine, and/or an antifolate and/or a second anti-malarial drug, such as, lumefantrine, concurrently or sequentially with a compound of Formula (I).

In other aspects, the presently disclosed subject matter provides a method of treating a psychiatric disorder associated with toxoplasma infection, such as schizophrenia, in a subject in need of treatment thereof, the method comprising administering to the subject a therapeutically-effective amount of a compound of Formula (I).

In yet other aspects, the method further comprises administering to the subject one or more antipsychotic drugs selected from the group consisting of chlorpromazine (THORAZINE®), haloperidol (HALDOL®), fluphenazine (PROLIXIN®), thiothixene (NA VANE®), trifluoperazine (STELAZINE®), perphenazine (TRILAFON®), and thioridazine (MELLARIL®), clozapine (CLOZARIL®), risperidone (RISPERDAL®), olanzapine (ZYPREXA®), quetiapine (SEROQUEL®), ziprasidone (GEODON®), and aripiprazole (ABILIFY®) concurrently or sequentially with the compound of Formula (I).

In further aspects, the presently disclosed subject matter provides a method for treating cancer, including, but not limited to, leukemia, non-small cell lung cancer, colon cancer, central nervous system cancer, melanoma cancer, ovarian cancer, renal cancer, prostate cancer, and breast cancer, in a subject in need of treatment thereof, the method comprising administering to the subject a therapeutically-effective amount of a compound of Formula (I).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
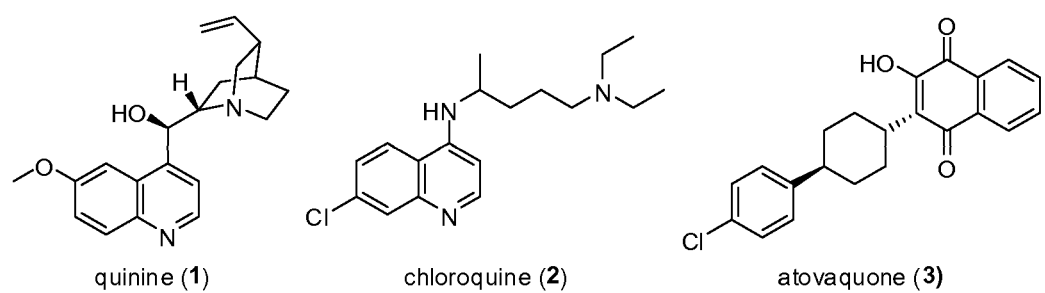
Figure 2:
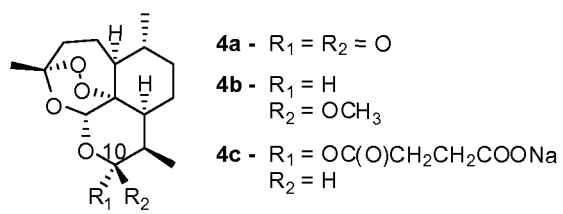
Figure 3:
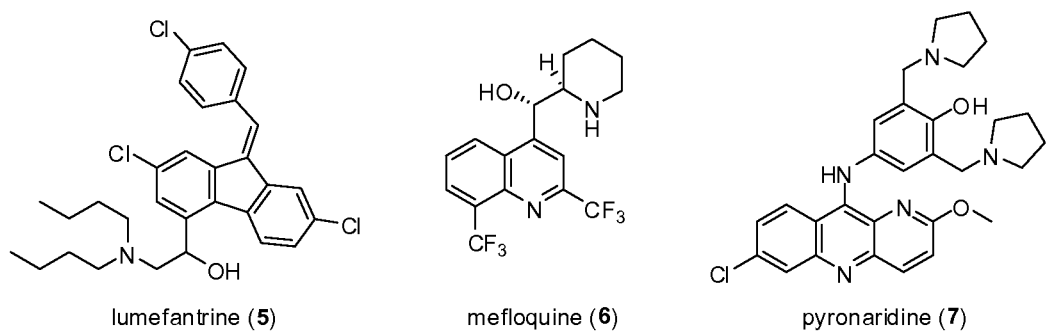
Figure 4:
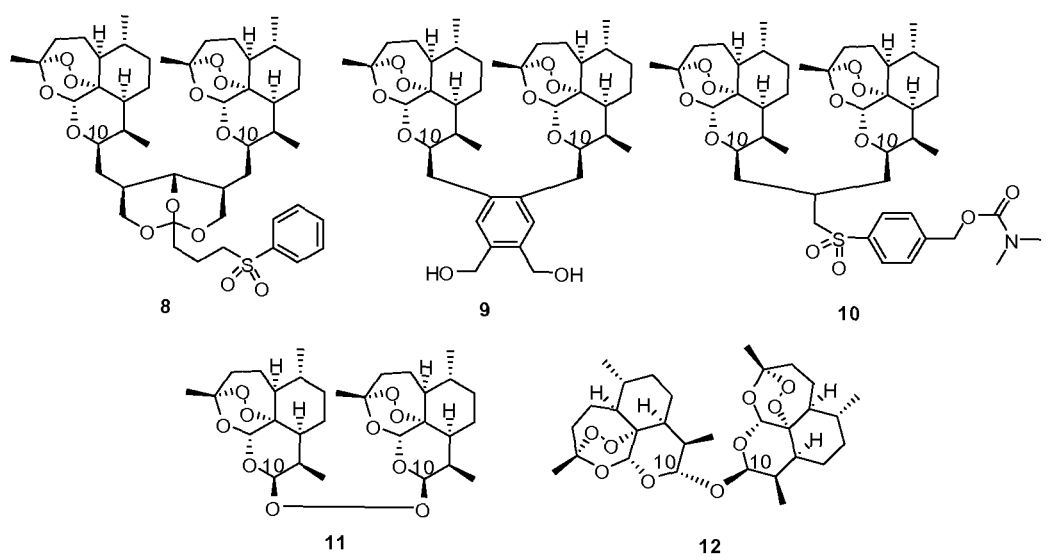
Figure 5:
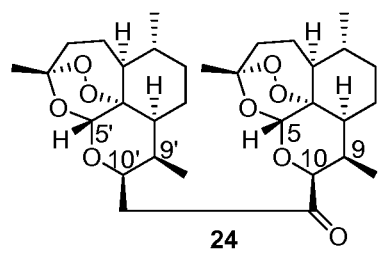
Figure 6:
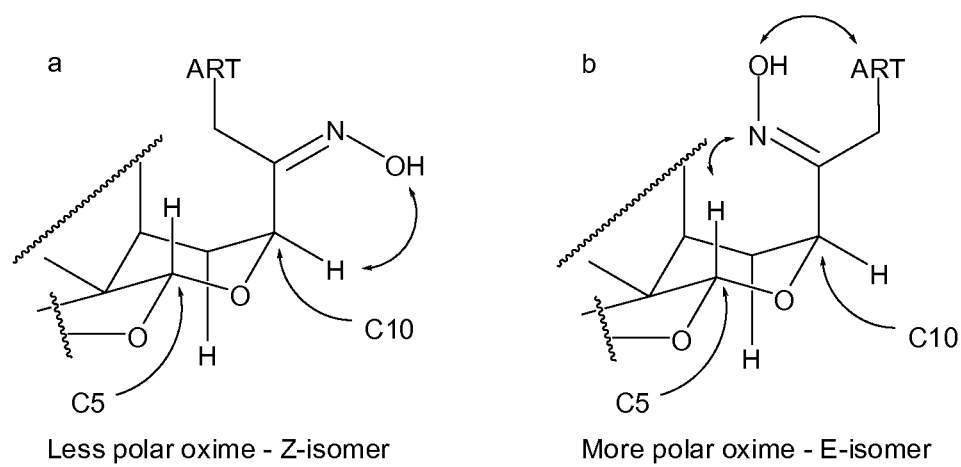
Figure 7:
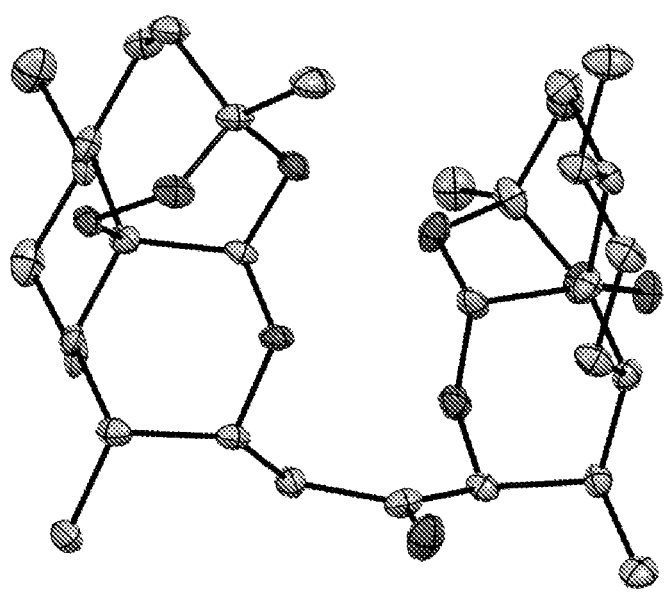

Having thus described the presently disclosed subject matter in general terms, reference will now be made to the accompanying Figures, which are not necessarily drawn to scale, and wherein:

FIG. 1 shows the chemical structures of representative antimalarial agents to which resistance has developed (Prior Art);

FIG. 2 shows the chemical structures of artemisinin and currently-used first generation derivatives (Prior Art);

FIG. 3 shows the chemical structures of currently-used therapeutic drugs in artemisinin combination therapy (ACT) (Prior Art);

FIG. 4 shows the chemical structures of representative presently disclosed artemisinin dimers of varying linker length (Prior Art);

FIG. 5 shows a representative carbon numbering scheme for proton NMR analysis;

FIGS. 6a and 6b show (a) proposed interactions in the less polar dimer oxime Z-28; and (b) proposed interactions in the more polar dimer oxime E-28; and FIG. 7 shows the crystal structure of dimer ketone 24.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

As provided in more detail immediately herein below, the presently disclosed subject matter provides two-carbon linked artemisinin-derived trioxane dimers and methods of their use for treating subjects infected with malaria or other parasitic infectious diseases including, but not limited to, toxoplasmic infection; subjects afflicted with psychiatric conditions associated with toxoplasmic infection; and subjects afflicted with cancer.

I. Synthesis and Antimalarial Activity of Two-Carbon Linked Artemisinin-Derived Trioxane Dimers in Combination with Known Antimalarial Drugs Malaria continues to be a difficult disease to eradicate, largely due to the widespread populations it affects and to the resistance it has developed against once very potent therapies. The natural product artemisinin has been a boon for antimalarial chemotherapy as artemisinin combination therapy (ACT) has become the first line of chemotherapy. Because the threat of resistance is always on the horizon, it is imperative to continually identify new treatments, including advanced analogs of all antimalarial drugs, especially artemisinin, as well as the exploration of novel combinations, ideally with distinct mechanisms of action. In some embodiments, the presently disclosed matter provides the synthesis of a series of two-carbon linked artemisinin-derived dimers, their unique structural features, and demonstration of their antimalarial efficacy in vivo. In further embodiments, the presently disclosed endoperoxide chemical entities consistently demonstrate excellent antimalarial efficacy. Combinations therapy including the presently disclosed two-carbon linked artemisinin-derived trioxane dimers in combination with non-peroxide antimalarial drugs also is disclosed.

A. SYNTHETIC ARTEMISININ-DERIVED DIMERS

Efforts to improve the pharmacokinetic properties of artemisinin are ongoing. A wide variety of functional groups have been incorporated to improve absorption and increase the half-life of the molecule in vivo while also maintaining efficacy. Slack, et al., 2012. An alternative approach has been to synthetically tether two artemisinin units together to form dimeric molecules, the rationale being that, at a minimum, for every molecule that survives the metabolism and excretion processes, two of the required endoperoxide pharmacophores will be delivered to the sight of action. Dimer molecules, however, are often more than simply twice as potent as the corresponding monomers, and therefore an as yet unknown explanation must exist.

Many examples of artemisinin dimers having varying lengths of the linker between the two units exist, usually tethering at the C10 position (position numbered in FIG. 2). The most successful examples include linker lengths of 5, Moon, et al., 2011; 4, Paik, et al., 2006; or 3, Rosenthal, et al., 2009, and Woodard, et al., 2009; carbon atoms (example structures 8, 9, and 10, respectively, FIG. 4). Only one example of a two-atom linked dimer (the peroxide linked dimer molecule 11), Posner, et al., 2000, and only one example of a single-atom linked dimer (the ether linked dimer molecule 12) are thought to exist. Galal, et al., 1996. In some embodiments, the presently disclosed subject matter provides the synthesis of a series of novel two-carbon linked dimers, their absolute stereochemical configuration, and their antimalarial efficacies. Further, several of the presently disclosed dimers have been screened in combination with two adjuvants to establish a diverse set of potential drug combinations.

Accordingly, in some embodiments, the presently disclosed subject matter provides a compound of Formula (I):

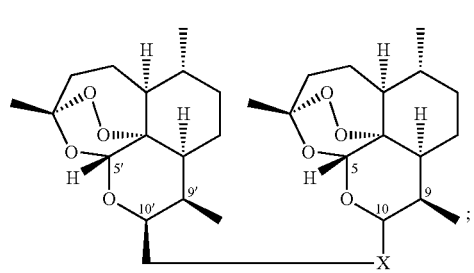

(I)

wherein:
X is selected from the group consisting of C(=O); C=NR$_1$; C=NOR$_2$; C=NNHR$_3$; and CH—O—R$_4$;
R$_1$ is selected from the group consisting of substituted or unsubstituted linear or branched alkyl, substituted or unsubstituted cycloalkyl, substituted or unsubstituted cycloheteroalkyl, substituted or unsubstituted aryl, and substituted or unsubstituted heteroaryl;

R$_2$ is selected from the group consisting of H, substituted or unsubstituted linear or branched alkyl, substituted or unsubstituted alkenyl, substituted or unsubstituted alkynyl, —P(=O)(OR$_5$)(OR$_5$), wherein each R$_5$ is independently lower linear or branched alkyl, aryl or heteroaryl, and —C(=O)R$_6$, wherein R$_6$ is substituted or unsubstituted linear or branched alkyl, substituted or unsubstituted cycloalkyl, alkoxyl, aryloxyl, substituted or unsubstituted cycloheteroalkyl, substituted or unsubstituted aryl, substituted or unsubstituted heteroaryl, and NR$_7$R$_8$, wherein R$_7$ and R$_8$ are each independently selected from the group consisting of H, substituted or unsubstituted linear or branched alkyl, substituted or unsubstituted cycloalkyl, substituted or unsubstituted cycloheteroalkyl, substituted or unsubstituted aryl, substituted or unsubstituted heteroaryl;

R$_3$ is selected from the group consisting of substituted or unsubstituted linear or branched alkyl, substituted or unsubstituted cycloalkyl, substituted or unsubstituted cycloheteroalkyl, substituted or unsubstituted aryl, substituted or unsubstituted heteroaryl, and —(C=O)R$_9$, wherein R$_9$ is selected from the group consisting of substituted or unsubstituted linear or branched alkyl, substituted or unsubstituted cycloalkyl, substituted or unsubstituted cycloheteroalkyl, substituted or unsubstituted aryl, substituted or unsubstituted heteroaryl;

R$_4$ is selected from the group consisting of H, substituted or unsubstituted linear or branched alkyl, substituted or unsubstituted alkenyl, substituted or unsubstituted alkynyl, substituted or unsubstituted aryl, substituted or unsubstituted heteroaryl, —P(=O)(OR$_5$)(OR$_5$), wherein each R$_5$ is independently lower linear or branched alkyl, aryl or heteroaryl, and —C(=O)R$_{10}$, wherein R$_{10}$ is substituted or unsubstituted linear or branched alkyl, substituted or unsubstituted cycloalkyl, alkoxyl, aryloxyl, substituted or unsubstituted cycloheteroalkyl, substituted or unsubstituted aryl, substituted or unsubstituted heteroaryl, and NR$_{11}$R$_{12}$, wherein R$_{11}$ and R$_{12}$ are each independently selected from the group consisting of H, substituted or unsubstituted linear or branched alkyl, substituted or unsubstituted cycloalkyl, substituted or unsubstituted cycloheteroalkyl, substituted or unsubstituted aryl, substituted or unsubstituted heteroaryl; or an enantiomer, diastereomer, racemate or pharmaceutically acceptable salt, prodrug, or solvate thereof.

In some embodiments, X is C(=O) and the compound of Formula (I) is:

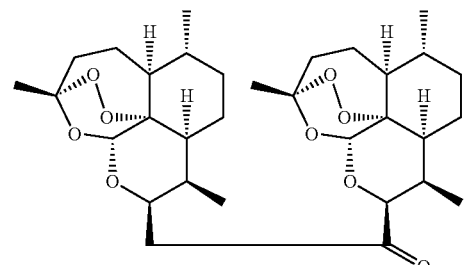

24

In other embodiments, X is C=NR$_1$ and the compound of Formula (I) is selected from the group consisting of:

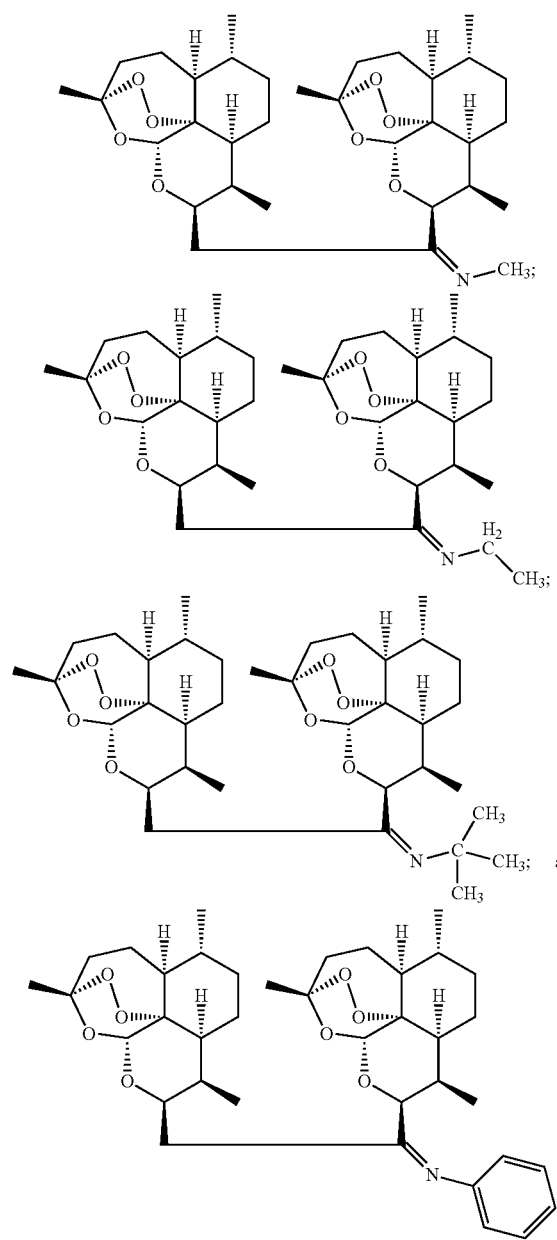
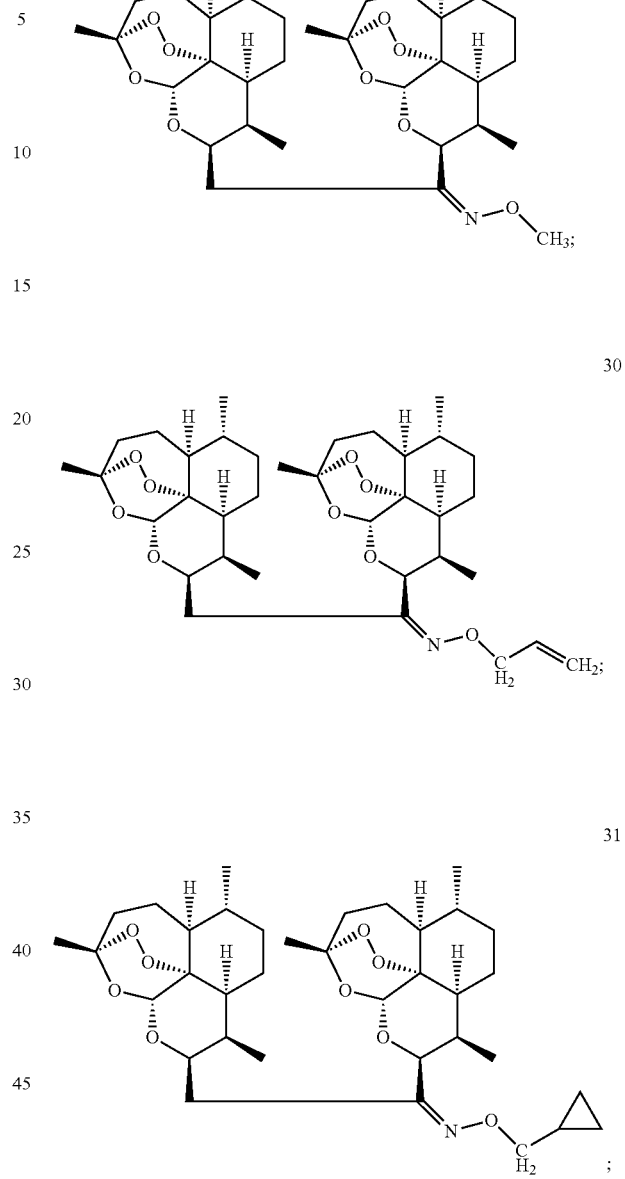
In yet other embodiments, X is C=NOR$_2$ and the compound of Formula (I) is selected from the group consisting of:
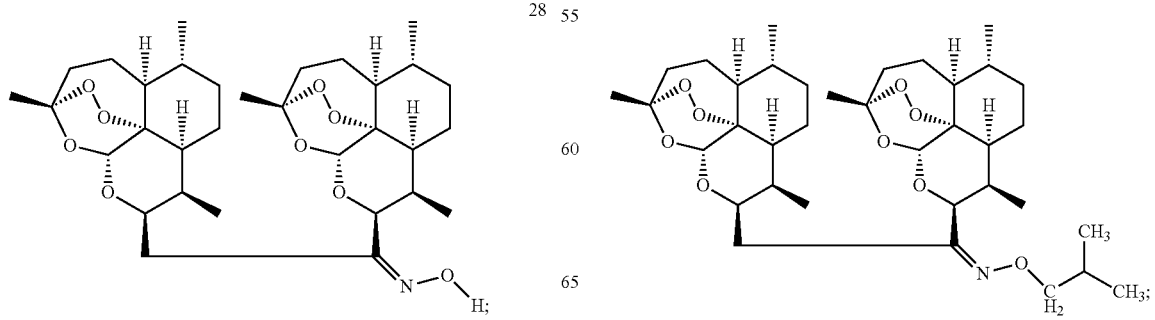

33
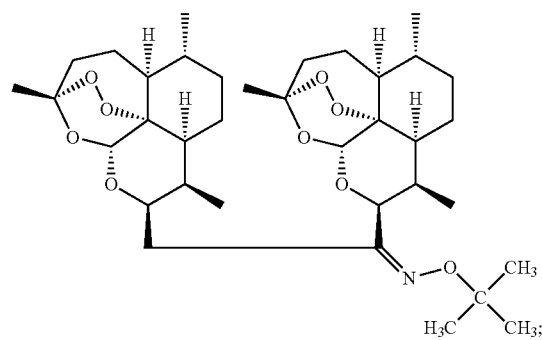
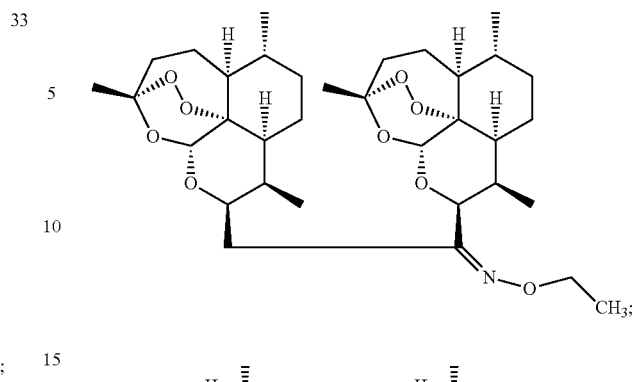
34
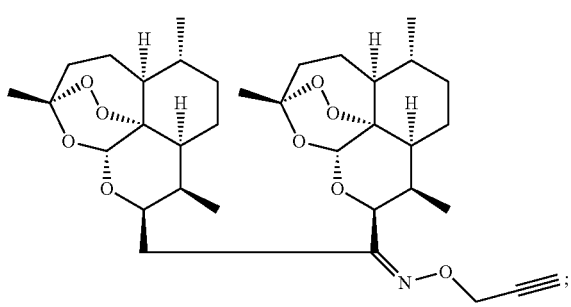
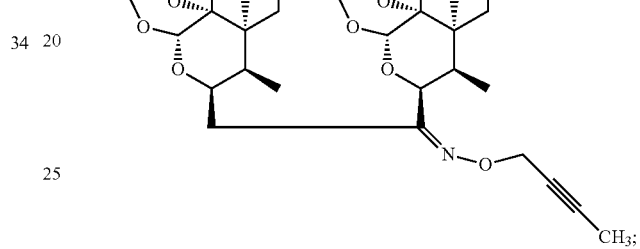
35
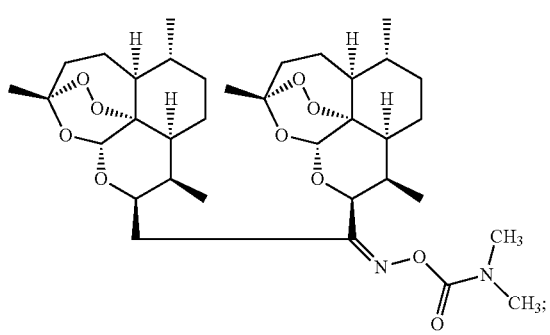
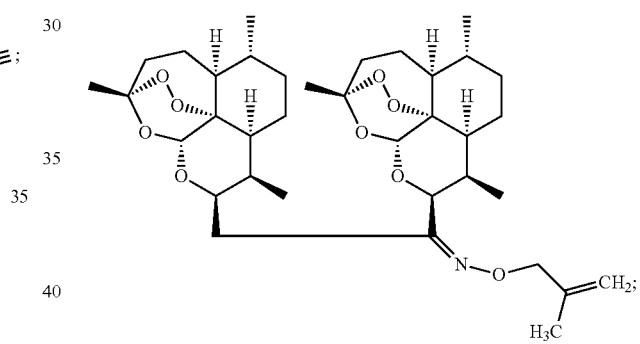
36
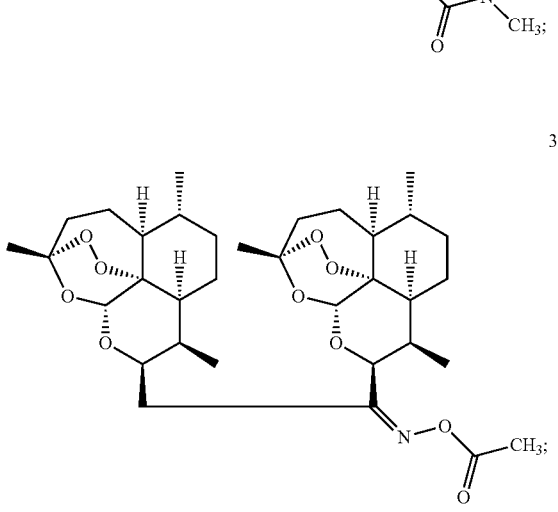
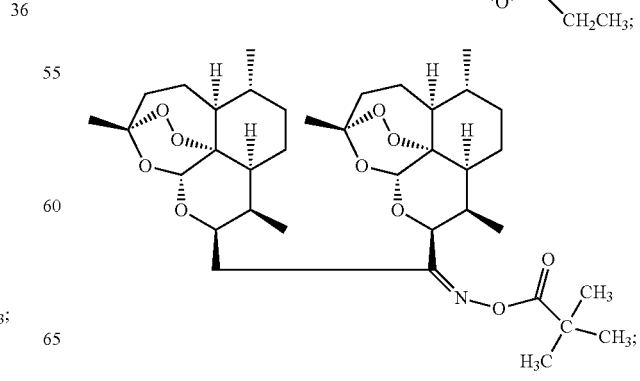

-continued
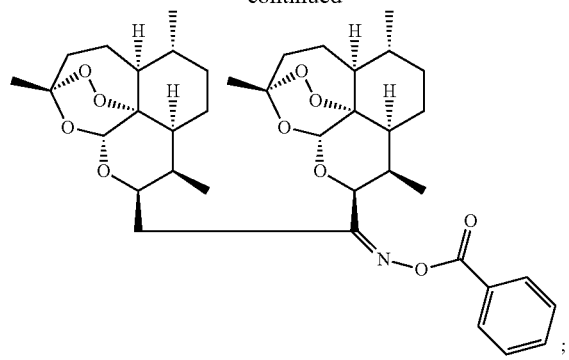
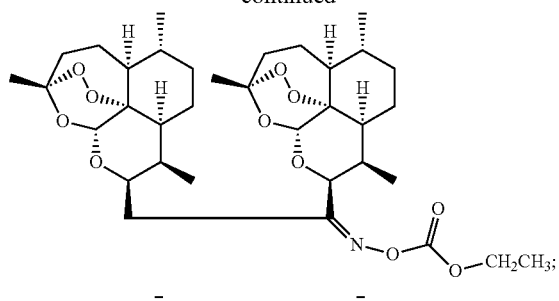
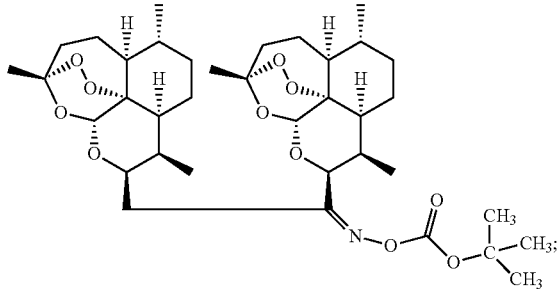
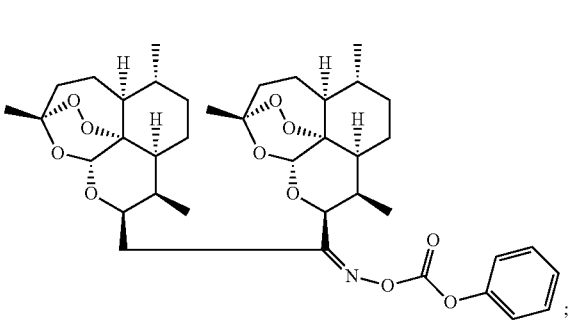
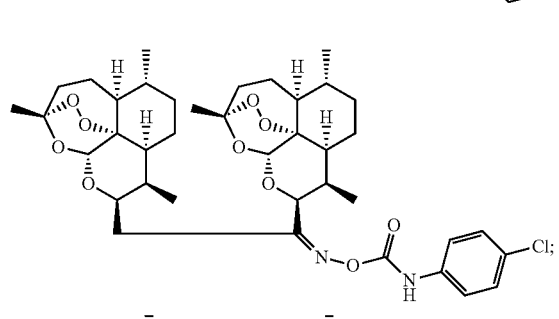
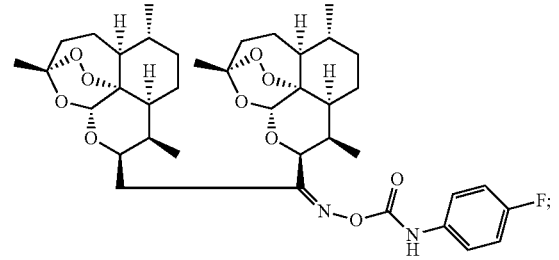
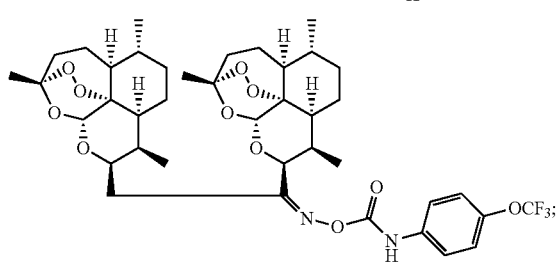

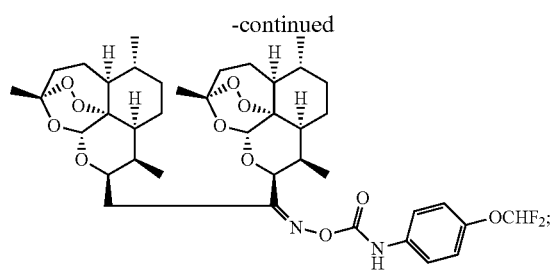
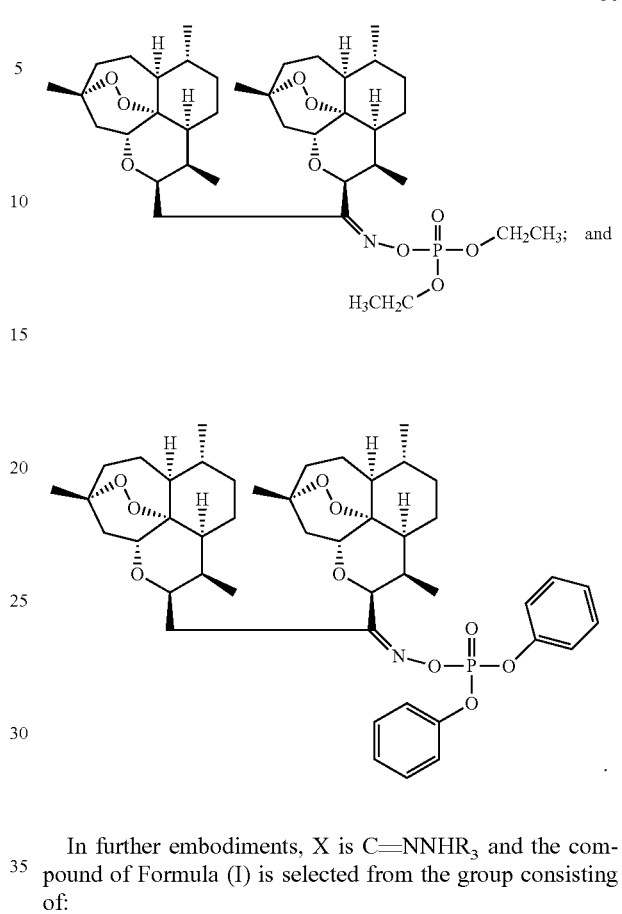
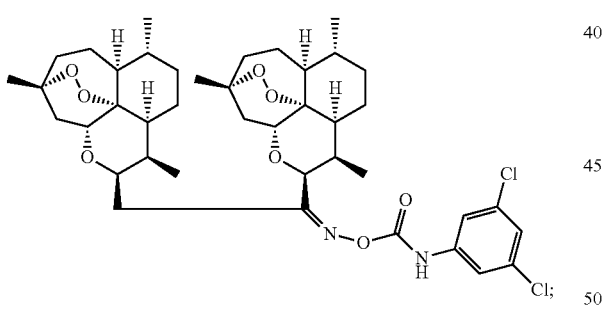
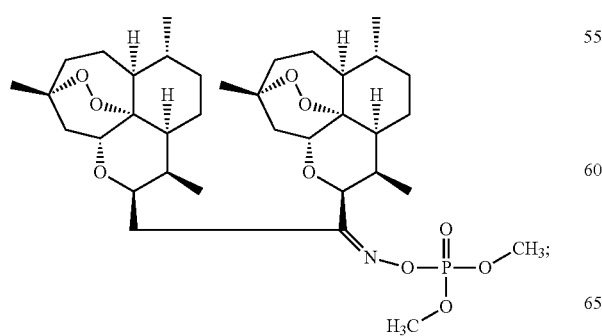
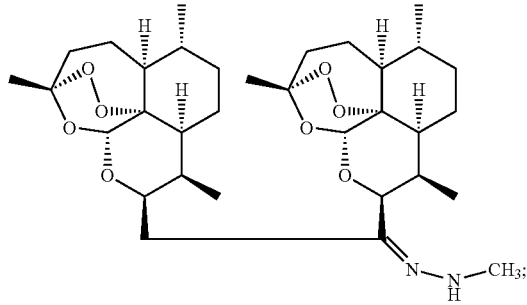
In further embodiments, X is C=NNHR₃ and the compound of Formula (I) is selected from the group consisting of:
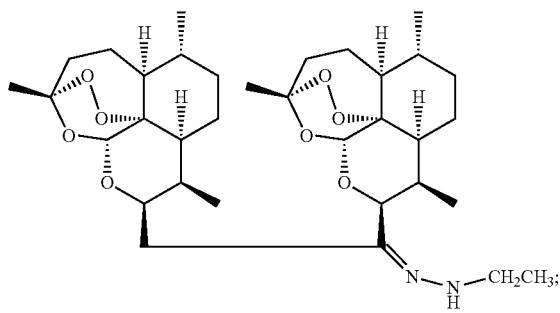

-continued
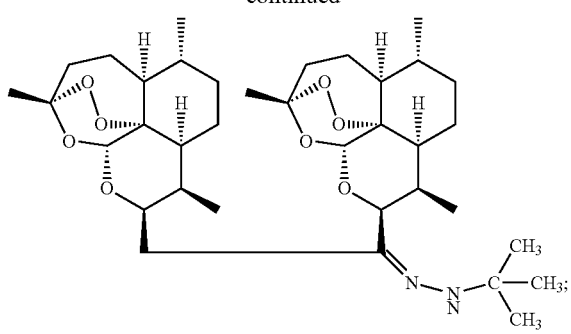
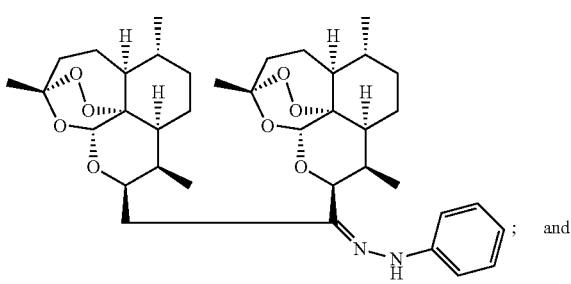
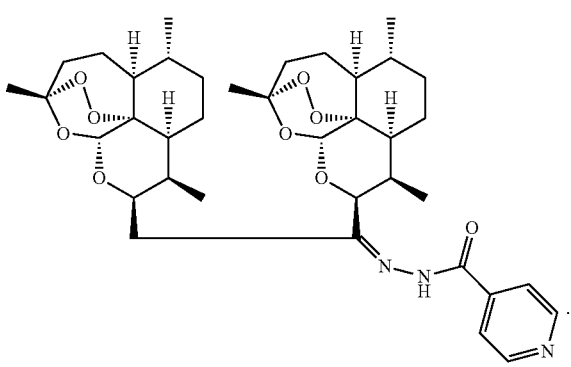
In yet further embodiments, X is CH—O—R$_4$ and the compound of Formula (I) is selected from the group consisting of:
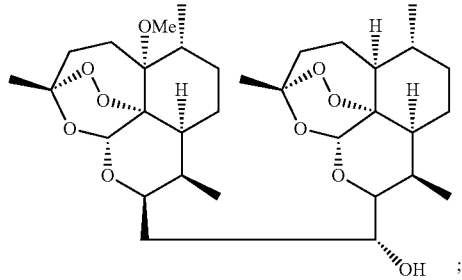
R-25
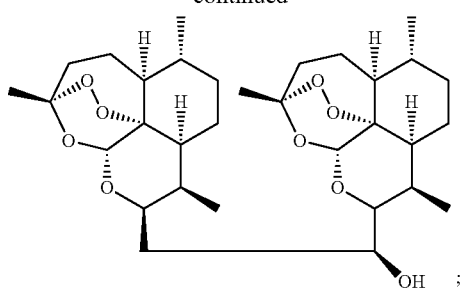
S-26
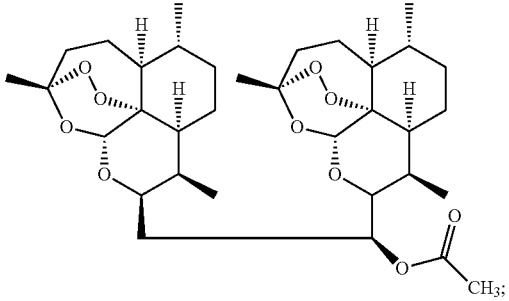
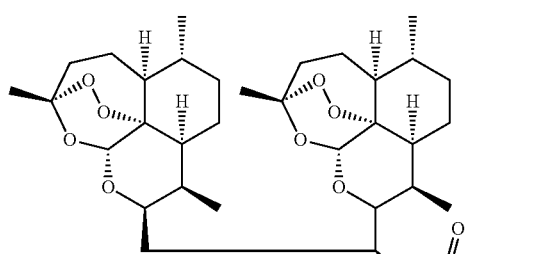
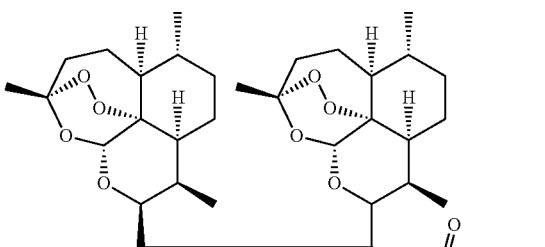
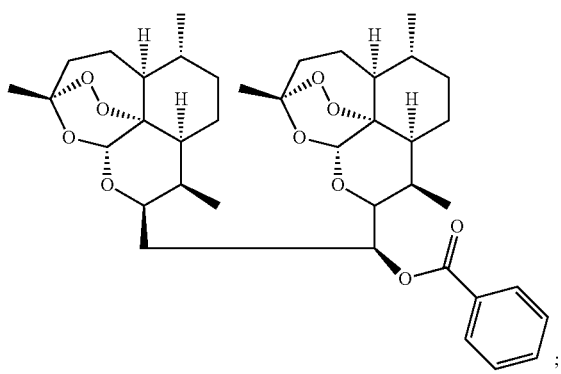

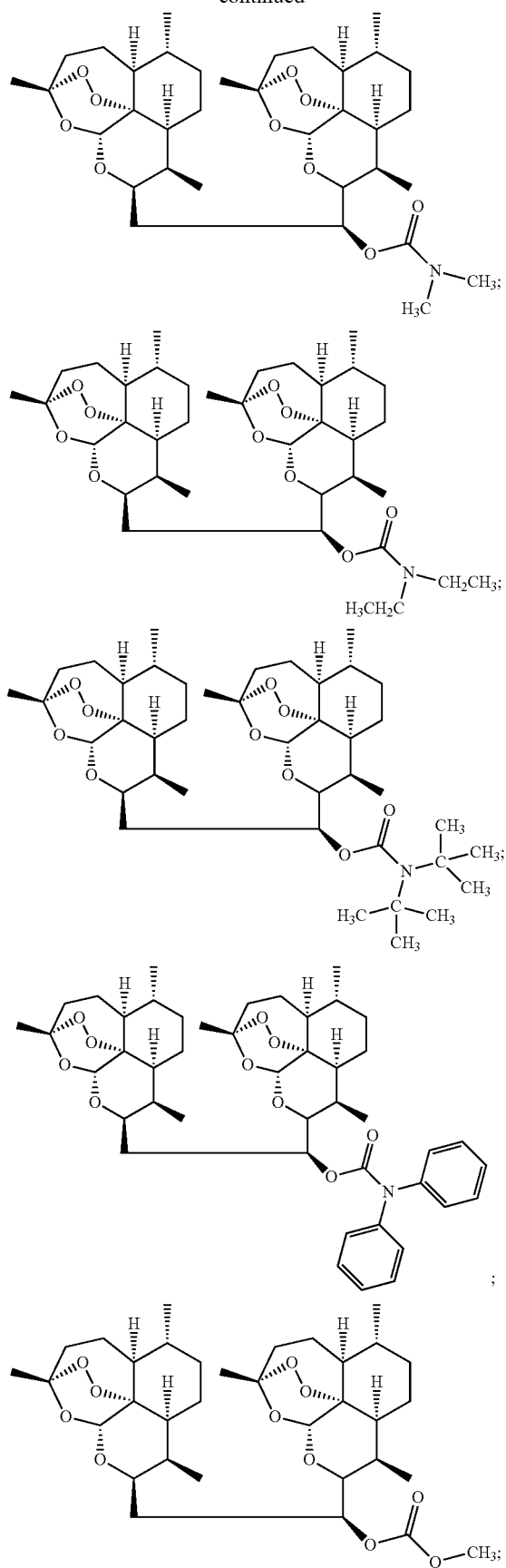
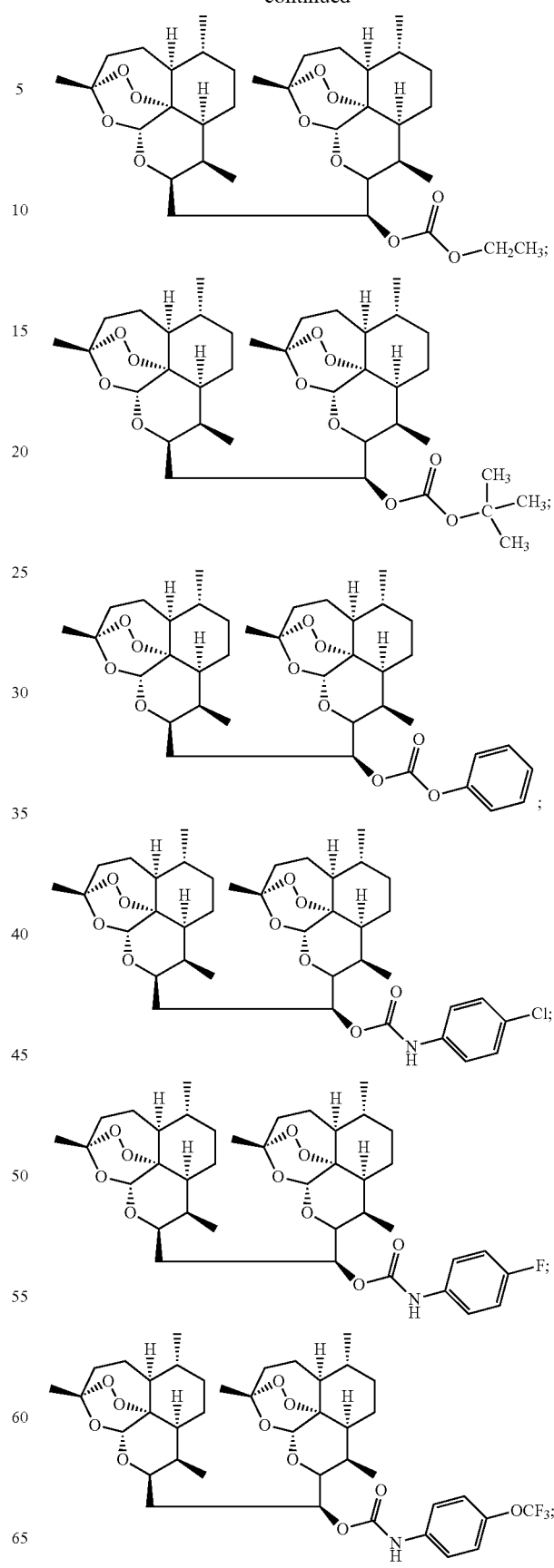

-continued
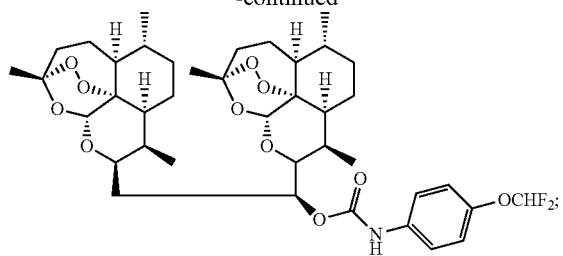
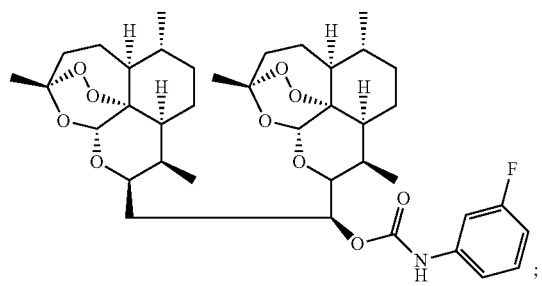
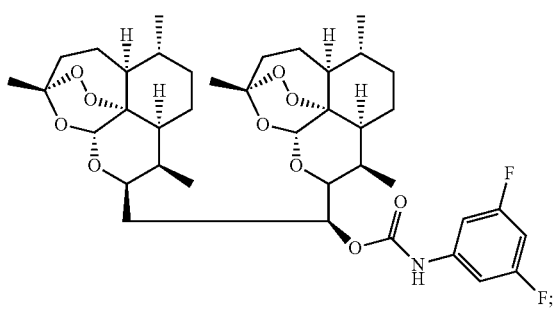
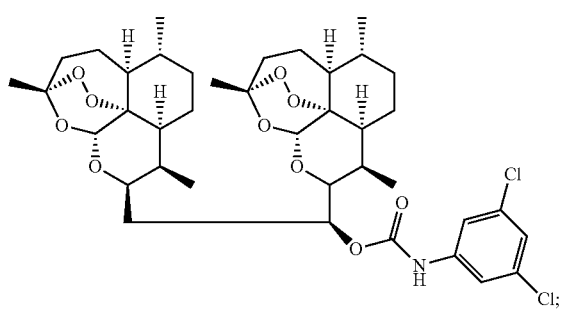
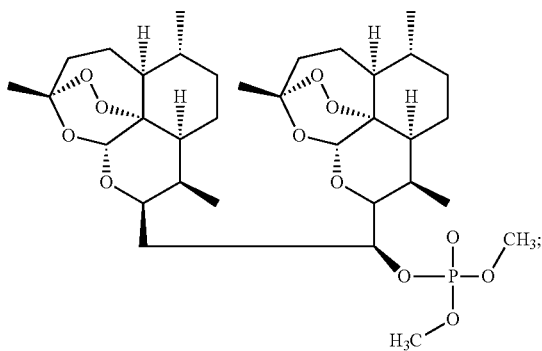
-continued
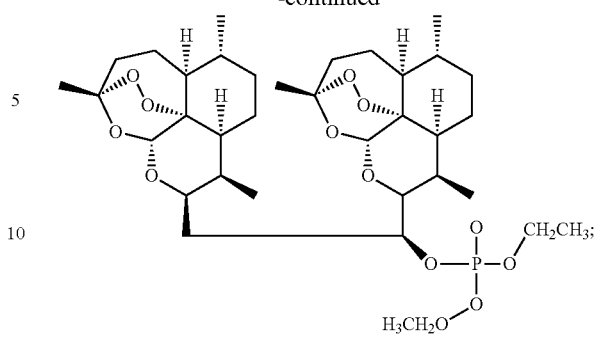
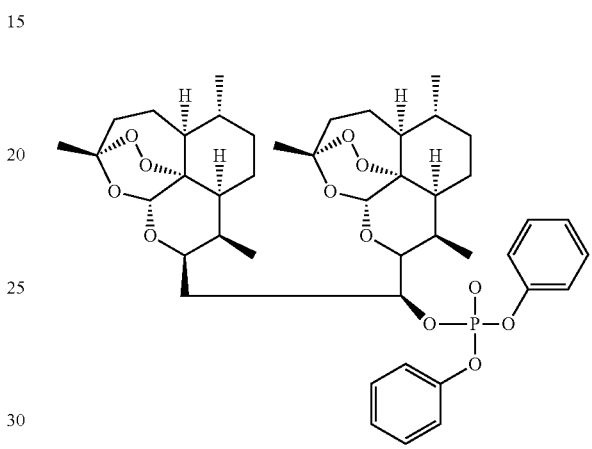
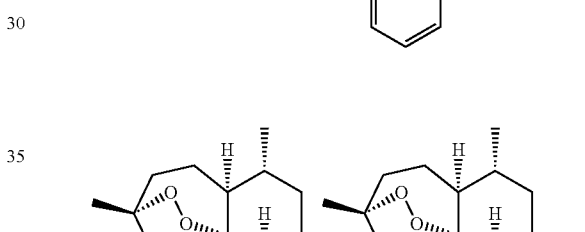
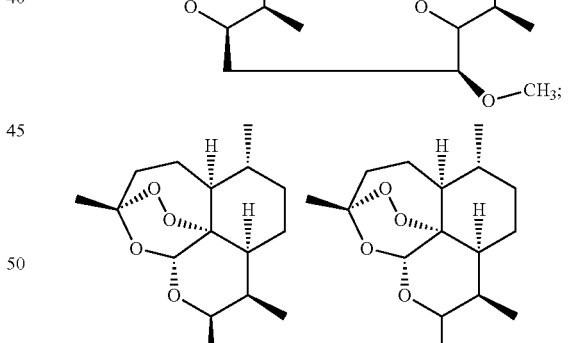
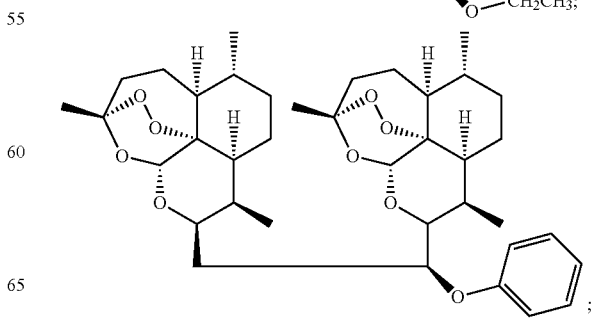

-continued

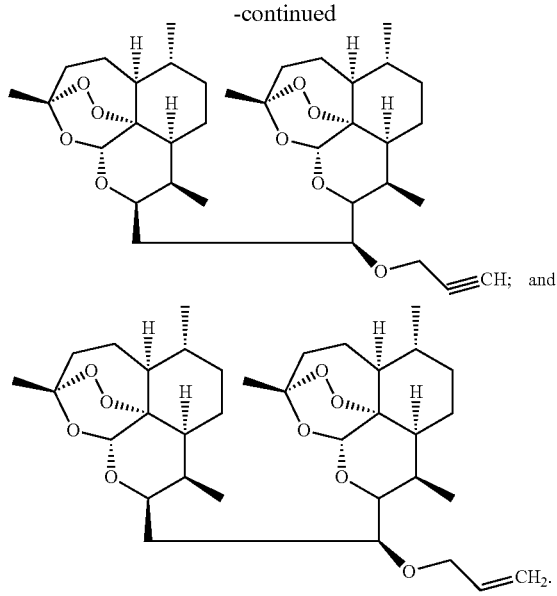

B. METHODS OF TREATMENT

In some embodiments, the presently disclosed two-carbon linked artemisinin-derived trioxane dimers of Formula (I) can be used for treating subjects infected with malaria or other parasitic infectious diseases including, but not limited to, toxoplasmic infection; subjects afflicted with psychiatric conditions associated with toxoplasmic infection; and subjects afflicted with cancer.

1. Methods of Treating a Subject Infected with Malaria

Each year approximately 200-300 million people experience a malarial illness and over 1 million individuals die. In patients with severe and complicated disease, the mortality rate is between 20 and 50%. *Plasmodium* is the genus of protozoan parasites that is responsible for all cases of human malaria and *Plasmodium falciparum* is the species of parasite that is responsible for the vast majority of fatal malaria infections. Malaria has traditionally been treated with quinolines, such as chloroquine, quinine, mefloquine, and primaquine, and with antifolates, such as sulfadoxine-pyrimethamine Unfortunately, most *P. falciparum* strains have now become resistant to chloroquine, and some, such as those in Southeast Asia, also have developed resistance to mefloquine and halofantrine; multidrug resistance also is developing in Africa.

The endoperoxides are a promising class of antimalarial drugs that may meet the dual challenges posed by drug-resistant parasites and the rapid progression of malarial illness. As discussed hereinabove, the first generation endoperoxides include natural artemisinin and several synthetic derivatives. Artemisinin has been used successfully to treat malaria patients throughout the world, including those infected with both chloroquine-sensitive and chloroquine-resistant strains of *P. falciparum*. Although artemisinin is effective at suppressing the parasitemias of *P. vivax* and *P. falciparum*, the problems encountered with recrudescence, and the compound's insolubility in water, led scientists to modify artemisinin chemically, a difficult task because of the chemical reactivity of the peroxide linkage, which is believed to be an essential moiety for antimalarial activity. In some embodiments, the presently disclosed subject matter provides a new series of two-carbon linked artemisinin-derived trioxane dimers useful for treating subjects infected with malaria.

Accordingly, the presently disclosed subject matter provides a method of treating a subject infected with malaria, the method comprising administering to a subject in need of treatment thereof, a compound of Formula (I) as disclosed herein. In some embodiments, the method further comprises administering to the subject a quinoline anti-malarial drug, an antifolate, and/or a second anti-malarial drug, such as, lumefantrine, concurrently or sequentially with a compound of Formula (I). In particular embodiments, the quinoline anti-malarial drug is selected from the group consisting of chloroquine, quinine, mefloquine, and primaquine. In more particular embodiments, the anti-malarial drug is mefloquine. In some embodiments, the second anti-malarial drug is lumefantrine.

2. Methods of Treating Other Parasitic Infectious Diseases

In some embodiments, the presently disclosed two-carbon linked artemisinin-derived trioxane dimers are useful for preventing, treating and controlling infections, including but not limited to toxoplasmic infection, and psychiatric conditions associated with toxoplasmic infection. *Toxoplasma gondii* (*T. gondii*) is an apicomplexan protozoan of worldwide medical importance. Humans are infected by *T. gondii* through contact with feces from infected cats, by the consumption of undercooked meat from infected animals, or by transmission from infected mother to fetus. This parasite can cause systemic infection and widespread organ damage in immunocompromised individuals and neonates. Infection of immunocompetent adults can result in fever and adenopathy. Tenter et al., 2000. Serological studies indicate that *T. gondii* could be associated with chronic neuropsychiatric diseases or behavioral abnormalities in some populations. Bachmann et al., 2005; Yolken et al., 2001.

Available medications for the prevention and treatment of toxoplasma infection show limited efficacy and have substantial side effects. Georgiev 1994. Published studies have indicated that the naturally occurring 1,2,4-trioxane artemisinin and artemisinin derivatives, such as artemether, originally developed for the treatment of malaria, have the ability to inhibit toxoplasma replication in vitro. Berens et al., 1998; Chang et al., 1989; Holfels et al., 1994; Ou-Yang et al., 1990. While these trioxanes have a number of advantages in terms of rapid action and low levels of toxicity, they are limited in terms of absorption, bioavailability, and short half-life (i.e., easy hydrolysis into toxic dihydroartemisinin) Lin et al., 1987; O'Neill and Posner, 2004. Thus, what is needed are improved derivatives of artemisinin having not only rapid action and low levels of toxicity, but also better absorption, bioavailability, and longer half-lives for inhibiting the replication of *T. gondii*.

Selected derivatives of artemisinin exhibiting in vitro efficacy against *T. gondii* are disclosed in published PCT patent application no. WO2008/127381 to Brando et al., which is incorporated herein by reference in its entirety. The artemisinin derivatives disclosed in WO2008/127381 also have been shown to inhibit the replication of chloroquine-sensitive *Plasmodium falciparum*. Accordingly, in some embodiments, the presently disclosed subject matter provides methods of using the presently disclosed two-carbon linked artemisinin-derived trioxane dimers and compositions for preventing, controlling or treating infectious diseases, including but not limited to, parasitic infectious diseases, such as *T. gondii* infection, trypanosome parasite infection, plasmodia parasite infection, and *Cryptosporidium* parasite infection.

Further, the evidence linking infection with *T. gondii* to the etiology of schizophrenia is well known. Torrey et al., 2007. Epidemiologic studies have indicated that infectious agents may contribute to some cases of schizophrenia. In animals, infection with *T. gondii* can alter behavior and neurotransmitter function. In humans, acute infection with *T. gondii* can produce psychotic symptoms similar to those displayed by persons with schizophrenia. Since 1953, a total of 19 studies of *T. gondii* antibodies in persons with schizophrenia and other severe psychiatric disorders and in controls have been reported; 18 reported a higher percentage of antibodies in the affected persons; in 11 studies the difference was statistically significant. Two other studies found that exposure to cats in childhood was a risk factor for the development of schizophrenia. Some medications used to treat schizophrenia inhibit the replication of *T. gondii* in cell culture. Jones-Brando et al., 2003. Establishing the role of *T. gondii* in the etiopathogenesis of schizophrenia may lead to new medications for its prevention and treatment.

Schizophrenia is a pervasive neuropsychiatric disease of uncertain cause that affects approximately 1% of the adult population in the United States and Europe. An increased occurrence of schizophrenia in family members of affected persons suggests that genetic factors play a role in its etiology, and some candidate predisposing genes have been identified. Environmental factors also are important. Epidemiologic studies, for example, have established that winter-spring birth, urban birth, and perinatal and postnatal infection are all risk factors for the disease developing in later life. These studies have rekindled an interest in the role of infectious agents in schizophrenia, a concept first proposed in 1896.

*T. gondii* is an intracellular parasite in the phylum Apicomplexa. Its life cycle can be completed only in cats and other felids, which are the definitive hosts. *T. gondii*, however, also infects a wide variety of intermediate hosts, including humans. In many mammals, *T. gondii* is known to be an important cause of abortions and stillbirths and to selectively infect muscle and brain tissue. A variety of neurologic symptoms, including incoordination, tremors, head-shaking, and seizures, has been described in sheep, pigs, cattle, rabbits, and monkeys infected with *T. gondii*. Humans may become infected by contact with cat feces or by eating undercooked meat.

The importance of these modes of transmission may vary in different populations. Individual response to *Toxoplasma* infection is determined by immune status, timing of infection, and the genetic composition of the host and the organism. *Toxoplasma* organisms also have been shown to impair learning and memory in mice and to produce behavioral changes in both mice and rats. Of special interest are studies showing that *Toxoplasma*-infected rats become less neophobic, leading to the diminution of their natural aversion to the odor of cats. These behavioral changes increase the chances that the rat will be eaten by a cat, thus enabling *Toxoplasma* to complete its life cycle, an example of evolutionarily driven manipulation of host behavior by the parasite.

In humans, toxoplasma is an important cause of abortions and stillbirths after primary infection in pregnant women. The organism also can cross the placenta and infect the fetus. The symptoms of congenital toxoplasmosis include abnormal changes in head size (hydrocephaly or microcephaly), intracranial calcifications, deafness, seizures, cerebral palsy, damage to the retina, and mental retardation. Some sequelae of congenital toxoplasmosis are not apparent at birth and may not become apparent until the second or third decade of life. Hydrocephalus, increased ventricular size, and cognitive impairment also have been noted in some persons with schizophrenia and other forms of psychosis.

Some cases of acute toxoplasmosis in adults are associated with psychiatric symptoms, such as delusions and hallucinations. Schizophrenia was first diagnosed in these patients, but later neurologic symptoms developed, which led to the correct diagnosis of *Toxoplasma* encephalitis.

Chlorpromazine (THORAZINE®) is the first antipsychotic medication used for schizophrenia, which was soon followed by other medications, such as haloperidol (HALDOL®), fluphenazine (PROLIXIN®), thiothixene (NA VANE®), trifluoperazine (STELAZINE®), perphenazine (TRILAFON®), and thioridazine (MELLARIL®). These medications have become known as "neuroleptics" because, although effective in treating positive symptoms (i.e., acute symptoms such as hallucinations, delusions, thought disorder, loose associations, ambivalence, or emotional lability), cause side effects, many of which affect the neurologic (nervous) system.

A new class of antipsychotics (atypical antipsychotics) was introduced after 1989. At clinically effective doses, no (or very few) of these neurological side effects, which often affect the extrapyramidal nerve tracts (which control such things as muscular rigidity, painful spasms, restlessness, or tremors) are observed. The first of the new class, clozapine (CLOZARIL®) is the only agent that has been shown to be effective where other antipsychotics have failed. Its use is not associated with extrapyramidal side effects, but it does produce other side effects, including possible decrease in the number of white cells, so the blood needs to be monitored every week during the first 6 months of treatment and then every 2 weeks to catch this side effect early if it occurs. Other atypical antipsychotics include risperidone (RISPERDAL®), olanzapine (ZYPREXA®), quetiapine (SEROQUEL®), ziprasidone (GEODON®), and aripiprazole (ABILITY®). The use of these medications has allowed successful treatment and release back to their homes and the community for many people suffering from schizophrenia.

Accordingly, in some embodiments, the presently disclosed subject matter provides a method for treating psychiatric disorders associated with toxoplasma infection including, but not limited to, schizophrenia, using the presently disclosed two-carbon linked artemisinin-derived trioxane dimers of Formula (I) and compositions thereof alone or in combination with one or more antipsychotic drugs including, but not limited to, chlorpromazine (THORAZINE®), haloperidol (HALDOL®), fluphenazine (PROLIXIN®), thiothixene (NA VANE®), trifluoperazine (STELAZINE®), perphenazine (TRILAFON®), and thioridazine (MELLARIL®), clozapine (CLOZARIL®), risperidone (RISPERDAL®), olanzapine (ZYPREXA®), quetiapine (SEROQUEL®), ziprasidone (GEODON®), and aripiprazole (ABILIFY®).

3. Methods of Treating Cancer

Since the isolation of artemisinin, there has been a concerted effort by investigators to study other therapeutic applications of artemisinin and its derivatives. The National Institutes of Health reported that artemisinin is inactive against P388 leukemia (NCI Report on NSC 369397, tested on 25 Oct. 1983). Later anticancer studies that have been conducted on cell line panels consisting of 60 lines organized into nine, disease-related subpanels including leukemia, non-small-cell lung cancer, colon, CNS, melanoma, ovarian, renal, prostate, and breast cancers, further confirm that artemisinin displays modest anticancer activity.

While artemisinin and its related derivatives demonstrate zero to slight antiproliferative and antitumor activity, it has been discovered that a class of artemisinin dimer compounds exhibits antiproliferative and antitumor activities that are, in vitro, equivalent to or greater than known antiproliferative and antitumor agents (U.S. Pat. No. 5,677,468 also incorporated herein by reference in its entirety for all purposes). Unfortunately, while the in vitro results of these artemisinin compounds are encouraging, these compounds do not appear to have as significant antitumor activity on the treatment of tumor cells in mice. There is still a need, therefore, to develop stable artemisinin derivatives and structural analogs thereof having antimalarial, anticancer, antiproliferative, and antitumor activities that are equivalent to or greater than those of known antimalarial, anticancer, antiproliferative and antitumor agents, respectively.

For example, selected artemisinin-related dimers, e.g., trioxane dimer sulfur compounds, having anticancer activity have been disclosed in international PCT patent application publication no. WO2010/009428, to Posner and Rosenthal, which is incorporated herein by reference in its entirety. Other artemisinin analogs, including trioxane dimers have been shown to exhibit anti-cancer activity. See, e.g., U.S. patent application publication nos. US2009/0291923, to Posner et al., published Nov. 26, 2009; US2006/0142377 to Posner et al., published Jun. 29, 2006; and US2002/0055528 to Posner et al., published May 9, 2002, each of which is incorporated herein by reference in its entirety.

Accordingly, in some embodiments, the presently disclosed subject matter provides a method for treating cancer in a subject in need of such treatment, by administering to the subject a therapeutically effective amount of the presently disclosed two-carbon linked artemisinin-derived trioxane dimers of Formula (I). The cancer can include leukemia, non-small cell lung cancer, colon cancer, central nervous system cancer, melanoma cancer, ovarian cancer, renal cancer, prostate cancer, and breast cancer.

As used herein, the term "inhibit" or "inhibits" means to decrease, suppress, attenuate, diminish, arrest, or stabilize the development or progression of a disease, disorder, or condition, or the activity of a biological pathway, e.g., by at least 10%, 20%, 30%, 40%, 50%, 60%, 70%, 80%, 90%, 95%, 98%, 99%, or even 100% compared to an untreated control subject, cell, or biological pathway. By the term "decrease" is meant to inhibit, suppress, attenuate, diminish, arrest, or stabilize a symptom of a disease, disorder, or condition. It will be appreciated that, although not precluded, treating a disease, disorder or condition does not require that the disease, disorder, condition or symptoms associated therewith be completely eliminated.

As used herein, the terms "treat," treating," "treatment," and the like, are meant to decrease, suppress, attenuate, diminish, arrest, the underlying cause of a disease, disorder, or condition, or to stabilize the development or progression of a disease, disorder, condition, and/or symptoms associated therewith. The terms "treat," "treating," "treatment," and the like, as used herein can refer to curative therapy, prophylactic therapy, and preventative therapy. The treatment, administration, or therapy can be consecutive or intermittent. Consecutive treatment, administration, or therapy refers to treatment on at least a daily basis without interruption in treatment by one or more days. Intermittent treatment or administration, or treatment or administration in an intermittent fashion, refers to treatment that is not consecutive, but rather cyclic in nature. Treatment according to the presently disclosed methods can result in complete relief or cure from a disease, disorder, or condition, or partial amelioration of one or more symptoms of the disease, disease, or condition, and can be temporary or permanent. The term "treatment" also is intended to encompass prophylaxis, therapy and cure.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

By "agent" is meant a compound of Formula (I) or another agent, e.g., another small molecule compound administered in combination with a compound of Formula (I). More generally, the term "therapeutic agent" means a substance that has the potential of affecting the function of an organism. Such an agent may be, for example, a naturally occurring, semi-synthetic, or synthetic agent. For example, the therapeutic agent may be a drug that targets a specific function of an organism. A therapeutic agent also may be a nutrient. A therapeutic agent may decrease, suppress, attenuate, diminish, arrest, or stabilize the development or progression of disease, disorder, or condition in a host organism.

The term "administering" as used herein refers to administering a compound of Formula (I) to a subject in need of treatment, as well as introducing the presently disclosed compounds into a medium in which a target microorganism is cultured.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, e.g., optic crush experiments, and the like).

C. PHARMACEUTICAL COMPOSITIONS

The presently disclosed pharmaceutical compositions and formulations include pharmaceutical compositions of compounds of Formula (I), alone or in combination with one or more additional therapeutic agents, in admixture with a physiologically compatible carrier, which can be administered to a subject, for example, a human subject, for therapeutic or prophylactic treatment. As used herein, "physiologically compatible carrier" refers to a physiologically acceptable diluent including, but not limited to water, phosphate buffered saline, or saline, and, in some embodiments, can include an adjuvant. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. Adjuvants suitable for use with the presently disclosed compositions include adjuvants known in the art including, but not limited to, incomplete Freund's adjuvant, aluminum phosphate, aluminum hydroxide, and alum.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

One of skill in the art will recognize that the pharmaceutical compositions include the pharmaceutically acceptable salts of the compounds described above. The term "pharmaceutically acceptable salts" is meant to include salts of active compounds, which are prepared with relatively nontoxic acids or bases, depending on the particular substituent moieties found on the compounds described herein.

When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include alkali or alkaline earth metal salts including, but not limited to, sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids including, but not limited to, hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids, such as acetic (acetates), propionic (propionates), isobutyric (isobutyrates), maleic (maleates), malonic, benzoic (benzoates), succinic (succinates), suberic, fumaric (fumarates), lactic (lactates), mandelic (mandelates), phthalic (phthalates), benzenesulfonic (benzosulfonates), p-tolylsulfonic, citric (citrates), tartaric (tartrates, e.g., (+)-tartrates, (−)-tartrates or mixtures thereof including racemic mixtures), methanesulfonic, and the like. Other pharmaceutically acceptable salts, include, but are not limited to, besylate, bicarbonate, bitartrate, bromide, calcium edetate, camsylate, carbonate, edetate, edisylate, estolate, esylate, gluceptate, gluconate, glutamate, glycollylarsanilate, hexylresorcinate, hydrabamine, hydroxynaphthoate, iodide, isethionate, lactobionate, malate, mesylate, mucate, napsylate, nitrate, pamoate (embonate), pantothenate, phosphate/diphosphate, polygalacturonate, salicylate, stearate, subacetate, sulfate, tannate, and teoclate, also are included.

Also included are salts of amino acids, such as arginate and the like, and salts of organic acids, such as, glucuronic or galactunoric acids, and the like. See, for example, Berge et al, "Pharmaceutical Salts", Journal of Pharmaceutical Science, 1977, 66, 1-19. Some compounds of the present disclosure can contain both basic and acidic functionalities, which allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties. For example, salts tend to be more soluble in aqueous or other protonic solvents than are the corresponding free base forms.

Certain compounds of the present disclosure can exist in unsolvated forms, as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds that can be in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

D. COMBINATION THERAPIES

In certain embodiments, presently disclosed subject matter also includes combination therapies. Depending on the particular disease, disorder, or condition to be treated or prevented, additional therapeutic agents, which are normally administered to treat or prevent that condition, may be administered in combination with the compounds of this disclosure. These additional agents may be administered separately, as part of a multiple dosage regimen, from the composition comprising a compound of Formula (I). Alternatively, these agents may be part of a single dosage form, mixed together with the compound of Formula (I) in a single composition.

By "in combination with" is meant the administration of a compound of Formula (I) with one or more therapeutic agents either simultaneously, sequentially, or a combination thereof. Therefore, a cell or a subject administered a combination of a compound of Formula (I) can receive a compound of Formula (I) and one or more therapeutic agents at the same time (i.e., simultaneously) or at different times (i.e., sequentially, in either order, on the same day or on different days), so long as the effect of the combination of both agents is achieved in the cell or the subject. When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formula (I) and one or more therapeutic agents are administered simultaneously, they can be administered to the cell or administered to the subject as separate pharmaceutical compositions, each comprising either a compound of Formula (I) or one or more therapeutic agents, or they can contact the cell as a single composition or be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered compound is not diminished by the sequential, simultaneous or separate administration of the subsequent compound(s).

The presently disclosed compounds of Formula (I) can be optionally combined with or administered in concert with each other or other agents known to be useful in the treatment of the relevant disease, disorder, or condition. The combination therapies can involve concurrent or sequential administration, by the same or different routes, as determined to be appropriate by those of skill in the art. The presently disclosed subject matter also includes pharmaceutical compositions and kits including combinations as described herein.

Depending upon the particular condition, or disease state, to be treated or prevented, additional therapeutic agents, which are normally administered to treat or prevent that condition, may be administered together with the inhibitors of this disclosure. For example, chemotherapeutic agents or other antiproliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents in which the presently disclosed two-carbon linked artemisinin-derived trioxane dimers also can be combined with include, without limitation, anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors, such as acetylcholinesterase inhibitors, MAO inhibitors, interferons, anti-convulsants, ion channel blockers, riluzole, and anti-parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders, such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

E. DOSAGE AND MODE OF ADMINISTRATION

The presently disclosed pharmaceutical compositions can be administered using a variety of methods known in the art depending on the subject and the particular disease, disorder, or condition being treated. The administering can be carried out by, for example, intravenous infusion; injection by intravenous, intraperitoneal, intracerebral, intramuscular, intraocular, intraarterial or intralesional routes; or topical or ocular application.

More particularly, as described herein, the presently disclosed compounds can be administered to a subject for therapy by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

For intracerebral use, the compounds can be administered continuously by infusion into the fluid reservoirs of the CNS, although bolus injection may be acceptable. The presently disclosed compounds can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the presently disclosed compounds can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

The presently disclosed pharmaceutical compositions can be manufactured in a manner known in the art, e.g. by means of conventional mixing, dissolving, granulating, drageemaking, levitating, emulsifying, encapsulating, entrapping or lyophilizing processes.

More particularly, pharmaceutical compositions for oral use can be obtained through combination of active compounds with a solid excipient, optionally grinding a resulting mixture, and processing the mixture of granules, after adding suitable auxiliaries, if desired, to obtain tablets or dragee cores. Suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of active compound, e.g., dosage, or different combinations of active compound doses.

Pharmaceutical compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the active compounds can be dissolved or suspended in suitable liquids, such as fatty oils, liquid paraffin, or liquid polyethylene glycols (PEGs), with or without stabilizers. Stabilizers can be added as warranted.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al., J. Biomed. Mater. Res. 15:167, 1981; Langer, Chem. Tech. 12:98, 1982), ethylene vinyl acetate (Langer et al., Id), or poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy. Such materials can comprise an implant, for example, for sustained release of the presently disclosed compounds, which, in some embodiments, can be implanted at a particular, predetermined target site.

Pharmaceutical compositions for parenteral administration include aqueous solutions of active compounds. For injection, the presently disclosed pharmaceutical compositions can be formulated in aqueous solutions, for example, in some embodiments, in physiologically compatible buffers, such as Hank's solution, Ringer' solution, or physiologically buffered saline. Aqueous injection suspensions can contain substances that increase the viscosity of the suspension, such as sodium carboxymethyl cellulose, sorbitol, or dextran. Additionally, suspensions of the active compounds or vehicles include fatty oils, such as sesame oil, or synthetic fatty acid esters, such as ethyl oleate or triglycerides, or liposomes. Optionally, the suspension also can contain suitable stabilizers or agents that increase the solubility of the compounds to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

In other embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

The presently disclosed subject matter also includes the use of a compound of Formula (I) in the manufacture of a medicament for treating the presently disclosed diseases.

Regardless of the route of administration selected, the presently disclosed compounds, which may be used in a suitable hydrated form, and/or the pharmaceutical compositions are formulated into pharmaceutically acceptable dosage forms such as described below or by other conventional methods known to those of skill in the art.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Actual dosage levels of the active ingredients in the presently disclosed pharmaceutical compositions can be varied so as to obtain an amount of the active ingredient that is effective to achieve the desired therapeutic response for a particular subject, composition, route of administration, and disease, disorder, or condition without being toxic to the subject. The selected dosage level will depend on a variety of factors including the activity of the particular compound employed, or salt thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of Formula (I) employed in the pharmaceutical composition at levels lower than that required to achieve the desired therapeutic effect and gradually increase the dosage until the desired effect is achieved. Accordingly, the dosage range for administration will be adjusted by the physician as necessary. It will be appreciated that an amount of a compound required for achieving the desired biological response may be different from the amount of compound effective for another purpose.

In general, a suitable daily dose of a compound of Formula (I) will be that amount of the compound that is the lowest dose effective to produce a therapeutic effect. Such an effective dose will generally depend upon the factors described above. Generally, doses of the compounds of Formula (I) will range from about 0.0001 to about 1000 mg per kilogram of body weight of the subject per day. In certain embodiments, the dosage is between about 1 µg/kg and about 500 mg/kg, more preferably between about 0.01 mg/kg and about 50 mg/kg. For example, in certain embodiments, a dose can be about 1, 5, 10, 15, 20, or 40 mg/kg/day.

If desired, the effective daily dose of the active compound can be administered as two, three, four, five, six or more sub-doses administered separately at appropriate intervals throughout the day, optionally, in unit dosage forms.

F. KITS OR PHARMACEUTICAL SYSTEMS

The presently disclosed compounds and compositions can be assembled into kits or pharmaceutical systems for use in treating or preventing the presently disclosed diseases, disorders, or conditions. In some embodiments, the presently disclosed kits or pharmaceutical systems include a compound of Formula (I) or pharmaceutically acceptable salts thereof. In particular embodiments, the compounds of Formula (I), or a pharmaceutically acceptable salt thereof, are in unit dosage form. In further embodiments, the compound of Formula (I), or a pharmaceutically acceptable salt, can be present together with a pharmaceutically acceptable solvent, carrier, excipient, or the like, as described herein.

In some embodiments, the presently disclosed kits comprise one or more containers, including, but not limited to a vial, tube, ampule, bottle and the like, for containing the compound. The one or more containers also can be carried within a suitable carrier, such as a box, carton, tube or the like. Such containers can be made of plastic, glass, laminated paper, metal foil, or other materials suitable for holding medicaments.

In some embodiments, the container can hold a composition that is by itself or when combined with another composition effective for treating or preventing the condition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The presently disclosed kits or pharmaceutical systems also can include associated instructions for using the compounds for treating or preventing a disease, disorder, or condition. In some embodiments, the instructions include one or more of the following: a description of the active compound; a dosage schedule and administration for treating or preventing a disease, disorder, or condition; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

G. CHEMICAL DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds that are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., C$_1$-C$_{10}$ means one to ten carbons). In particular embodiments, the term "alkyl" refers to C$_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_{1-8}$ straight-chain alkyls. In other embodiments, "alkyl" refers, in particular, to C$_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_{2S}$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups that are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); CH=CH—CH=CH—; —CH=CH—CH$_2$—; —CH$_2$CH$_2$CH$_2$CH$_2$—, —CH$_2$CH=CHCH$_2$—, —CH$_2$CsCCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O) OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). The term "haloaryl," however, as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

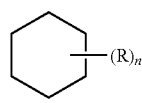

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

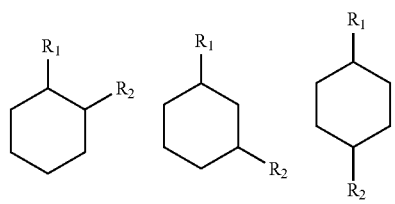

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ~~~~ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate," as well as their divalent derivatives) are meant to include both substituted and unsubstituted forms of the indicated group. Optional substituents for each type of group are provided below.

Substituents for alkyl, heteroalkyl, cycloalkyl, heterocyloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R"', —OC(O)R', —C(O)R', —$CO_2$R', —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"'—S(O)R', —S(O)$_2$R', —S(O)$_2$NR'R", —NRSO$_2$R', —CN and —$NO_2$, —R', —$N_3$, —CH(Ph)$_2$, fluoro($C_1$-$C_4$)alkoxo, and fluoro ($C_1$-$C_4$)alkyl, in a number ranging from zero to the total number of open valences on aromatic ring system; and where R', R", R"' and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R"', wherein R', R", and R"' are each independently selected from the group consisting of alkyl groups. Additionally, R', R", and/or R"' taken together may optionally be —(CH$_2$)$_k$— where k is an integer from 2 to 6. Examples include, but are not limited to, methylamino, dimethyl-amino, ethylamino, diethylamino, diethylaminocarbonyl, methylethylamino, iso-propylamino, piperidino, trimethylamino, and propylamino The amino group is —NR'R wherein R' and R'' are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C═O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

The term ureido refers to a urea group of the formula —NH—CO—$NH_2$.

Unless otherwise explicitly defined, a "substituent group," as used herein, includes a functional group selected from one or more of the following moieties, which are defined herein:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein also are meant to include all stereochemical forms of the structure; i.e., the R and S configurations for each asymmetric center. Therefore, single stereochemical isomers, as well as enantiomeric and diastereomeric mixtures of the present compounds are within the scope of the disclosure.

Unless otherwise stated, structures depicted herein also are meant to include compounds that differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure also may contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties also may be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

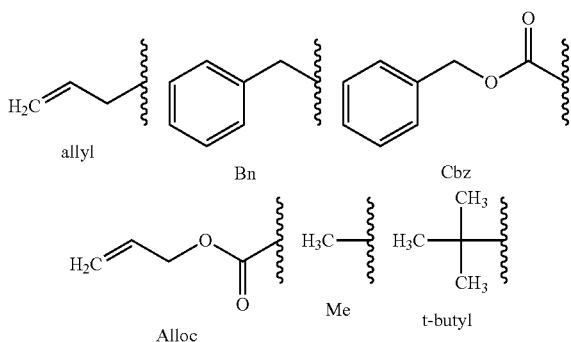

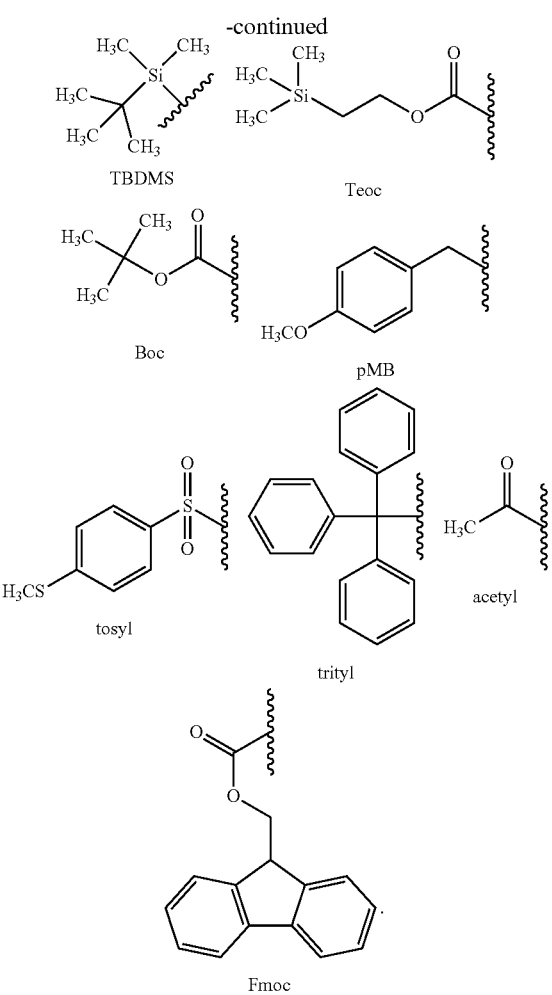

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Chemistry

Synthesis

The currently-used drugs artemether (4b) and artesunate (4c) contain a C10 acetal linkage (Scheme 1). It is generally accepted that this linkage is a significant metabolic liability. Both molecules 4b and 4c are rapidly catabolized to dihydroartemisinin (DHA, 13, Scheme 1) and excreted following glucuronidation. Methodology has been previously developed to replace the C10 acetal linkage with a carbon-carbon bond, Pu and Ziffer, 1995, and Ma, et al., 2000, and these molecules are called C10-carba analogs. These analogs have shown increased stability in simulated stomach conditions as compared to the first generation acetals artemether (4b) and artesunate (4c), Jung, et al., 2002, but have yet to translate into a marketed drug. The presently disclosed subject matter provides the synthesis of a two-carbon linked artemisinin dimer that might have distinct benefits over dimers of greater linker lengths.

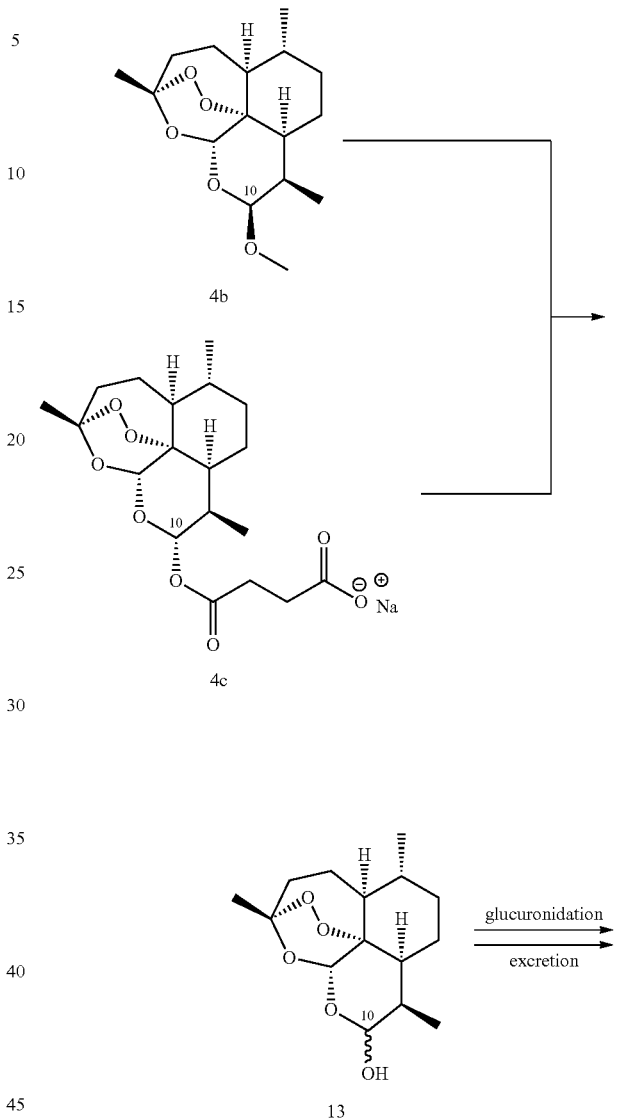

Scheme 1. Excretion pathway of first-generation artemisinin derivatives.

The main obstacle in synthesizing such a molecule is the tremendous steric interaction that would likely occur between two artemisinin units joined through such a short distance. Established methodology follows a pathway using a Lewis acid activation of an appropriately functionalized artemisinin precursor (Scheme 2). In this pathway, artemisinin is functionalized with an appropriate leaving group (LG) at the C10 position (general structure 14, Scheme 2), which is thought to form oxocarbenium ion 15 in situ after Lewis acid activation. Treatment with a nucleophile can then proceed through either one of two pathways—ideally nucleophilic addition occurs at C10, providing desired products of general structure 16. The C9 proton, however, also is easily accessible and elimination is a major competing pathway, particularly with harder nucleophiles, leading to undesired elimination product 17.

Scheme 2. Nucleophilic substitution at C10 and competing elimination pathway.

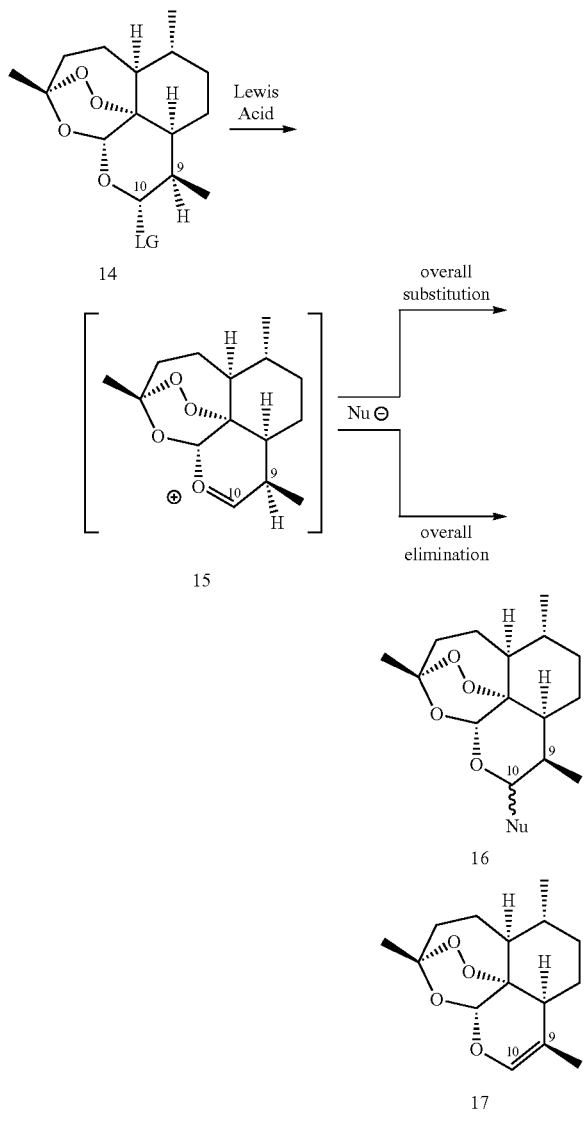

With this reactivity in mind, a two-carbon linker unit, which could be made nucleophilic in successive steps was prepared. The acetylene unit became the focus because substituted acetylides have previously achieved substitution at the C10 position by reacting an electrophilic C10 fluoride analog with nucleophilic trimethylaluminum-activated acetylenes. Posner, et al., 1999. This methodology, however, was low-yielding and the C10 fluoride is difficult to manipulate. As such, a more robust method was required. Organometallic reagents have achieved substitution at the C10 position, Posner, et al., 1999, and the commercially available ethynyl Grignard would allow installation of the acetylene unit. Initial attempts to introduce the acetylene unit at the C10 position using the common electrophilic precursor dihydroartemisinin acetate (DHA-OAc, 19, Scheme 3) provided almost exclusively the undesired elimination product 17, likely due to the highly basic (and weakly nucleophilic) nature of the Grignard acetylide reagent. Efforts were still futile upon addition of zinc(II) chloride ($ZnCl_2$), in an attempt to form a more nucleophilic zinc-magnesium hybrid species (likely [{$Mg_2Br_3(Et_2O)_6$}$^+${$Zn(acetylene)_3$}$^-$]) in situ. Hevia, et al., 2010, and Hatano, et al., 2010.

A new precursor containing a nucleophile assisting leaving group, Lepore and Mondal, 2007, was synthesized to form a chelating intermediate that would direct the organometallic reagent to the C10 position. Using standard procedure, the artemisinin lactone was reduced using diisobutylaluminum hydride (DIBALH) at −78° C. The resulting oxyanion can be trapped with the appropriate electrophile (in this case 2,4-dimethoxybenzoyl chloride 18) directly in situ to provide exclusively the desired C10-α-2,4-dimethoxybenzoate intermediate 20 (Scheme 3). The 2,4-dimethoxybenzoate group is an electron rich moiety to which $ZnCl_2$ or other Lewis acidic organometallic species can strongly chelate. The previously described zinc-magnesium hybrid nucleophile would be directed to the C10 position upon coordination to the benzoate. Simultaneous addition of the Lewis acid $ZnCl_2$ and ethynylmagnesium bromide to stirring solution of benzoate 20 at −5° C. provided the previously unreported C10 β-alkyne product 21. The best results were achieved with a 3.5:1.1 ratio of the Grignard reagent to $ZnCl_2$, which is consistent with previous studies that generated similar reagents. Hevia, et al., 2010, and Hatano, et al., 2010.

Scheme 3. C10-alkyne synthesis via 2,4-dimethoxybenzoate intermediate 20 and similar preparation of DHA-OAc 19.

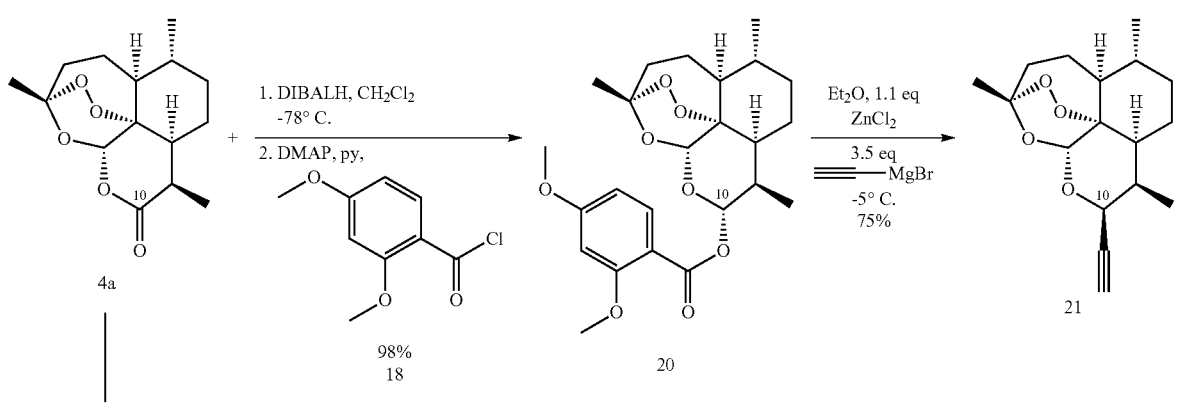

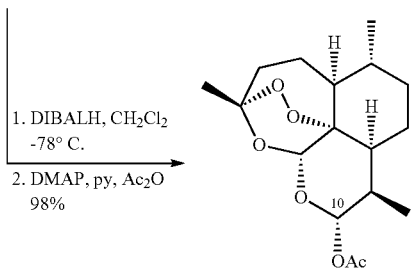

19

With the alkyne 21 prepared in good yields, the two-carbon linked system was within reach. Attempts to convert the terminal alkyne 21 into a Grignard reagent (and into other organometallic reagents, for example, a dimethylaluminate, Posner, et al., 1999, or a tri-n-butylstannane, not shown) and then simply to repeat the newly established coupling procedure with chelating benzoate 20 led to decomposition of starting material. It was hypothesized that the large bulk of the artemisinin prevented attachment to a second artemisinin via a straight-on attack that would be required of a linear alkyne, so efforts shifted to conversion of the alkyne into alternate functionality.

Ziffer has established that trimethylsilyl (TMS) enol ethers could react with DHA-OAc 19 to form C10 carba analogs in good yields, Ma, et al., 2000, and, without wishing to be bound to any one particular theory, it was thought that if the alkyne could be converted into a TMS enol ether, then similar reactivity would be achieved. Treatment of the alkyne 21 with p-toluenesulfonic acid (pTsOH) and mercury(II) acetate [(HgOAc)$_2$] in water and acetone afforded the C10 methyl ketone 22 in excellent yield (Scheme 4). Subsequent conversion into TMS enol ether 23 was accomplished by treatment of the methyl ketone 22 with a solution of freshly prepared lithium diisopropylamide (LDA) in tetrahydrofuran (THF) in the presence of chlorotrimethylsilane (TMSCl) and triethylamine (Et$_3$N) at −78° C. The TMS enol ether 23 is surprisingly stable to silica gel and can be isolated and characterized as a clean material, but it must be used immediately.

The final step for the formation of the two-carbon linked system was then achieved by following established protocol. Rosenthal, et al., 2009, Pu and Ziffer, 1995. Slow addition of tin(IV) chloride (SnCl$_4$) into a solution of TMS enol ether 23 and DHA-OAc 19 at −78° C. gave, for the first time, the two-carbon linked dimer ketone 24 in good yield. The dimer is prepared in five linear steps starting from artemisinin in 37% overall yield.

Scheme 4. Synthesis of two-carbon linked artemisinin dimer.

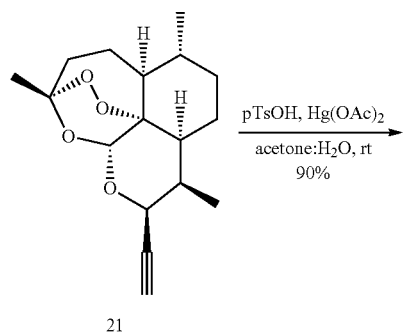

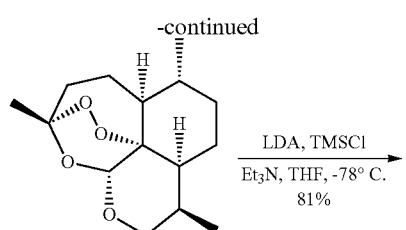

22

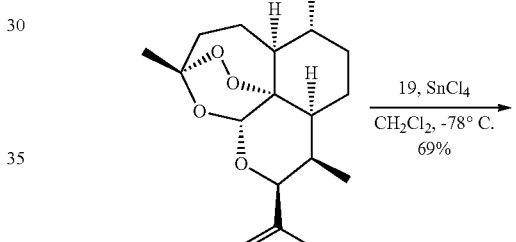

23

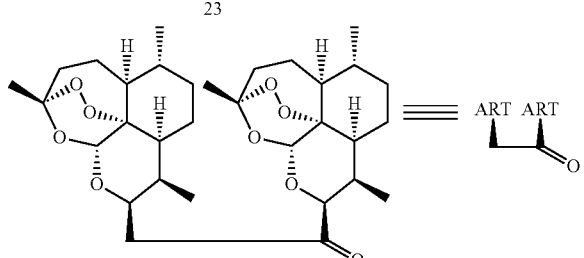

24

Analog Synthesis

A number of analogs were prepared to add diversity to this chemical series and to probe SAR. The dimer ketone 24 was first reduced into a pair of diastereomeric alcohols 25 and 26 that were easily separable on silica gel (Scheme 5a). Surprisingly, even with a bulky reducing agent such as diisobutylaluminum hydride (DIBALH), the alcohols were obtained in a 1:1 ratio. Treatment with R-CBS-oxazaborolidine, Corey, et al., 1987, 27a and borane in tetrahydrofuran (BH$_3$:THF), however, achieved stereoselective reduction of the ketone (98% de as determined by proton NMR of the crude reaction mixture), allowing direct access to S-26. Employing S-CBS oxazaborolidine 27b did not afford the same selectivity, as both alcohol products R-25 and S-26 were formed in a 62:48 ratio under these conditions.

Additionally, a series of oxime derivatives were prepared. The oxime functionality was desirable because it is already contained in known drugs, Musilek, et al., 2009, has shown activity against protozoa. Krivogorksy, et al., 2008; Gibson, et al., 2009. Evidence suggests that it is a suitable "water-soluble prodrug" that might unveil the ketone under biological conditions. Huttunen, et al., 2006; Venhuis, et al., 2003; Kumpulainen, et al., 2006; and Prokai, L., et al., 1995. The initial series of analogs, prepared by treating the dimer ketone 24 with the appropriate commercially available hydroxylamine in pyridine, consisted of the parent oxime 28, the O-methyl oxime 29, and the 0-allyl oxime 30 (Scheme 5b). Analogs containing bulkier alkyl groups also were prepared and included cyclopropylmethylene oxime 31, isobutyloxime 32, and tert-butyloxime 33. While two geometric isomers of the oxime would be expected, the Z-isomer was favored, and in some cases was the only isomer produced (stereochemical implications will be discussed, vide infra). The parent oxime 28 was further converted into the O-propargyloxime 34, O-dimethyl carbamoyloxime 35, O-acetate oxime 36, and a pair of O-phosphate oximes (dimethyl 37, diethyl 38) upon treatment with sodium hydride (NaH) and the appropriate halide in THF at 0° C. (Scheme 5c).

Scheme 5. Preparation of two-carbon linked dimer analogs from dimer ketone 24.

Scheme 5a

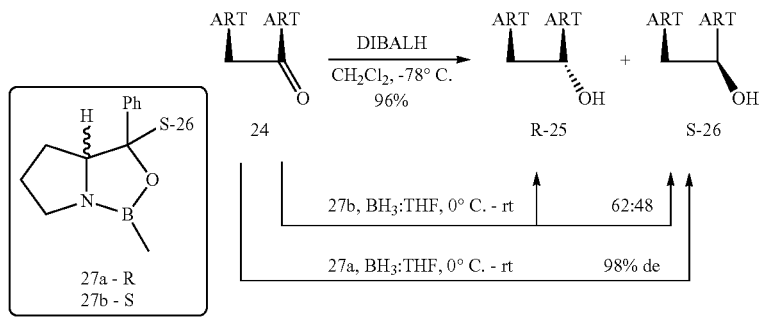

Scheme 5b

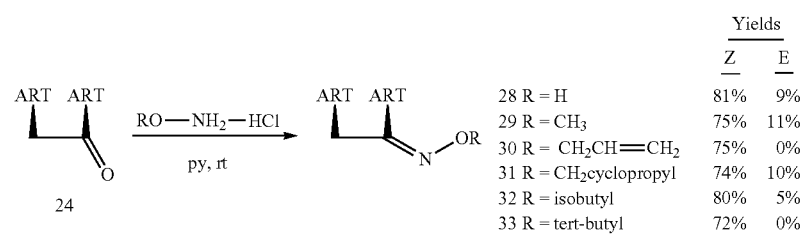

Scheme 5c

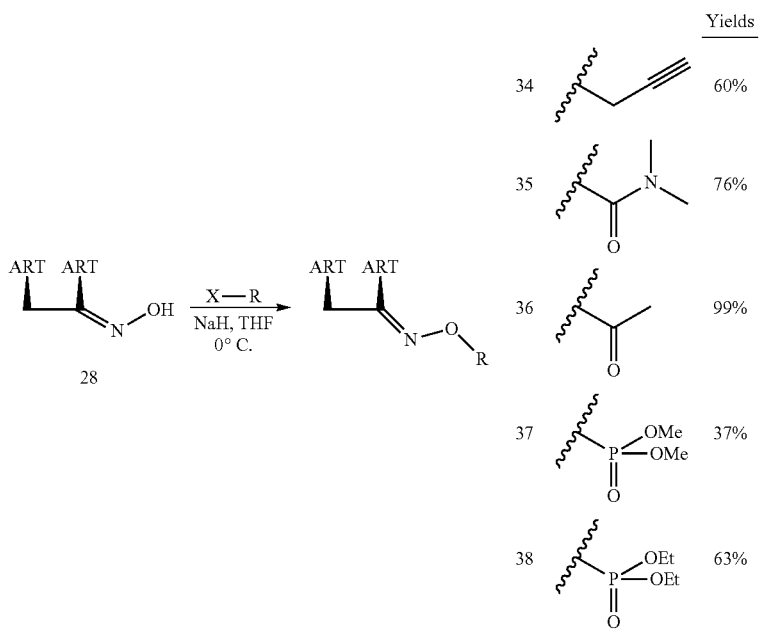

Stereochemistry

Synthesis of the two-carbon linked dimer and its derivatives generates several stereochemical questions. Reduction of artemisinin at low temperatures leads exclusively to products with α-stereochemistry, Haynes, et al., 2002, as described in the synthesis of α-2,4-dimethoxybenzoate intermediate 20 and DHA-OAc 19. Furthermore, nucleophilic displacement on these analogs has been shown to produce exclusively products with β-configuration, Pu and Ziffer, 1995, and Ma, et al., 2000, Posner, et al., 1999, Haynes, et al., 2002, as demonstrated in the synthesis of C10 β-alkyne 21. The proton NMR coupling constants between the C9/C10 protons are indicative of the stereochemistry at this location, as α-products position these protons in an axial-axial orientation resulting in larger coupling constants. Karplus, 1959. For example, the C9/C10 coupling constant for α-20 (protons are trans-diaxial) is 9.8 Hz but for β-21 (protons are axial-equatorial) it is 5.7 Hz (see Table 3). The C5 proton is affected by C10 stereochemistry, as well. Conversion of C10-α-benzoate 20 to C10-β-alkyne 21 increases the chemical shift from 5.47 to 5.56 ppm, and it is hypothesized that the C5 proton is positioned to interact with the deshielded anisotropic cone of the alkyne in the β-orientation. Synthesis of the methyl ketone 22 should not change the C10 stereochemistry, and indeed the C9/C10 coupling constant and C5 chemical shift support this hypothesis ($J_{9,10}$=6.8 Hz; C5 δ=5.65 ppm). The C5 proton is further deshielded, likely due to hydrogen-bonding interactions with the carbonyl oxygen. While it could be possible to epimerize the C10 position upon reaction with LDA to produce TMS enol ether 23, the steric hindrance is likely too great. Proton NMR again confirms this hypothesis ($J_{9,10}$=6.4 Hz). Finally, reaction of TMS enol ether 23 with DHA-OAc 19 should produce the dimer ketone 24 with β-configuration at both C10 positions [referred to as C10 (adjacent to the carbonyl) and C10' (on the second artemisinin unit) in FIG. 5]. The chemical shifts and coupling constants for C10 and C10' were 4.84 ppm (J=6.3 Hz) and 4.57 (J=6.2 Hz), respectively, suggesting that both positions were in the β-configuration; this hypothesis was confirmed by X-ray crystallography (see FIG. 7). Interestingly, the C5 and C5' protons had very different chemical shifts—5.57 ppm and 5.30 ppm, respectively. This observation provides further evidence that the C5 proton is interacting with the carbonyl oxygen, an important observation for the oxime analogs (vide infra). Interestingly, the endoperoxides from both artemisinin units are exposed and locked on the outside of the caged structure, a feature that could be beneficial for activity of these two-carbon linked dimers.

Conversion of the ketone 24 into the various oximes 28-33 raised an additional stereochemical question. The conditions employed could form either the E- or Z-isomer, and also could epimerize the C10 position (because it is alpha to the carbonyl). The synthesis of each oxime from ketone 24 generally formed one major product (yields shown in FIG. 5b, the less polar product by analytical TLC), and in some cases one minor product (yields shown in FIG. 5b, the more polar spot by analytical TLC). First, it should be noted that in all cases the C9-10 and C9'-10' coupling constants are ~6 Hz, suggesting that the α-stereochemistry has been maintained at both positions. The C5 and C5' and the C10 and C10' protons from each molecule were again of interest. For example, the chemical shifts of the C5 and C5' protons for the less polar oxime (Z-28) are 5.39 ppm and 5.37 ppm, respectively, and the C10 and C10' protons are 5.68 ppm (J=6.9 Hz) and 4.53 ppm (J=5.9 Hz), respectively. The observation that the C5 proton is no longer deshielded suggests that the less polar compound is the Z-isomer—the hydroxyl group would be on the same side of the artemisinin unit, and the steric clash would force the C10-oxime bond to rotate out, thereby avoiding the interaction of the oxime nitrogen with the C5 proton (see FIG. 6a). Furthermore, the C10 proton is drastically deshielded, shifting from 4.84 ppm in the starting ketone to 5.68 ppm. This observation suggests that the hydroxyl group is positioned to interact with the C10 proton. Conversely, the chemical shifts of the C5 and C5' protons for the more polar oxime (minor product E-28) are 5.50 ppm and 5.43 ppm, respectively, and the C10 and C10' were 5.17 ppm (J=6.3 Hz) and 4.59 ppm (J=6.3 Hz), respectively. In this polar isomer, the C10 and C10' protons are both deshielded, which could be explained by interaction with the oxime nitrogen (for C10) and possibly the hydroxyl group (for C10'). This would be indicative of the E-isomer (see FIG. 6b). The chemical shift trends for C5, C5', C10, and C10' are consistent for both the major and the minor isomers across the remainder of the oxime analogs (see Table 3), suggesting that each major product has the same configuration (and conversely, each minor product, as well). Ideally, these results will be confirmed by X-ray crystallography.

Example 2

Representative Biological Data

In Vivo Studies

Nearly all of the two-carbon linked dimer analogs were evaluated in *Plasmodium berghei* infected mice using a 60-day survival study. Each trioxane (0.64 mg) and mefloquine hydrochloride (1.92 mg) were dissolved in 100 μL of 7:3 Tween:EtOH mixture, and the mixture was further diluted with 965 μL of water (total volume of 1065 μL). Twenty-four hours after infection with *P. berghei* ANKA strain (2×10⁷ parasitized erythrocytes), each of four 5-week old C57BL/6J mice (Jackson Laboratory, weighing approximately 20 g each) received 200 μL of the trioxane solution via oral gavage, corresponding to a dose of 6 mg/kg of trioxane and 18 mg/kg of mefloquine hydrochloride. Blood parasitemia levels and duration of animal survival as compared to survival time of animals receiving no drug were monitored, both being widely accepted measures of a drug's antimalarial efficacy. A select set were tested in the initial experiment, and these results are summarized in Table 1.

The data in this study demonstrate the overall high efficacy of this class of compounds. Mice receiving the drug artemether (4b) in combination with mefloquine survived an average of 40.0 days. Nearly all of the compounds tested were definitively more efficacious, with two compounds (dimer methyl oxime Z-29 and dimer propargyl oxime 34) achieving complete cures of all four mice. The cured mice gained an average of 10.7 grams and 12 g for dimer methyl oxime Z-29 and dimer propargyl oxime 34, respectively, as compared to an average of 7.7 gram for uninfected control mice receiving vehicle only, suggesting that the cured mice were exceptionally healthy. Another compound of note was dimer allyl oxime 30, which was tested both in combination with mefloquine and as a monotherapy (at 120 mg/kg, without mefloquine). The combination therapy was much more efficacious than artemether combined with mefloquine, extending the survival time to 56.0 days, while the monotherapy was equally as efficacious as artemether plus mefloquine.

TABLE 1

In Vivo Antimalarial Efficacy Using a Single Oral Dose of Trioxane Combined with Mefloquine Hydrochloride in *P. berghei* Infected Mice

| trioxane | single oral dose (mg/kg) trioxane | Mef-HCl | survival after infection (days) | avg | % parasitemia suppression[1] |
|---|---|---|---|---|---|
| trioxane | | | | | |
| 24 | 6 | 18 | 34, 39, 60, 60 | 48.3 | >99.9 |
| 28 | 6 | 18 | 30, 60, 60, 60 | 52.5 | >99.9 |
| Z-29 | 6 | 18 | 60, 60, 60, 60 | 60.0 | >99.9 |
| 30 | 6 | 18 | 44, 60, 60, 60 | 56.0 | >99.9 |
| 30 | 120 | 0 | 20, 21, 60, 60 | 40.3 | >99.9 |
| 34 | 6 | 18 | 60, 60, 60, 60 | 60.0 | >99.9 |
| 35 | 6 | 18 | 27, 60, 60, 60 | 51.8 | >99.9 |
| 36 | 6 | 18 | 13, 16, 20, 60 | 27.3 | >99.9 |
| 37 | 6 | 18 | 44, 60, 60, 60 | 56.0 | >99.9 |
| 38 | 6 | 18 | 16, 20, 30, 30 | 21.5 | >99.9 |
| controls: | | | | | |
| vehicle (no drug) | 0 | 0 | 6, 7, 8, 8 | 7.3 | 0 |
| artemether (4b) | 6 | 18 | 16, 24, 60, 60 | 40.0 | >99.9 |
| mefloquine | 0 | 18 | 17, 20, 20, 27 | 21.0 | >99.9 |

[1]determined on day 3 post infection

A second mouse experiment was initiated to further evaluate several of the lead compounds. An alternative adjuvant to establish a broader understanding of the efficacy of these compounds also was evaluated. As such, the lead compounds were screened in combination with lumefantrine and also as a monotherapy at 150 mg/kg. As summarized in Table 2, all of the lead compounds outperformed the drug artemether (4b), which prolonged survival to an average of 38.5 days and 19.0 days in combination with mefloquine and lumefantrine, respectively. One mouse receiving dimer methyl oxime Z-29 and mefloquine died early in the experiment (day 16) while the other three lived to day 60, an average of 49.0 days. Dimer methyl oxime Z-29 was, however, was marginally effective in combination with lumefantrine (26.3 day average) and not effective as a monotherapy, with an average survival time (8.3 days) similar to that of infected mice receiving no drug (8.8 days). Dimer allyl oxime 30 was efficacious in all three groups, extending survival time to 49.0 days, 41.3 days, and 46.8 days in combination with mefloquine, lumefantrine, or as a monotherapy, respectively. Dimer propargyl oxime 34 was once again the most potent compound. One mouse receiving mefloquine combination died at an extended time point (35 days) while the other three survived the entire 60 days, an average of 53.8 days. All four mice receiving lumefantrine combination survived the entire 60 days. These mice had gained as much weight as the uninfected control mice receiving vehicle only, again suggesting that the cured mice were healthy. The monotherapy dose prolonged survival time to 46.8 days, similar to that of dimer allyl oxime 30. Interestingly, the dimer tert-butyl oxime 33 was not very efficacious, prolonging survival to only 23.8 days. As the tert-butyl moiety would be less susceptible to metabolic oxidation (that would lead to subsequent conversion to the free oxime and ultimately to the ketone via hydrolysis), Venhuis, 2003, these data suggest that the oxime analogs may be acting as prodrugs.

TABLE 2

In Vivo Antimalarial Efficacy Using a Single Oral Dose of Trioxane Combined with Mefloquine Hydrochloride or Lumefantrine in *P. berghei* Infected Mice

| trioxane | single oral dose (mg/kg) trioxane | adjuvant | dose | survival after infection (days) | avg | % parasitemia suppression[1] |
|---|---|---|---|---|---|---|
| trioxane | | | | | | |
| E-29 | 6 | mefloquine | 18 | 16, 35, 37, 60 | 37.0 | >99.9 |
| Z-29 | 6 | mefloquine | 18 | 16, 60, 60, 60 | 49.0 | >99.9 |
| Z-29 | 6 | lumefantrine | 18 | 13, 16, 16, 60 | 26.3 | >99.9 |
| Z-29 | 150 | none | 0 | 7, 7, 9, 10 | 8.3 | 98 |
| 30 | 6 | mefloquine | 18 | 16, 60, 60, 60 | 49.0 | >99.9 |
| 30 | 6 | lumefantrine | 18 | 16, 29, 60, 60 | 41.3 | >99.9 |
| 30 | 150 | none | 0 | 7, 60, 60, 60 | 46.8 | >99 |
| 31 | 6 | mefloquine | 18 | 15, 29, 60, 60 | 41 | >99.9 |
| 33 | 6 | mefloquine | 18 | 18, 20, 20, 37 | 23.8 | >99.9 |
| 34 | 6 | mefloquine | 18 | 35, 60, 60, 60 | 53.8 | >99.9 |
| 34 | 6 | lumefantrine | 18 | 60, 60, 60, 60 | 60.0 | >99.9 |
| 34 | 6 | none | 18 | 7, 60, 60, 60 | 46.8 | >99.9 |
| controls: | | | | | | |
| vehicle (no drug) | 0 | | 0 | 6, 7, 7, 15 | 8.8 | 0 |
| artemether(4b) | 6 | mefloquine | 18 | 29, 29, 36, 60 | 38.5 | >99.9 |
| artemether(4b) | 6 | lumefantrine | 18 | 15, 16, 16, 29 | 19.0 | >99.9 |
| mefloquine | 0 | | 18 | 15, 16, 30, 31 | 23.0 | >99.9 |
| lumefantrine | 0 | | 18 | 7, 7, 7, 35 | 14.0 | >99.9 |

SUMMARY

Malaria remains an oppressive disease, especially in tropical regions. Drugs that have long term stability have been difficult to achieve due to the complexity of the parasitic life cycle coupled to the parasite's ability to develop resistance (particularly when exposed to sub-lethal doses). Artemisinin combination therapy has been a staple of chemotherapy over the past 20 years, but the poor properties of most artemisinin-derived drugs make them susceptible to rapid clearance and therefore reduced efficacy. Artemisinin-derived C10 carba analogs that might have improved physical properties to maintain an effective concentration in the blood stream are desired. This characteristic can be demonstrated by their efficacy in in vivo experiments as compared to the currently-used drug artmether (4b).

In some embodiments, the presently disclosed subject matter provides the synthesis and biological evaluation of a new series of artemisinin-derived two-carbon linked dimers, whose unique conformation places the endoperoxides of each artemisinin unit (necessary for biological activity) on the outside of a caged structure. This two-carbon linked dimer system has been further functionalized into a series of oxime derivatives in an effort to improve their behavior in vivo. Many of the presently disclosed dimers are much more efficacious than artemether (4b). In particular, the propargyl oxime 34 achieved a complete cure in two separate experiments, and in combination with two different adjuvants (mefloquine and lumefantrine). The average survival time of all mice receiving this new compound was significantly higher (55.1 days) than the survival time of all mice receiving artmether combination therapy (31.7 days). The efficient synthesis of these compounds and their highly efficacious biological activity make especially the curative propargyl oxime 34 a leading candidate for further drug development.

Example 3

Experimental Methods and Analytical Data

Experimental Methods

All reactions were performed under argon in oven-dried or flame-dried glassware. Microwave reactions were performed in a Biotage Initiator microwave. Dichloromethane was dispensed from an LC Technology Solutions SPBT-1 bench top solvent purification system. All commercially available reagents were purchased from Sigma Aldrich and used as received. All experiments were monitored by analytical thin layer chromatography (TLC) performed on Silicycle silica gel 60 Å glass supported plates with 0.25-mm thickness. Flash chromatography was performed with EMD silica gel (40-63 μM). Automated purification was performed on a Teledyne Isco CombiFlask $R_f$ purification system (referred to as "Isco") using Teledyne RediSef $R_f$ Gold High Performance pre-packed silica columns. Yields are not optimized. Infrared (IR) spectra were recorded on a Perkin Elmer 1600 FT-IR spectrometer. Nuclear magnetic resonance (NMR) spectra were recorded on a Bruker Avance 400 MHz FT-NMR spectrometer (400 MHz for $^1$H, 100 MHz for $^{13}$C). The following abbreviations are used in the experimental section for the description of $^1$H NMR spectra: singlet (s), doublet (d), triplet (t), quartet (q), multiplet (m), broad singlet (bs), doublet of doublets (dd), doublet of triplets (dt), and doublet of quartets (dq). Low resolution mass spectra (electrospray ionization) were acquired on an Agilent Technologies 6130 quadrupole spectrometer coupled to an Agilent Technologies 1200 series HPLC. High resolution mass spectrum-electron ionization spray (HRMS-ESI) were obtained on an Agilent Technologies 1200 series Dual Absorbance Detector HPLC system equipped with a Phenomenex Luna 75×3 mm, C18, 3 μm column at 45° C. (UV detection at 220 nm, BW 8 nm, and 254 nm BW 8 nm, flow rate: 0.8 mL/min (increasing), Injection volume: 1.0 μL, sample solvent: 100% Methanol, sample conc.: ~0.01 mg/mL, mobile phase A: Water with 0.1% acetic acid, mobile phase B: Acetonitrile with 0.1% acetic acid) coupled to a Agilent 6210 time-of-flight mass spectrometer (ion source: Duel ESI, min range: 115 m/z, max range: 1400 m/z, scan rate: 0.9 seconds, gas temp: 340° C., gas flow: 10 L/min, nebulizer: 50 PSI, ion polarity: positive, VCap: 3500 V, fragmentor: 175 V, skimmer 1: 65 V, OctopoleRFPeak: 250 V, ref mass: enabled (Agilent P/N G1969-85001). Data were analyzed using Agilent Masshunter Workstation Data Acquisition (v B.02.00, Patch 1,2,3) and Agilent Masshunter Qualitative Analysis (v B.02.00, Build 2.0.197.7, Patch 3). List of abbreviations are as follows: dichloromethane—DCM; dimethylformamide—DMF; sat. aq. NaCl—brine; ethyl acetate—EtOAc; room temperature—RT; brsm—based on recovered starting material.

Synthesis of C10-α-2,4-dimethoxybenzoate 20

To a 100 mL round bottom flask were added artemisinin (300 mg, 1.06 mmol, 1.0 eq) and $CH_2Cl_2$ (10 mL). The stirring solution was cooled to −78° C. for 20 min, at which time diisobutylaluminum hydride (DIBALH, 1.0 M in $CH_2Cl_2$, 1.275 mL, 1.27 mmol, 1.2 eq) was added dropwise over 15 min. The reaction mixture was stirred at −78° C. for 2 h (until complete consumption of starting material was seen by TLC). At that time, N,N-dimethylaminopyridine (DMAP, 143 mg, 1.17 mmol, 1.1 eq) and pyridine (py, 0.5 mL, 6.38 mmol, 6 eq) were added, followed by 2,4-dimethoxybenzoyl chloride (1.07 mg, 5.31 mmol, 5 eq). The resulting reaction mixture was allowed to gradually warm to rt and stirred overnight. Upon completion, the reaction was quenched with sat. aq. $NH_4Cl$ and diluted with EtOAc. The organic layer was washed again with sat. aq. $NH_4Cl$ and brine, then extracted, dried on $MgSO_4$, filtered, and the solvent was removed under reduced pressure. The residue was purified directly on silica. Gradient elution (10-35% ethyl acetate in hexanes) afforded the desired product as a colorless solid: yield (421 mg, 88%); m.p. −127.8° C.; $^1$H NMR (400 MHz, $CDCl_3$) δ 7.96-7.94 (d, 1H, J=8.6 Hz), 6.47-6.43 (m, 2H), 5.97-5.95 (d, 1H, J=9.8 Hz), 5.47 (s, 1H), 3.85 (s, 3H), 3.83 (s, 3H), 2.72-2.63 (m, 1H), 2.40-2.31 (m, 1H), 2.04-1.98 (m, 1H), 1.91-1.83 (m, 1H), 1.81-1.68 (m, 2H), 1.67-1.60 (m, 1H), 1.54-1.43 (m, 2H), 1.40 (s, 3H), 1.34-1.25 (m, 2H), 1.15-0.88 (m, 7H); $^{13}$C NMR (100 MHz, $CDCl_3$) δ 164.5, 161.9, 134.5, 104.3, 98.8, 91.8, 91.5, 80.2, 55.8, 55.5, 52.9, 51.7, 45.4, 41.1, 37.2, 36.3, 34.1, 32.0, 25.9, 24.6, 22.0, 20.2, 12.2; HRMS (FAB) m/z for $C_{24}H_{33}O_8$ $(M+H)^+$ calc.=449.2175. Found=449.2169; $[\alpha]_D^{23}$=+26.27 (c=0.645, $CHCl_3$); IR (thin film) 3010, 2939, 2876, 1732, 1652, 1608, 1575, 1558, 1540, 1506, 1457, 1418, 1375, 1330, 1267, 1248, 1211, 1164, 1131, 1107, 1086, 1030, 1016, 942, 926, 878, 861, 830, 752 $cm^{-1}$.

Synthesis of β-C10-acetylene 21

To a 100 mL round bottom flask were added 20 (67 mg, 0.15 mmol, 1.0 eq) and $Et_2O$ (30 mL). The slurry was stirred at rt for 10 min until complete dissolution was achieved, and the stirring solution was subsequently cooled to 0° C. After 10 min, zinc(II) chloride ($ZnCl_2$, 1.0M in $Et_2O$, 0.149 mL, 0.15 mmol, 1.0 eq) and ethynyl magnesium bromide (0.5M in THF, 1.195 ml, 0.6 mmol, 4.0 eq) were added dropwise simultaneously from separate syringes. The reaction mixture was stirred at 0° C. for 3 h, and then gradually warmed to rt as the ice bath melted and stirred overnight. Upon completion, the reaction was quenched with $H_2O$ and diluted with EtOAc. The organic layer was washed with sat. aq. $NH_4Cl$ and brine, then extracted, dried on $MgSO_4$, filtered, and the solvent was removed under reduced pressure. The residue was purified directly on silica. Gradient elution afforded the desired product as a white solid: yield (21 mg, 48%), m.p. −121.6° C., $^1H$ NMR (400 MHz, $CDCl_3$) δ 5.56 (s, 1H), 4.74-4.72 (dd, 1H, J=2.5, 5.8 Hz), 2.81-2.70 (m, 1H), 2.53-2.52 (d, 1H, J=2.5 Hz), 2.41-2.30 (m, 1H), 2.24-2.00 (m, 2H), 1.92-1.83 (m, 1H), 1.79-1.62 (m, 2H), 1.59-1.48 (m, 2H), 1.42 (s, 3H), 1.39-1.20 (m, 3H), 1.00-0.85 (m, 7H); $^{13}C$ NMR (100 MHz, $CDCl_3$) δ 104.2, 89.4, 81.4, 80.8, 77.2, 67.1, 52.6, 45.3, 37.3, 36.2, 34.5, 29.8, 26.0, 24.6, 22.9, 20.3, 13.7; HRMS (FAB) m/z for HRMS (FAB) m/z for $C_{17}H_{25}O_4$ $(M+H)^+$ calc.=293.1747. Found=293.1744; $[α]_D^{23}$=+112.57 (c=0.390, $CHCl_3$); IR (thin film) 2942, 2871, 1506, 1450, 1208, 1136, 1122, 1088, 1055 cm$^{-1}$.

Synthesis of Artemisinin Monomer Methyl Ketone 22

To a round bottom flask were added monomer acetylene 21 (695 mg, 2.38 mmol, 1.0 eq), water ($H_2O$, 200 µL, 5.0 eq) and acetone (15 mL). para-Toluenesulfonic acid (pTsOH, 597 mg, 1.0 eq) and mercuric acetate ($Hg(OAc)_2$, 547 mg, 0.7 eq) were added to the stirring solution, and the resulting slurry was stirred at rt overnight. Upon completion the reaction mixture was filtered through a short pad of celite and concentrated in vacuo. The residue was purified directly on the Isco Combiflash automated purification system. Gradient elution (0 to 40% ethyl acetate in hexanes) afforded the desired product as a colorless oil: yield (650 mg, 88%,); $^1H$ NMR (300 MHz, $CDCl_3$) δ 5.65 (s, 1H), 4.75 (d, J=6.78 Hz, 1H), 2.93 (ddd, J=14.03, 7.54, 6.50 Hz, 1H), 2.38-2.24 (m, J=13.23, 10.69, 3.91, 3.91, 3.91 Hz, 1H), 2.21 (s, 3H), 2.08-1.98 (m, 1H), 1.98-1.87 (m, 1H), 1.76-1.70 (m, 1H), 1.70-1.65 (m, 2H), 1.65-1.60 (m, 1H), 1.52-1.43 (m, 1H), 1.40 (s, 3H), 1.38-1.31 (m, 1H), 1.31-1.24 (m, 2H), 1.24-1.15 (m, 1H), 1.02 (d, J=7.68 Hz, 3H), 0.95 (d, J=5.98 Hz, 3H); $^{13}C$ NMR (100 MHz, $CDCl_3$) δ 210.2, 103.2, 90.1, 80.9, 79.9, 51.8, 44.2, 37.3, 36.4, 34.1, 30.0, 28.8, 25.9, 24.7, 23.7, 20.0, 13.5; ESI-HRMS m/z $(M+H)^+$ for $C_{17}H_{27}O_5$ calc. 311.1853. Found=311.1854; FT-IR (cm$^{-1}$) 2930, 2874, 1783, 1711, 1672, 1566, 1548, 1532, 1526, 1514, 1457, 1430, 1366, 1279, 1196, 1102, 1062, 1012, 957, 931, 883; $[α]_D^{25}$+70.37 (c=0.18, $CHCl_3$).

Synthesis of Artemisinin Monomer Trimethylsilyl Enol Ether 23

To a round bottom flask were added artemisinin monomer methyl ketone 22 (50 mg, 0.16 mmol, 1.0 eq) and THF (5 mL), and the stirring solution was cooled to −78° C. Triethylamine ($Et_3N$, 0.045 mL, 0.32 mmol, 2.0 eq) and trimethylsilyl trifluoromethanesulfonate (TMSOTf, 0.058 mL, 0.32 mmol, 2.0 eq) were added, and the reaction mixture was stirred at −78° C. for 30 min before warming to rt. Upon completion, the reaction was quenched with sat. aq. $NaHCO_3$ and the product was extracted with EtOAc. The organic layer was washed with brine, dried over $Na_2SO_4$, filtered, and conc in vacuo. The residue was purified directly on silica gel. Gradient elution (0-5% EtOAc in hexanes) afforded the desired compound as a colorless oil: yield (55 mg, 89%); $^1H$ NMR (400 MHz, $CDCl_3$) δ 5.57 (s, 1H), 4.54 (d, J=6.32 Hz, 1H), 4.37 (s, 1H), 4.14 (s, 1H), 2.83-2.65 (m, 1H), 2.29 (dt, J=3.92, 13.96 Hz, 1H), 2.02-1.92 (m, 1H), 1.87 (tdd, J=3.41, 6.32, 13.64 Hz, 1H), 1.70-1.47 (m, 4H), 1.42-1.34 (m, 5H), 1.30-1.15 (m, 2H), 0.91 (d, J=6.57 Hz, 6H), 0.18 (s, 9H); $^{13}C$ NMR (100 MHz, $CDCl_3$) δ 157.3, 103.1, 90.3, 89.6, 81.1, 74.7, 52.1, 44.4, 37.4, 36.5, 34.3, 26.0, 24.8, 23.3, 20.1, 13.9, 0.1.

Synthesis of dihydroartemisinin acetate 19 has been previously reported. Moon, et al., 2011; Paik et al., 2006; Rosenthal, et al., 2009; and Woodard, et al., 2009.

Synthesis of Artemisinin Two-Carbon Linked Dimer Ketone 24

To a round bottom flask were added artemisinin monomer trimethylsilyl enol ether 23 (36.5 mg, 0.095 mmol, 1.0 eq), dihydroartemisinin acetate 19 (31.0 mg, 0.095 mmol, 1.0 eq) and dichloromethane ($CH_2Cl_2$, 1 mL). The stirring solution was cooled to −78° C., and after 10 min tin IV chloride ($SnCl_4$, 1.0 M in $CH_2Cl_2$, 0.095 mL, 0.095 mmol, 1.0 eq, further diluted to 1 mL) was added in one portion. The reaction mixture was stirred at −78° C. for 2 h. Analytical TLC showed 9,10-olefin (elimination product), artemisinin monomer methyl ketone (either residual from TMS enol ether starting material or unreacted enolate), and two new spots (one of which was desired product, the other has yet to be identified). The reaction was quenched with water and the products were extracted with $CH_2Cl_2$. The organic layer was washed with brine, dried, filtered, and concentrated under reduced pressure. The residue was purified directly on Isco. Gradient elution (0-15% ethyl acetate in hexanes) afforded the desired product as a colorless solid: yield (30 mg, 55%); $^1H$ NMR (300 MHz, $CDCl_3$) δ 5.57 (s, 1H), 5.30 (s, 1H), 4.84 (ddd, J=9.51, 6.17, 3.81 Hz, 1H), 4.57 (d, J=6.31 Hz, 1H), 3.18 (dd, J=15.82, 9.09 Hz, 1H), 2.99-2.85 (m, J=13.61, 7.58, 7.58, 6.03 Hz, 1H), 2.76 (dt, J=13.70, 7.35, 6.36 Hz, 1H), 2.39 (dd, J=15.71, 3.74 Hz, 1H), 2.35-2.25 (m, 2H), 2.07-2.02 (m, 1H), 2.02-1.95 (m, 1H), 1.94-1.83 (m, 2H), 1.82-1.72 (m, 2H), 1.72-1.62 (m, 3H), 1.61-1.55 (m, 2H), 1.53-1.43 (m, 1H), 1.41 (s, 3H), 1.37 (s, 3H), 1.36-1.32 (m, 1H), 1.31-1.26 (m, 2H), 1.23 (d, J=5.79 Hz, 2H), 1.21-1.15 (m, 1H), 1.10 (d, J=7.68 Hz, 3H), 0.95 (d, J=5.98 Hz, 3H), 0.92 (d, J=6.26 Hz, 4H), 0.84 (d, J=7.49 Hz, 3H); $^{13}C$ NMR (100 MHz, $CDCl_3$) δ 211.9, 103.5, 103.2, 90.2, 88.9, 80.9, 80.8, 80.1, 71.6, 52.3, 52.1, 44.6, 44.3, 40.0, 37.5, 36.9, 36.5, 36.4, 34.4, 34.3, 30.6, 29.9, 25.9, 25.9, 24.7, 24.6, 23.9, 20.1, 13.7, 13.4; ESI-HRMS m/z $(M+Na)^+$ for $C_{32}H_{48}O_9Na$ calc. 599.3191. Found=99.3184; $[α]_D^{25}$+93.98 (c=0.26, $CHCl_3$); FT-IR (cm$^{-1}$) 2937, 2872, 1712, 1651, 1549, 1532, 1525, 1514, 1457, 1194, 1098, 1053, 1018, 941, 876, 829, 753.

Synthesis of Dimer Alcohols 25 and 26

To a round bottom flask were added dimer ketone 3 (76.8 mg, 0.13 mmol, 1.0 eq) and dichloromethane ($CH_2Cl_2$, 3 mL). The stirring solution was cooled to −78° C. in a dry ice:acetone bath. Diisobutylaluminum hydride (DIBALH, 146 µL, 0.15 mmol, 1.1 eq) was added, and the reaction mixture was stirred at −78° C. for 2.5 h. The diasteromeric alcohols 25 and 26 are easily visualized via analytical TLC (note—the stereochemical assignment is currently ambiguous). Upon completion, the reaction mixture was quenched with sat. aq. $NH_4Cl$. The products were extracted with $CH_2Cl_2$, and the organic layers were pooled and washed with brine, then dried over $Na_2SO_4$. The solution was filtered and the solvent was removed under reduced pressure and the residue was purified directly on the Isco Combiflash automated purification system. Gradient elution (0 to 40% ethyl acetate in hexanes) afforded the desired products as colorless amorphous solids: yield (35.5 mg 25, 92%; $^1H$ NMR (300 MHz, $CDCl_3$) δ 5.37 (s, 1H), 5.30 (s, 1H), 4.73 (dd, J=10.93, 6.19 Hz, 1H), 4.49 (dd, J=9.66, 5.94 Hz, 1H), 4.00-3.91 (m, 1H), 3.09 (d, J=7.20 Hz, 1H), 2.73-2.56 (m, 2H), 2.37-2.25 (m, J=13.76, 13.76, 6.90, 3.92 Hz, 2H), 2.17-2.08 (m, 1H), 2.03 (d, J=4.17 Hz, 1H), 2.02-1.98 (m, 1H), 1.98-1.86 (m, 2H), 1.85-1.76 (m, 3H), 1.73-1.66 (m, 2H), 1.65-1.58 (m, 2H), 1.49-1.42 (m, 1H), 1.42-1.36 (m, 7H), 1.36-1.28 (m, 2H), 1.28-1.17 (m, 4H), 1.04 (d, J=7.45 Hz, 3H), 0.99-0.93 (m, 7H), 0.93-0.87 (m, 4H); $^{13}C$ NMR (100 MHz, $CDCl_3$) δ 103.2, 102.1, 90.9, 88.9, 81.1, 80.8, 71.8, 71.5, 52.3, 51.6, 44.3, 43.2, 37.5, 37.4, 36.7, 36.5, 34.5, 34.3, 31.2, 30.2, 29.4, 25.9, 25.1, 24.9, 24.8, 24.7, 20.2, 20.0, 12.9, 11.6; ESI-HRMS m/z $(M+Na)^+$ for $C_{32}H_{50}NaO_9$ calc. 601.3347. Found=601.3342; yield (35.2 mg 26, 91%); $^1H$ NMR (300 MHz, $CDCl_3$) δ 5.54 (s, 1H), 5.40 (s, 1H), 4.40 (ddd, J=11.21, 6.13, 1.42 Hz, 1H), 4.24 (dd, J=6.73, 3.63 Hz, 1H), 3.98-3.89 (m, 1H), 3.29 (d, J=1.64 Hz, 1H), 2.76-2.65 (m, 1H), 2.66-2.55 (m, 1H), 2.38-2.24 (m, 2H), 2.09-1.98 (m, 3H), 1.97-1.85 (m, 2H), 1.82-1.73 (m, 1H), 1.72-1.65 (m, 2H), 1.65-1.62 (m, 2H), 1.62-1.54 (m, 2H), 1.54-1.42 (m, 2H), 1.42-1.35 (m, 7H), 1.35-1.28 (m, 2H), 1.28-1.19 (m, 3H), 0.97 (d, J=7.64 Hz, 3H), 0.95 (d, J=6.19 Hz, 7H), 0.86 (d, J=7.52 Hz, 4H); $^{13}C$ NMR (100 MHz, $CDCl_3$) δ 103.3, 102.4, 90.9, 88.8, 81.3, 81.0, 75.6, 74.4, 71.2, 52.3, 51.8, 44.3, 43.7, 37.3, 37.2, 36.6, 36.5, 34.4, 34.3, 34.2, 30.3, 30.1, 25.9, 24.8, 24.6, 24.1, 20.2, 20.0, 13.2, 13.0; ESI-HRMS m/z $(M+Na)^+$ for $C_{32}H_{50}NaO_9$ calc. 601.3347. Found=601.3344.

Stereoselective Synthesis of Dimer Alcohol S-26

To a 1 dram vial were added dimer ketone 24 (5 mg, 0.01 mmol, 1.0 eq) and THF (0.5 mL). The stirring solution was cooled to 0° C., and (R)-(+)-2-methyl-CBS oxazaborolidine (R-27, 1.0 M in THF, 0.01 mL, 1.2 eq) and borane ($BH_3$, 1.0 M in THF, 0.01 mL, 1.2 eq) were added. The reaction mixture was warmed to rt and quenched with $H_2O$ after 1 h. The product was extracted with EtOAc, and the organic layer was dried over $Na_2SO_4$, filtered, and concentrated under reduced pressure. The residue was purified as described above, providing the desired product S-26. All spectral data matched the data provided above.

Synthesis of Dimer Oxime 28

To a round bottom flask were added dimer ketone 24 (15.0 mg, 0.03 mmol, 1.0 eq), hydroxyl amine hydrochloride (9.0 mg, 0.13 mmol, 5.0 eq), and pyridine (1 mL). The reaction mixture was stirred at rt overnight. Upon completion, as detected by analytical TLC, the reaction mixture was diluted with EtOAc and organic layer was washed twice with 10% citric acid. The aqueous layer was back extracted with EtOAc and the organic layers were pooled and washed with brine. The solvent was removed under reduced pressure and the residue was purified directly on silica gel. Gradient elution (0 to 40% ethyl acetate in hexanes) afforded the desired product as a colorless amorphous solid: yield (12.5 mg, 81%);

$^1H$ NMR (300 MHz, $CDCl_3$) δ 5.68 (d, J=6.90 Hz, 1H), 5.39 (s, 1H), 5.37 (s, 1H), 4.53 (ddd, J=9.13, 5.91, 3.30 Hz, 1H), 3.48 (s, 1H), 2.92 (sxt, J=7.68 Hz, 1H), 2.82 (dd, J=13.40, 7.48 Hz, 1H), 2.54 (dd, J=14.62, 9.15 Hz, 1H), 2.45 (dd, J=14.67, 3.33 Hz, 1H), 2.37-2.24 (m, 2H), 2.04-2.01 (m, 1H), 2.01-1.94 (m, 2H), 1.91-1.81 (m, 2H), 1.81-1.77 (m, 1H), 1.77-1.74 (m, 1H), 1.74-1.69 (m, 1H), 1.68-1.65 (m, 1H), 1.65-1.61 (m, 1H), 1.57-1.51 (m, 1H), 1.51-1.44 (m, 1H), 1.44-1.39 (m, 4H), 1.39-1.36 (m, 3H), 1.36-1.29 (m, 2H), 1.29-1.24 (m, 3H), 1.24-1.19 (m, 1H), 0.98-0.93 (m, 7H), 0.91 (d, J=7.48 Hz, 4H), 0.81 (d, J=7.63 Hz, 3H); $^{13}C$ NMR (100 MHz, $CDCl_3$) δ 159.9, 103.4, 102.3, 90.4, 88.3, 81.1, 80.7, 74.1, 74.1, 69.6, 52.7, 51.2, 44.8, 43.2, 37.6, 37.3, 36.7, 36.6, 34.6, 34.2, 30.3, 29.5, 29.1, 26.1, 25.8, 25.1, 24.8, 24.6, 20.4, 19.9, 13.6, 12.7; ESI-HRMS m/z $(M+H)^+$ for $C_{32}H_{50}NO_9$ calc. 592.3480. Found=592.3480; FT-IR $(cm^{-1})$ 3412, 2968, 2942, 2874, 1660, 1453, 1376, 1204, 1123, 1091, 1054, 1011, 977, 946, 879, 754; $[\alpha]_D^{25}$+45.69 (c=0.625, $CHCl_3$).

Synthesis of Dimer O-Methyl Oxime 29

The desired compound was prepared in a similar manner to dimer oxime 28 as described above, substituting O-methyl hydroxylamine hydrochloride for hydroxylamine hydrochloride. Gradient elution on silica gel (0 to 40% ethyl acetate in hexanes) afforded the desired product as a colorless amorphous solid: yield (11.9 mg, 75%; $^1H$ NMR (300 MHz, $CDCl_3$) δ 5.56 (d, J=6.94 Hz, 1H), 5.41 (s, 1H), 5.35 (s, 1H), 4.55 (ddd, J=8.93, 5.89, 3.23 Hz, 1H), 3.83 (s, 3H), 3.49 (s, 1H), 2.89-2.77 (m, 2H), 2.55 (dd, J=14.57, 9.00 Hz, 1H), 2.41 (dd, J=14.48, 3.23 Hz, 1H), 2.31 (qd, J=14.04, 4.38 Hz, 2H), 2.04-2.01 (m, 1H), 2.01-1.97 (m, 1H), 1.97-1.93 (m, 1H), 1.91-1.83 (m, 1H), 1.83-1.77 (m, 1H), 1.77-1.72 (m, 1H), 1.72-1.68 (m, 1H), 1.68-1.61 (m, 4H), 1.58-1.53 (m, 1H), 1.53-1.48 (m, 1H), 1.48-1.41 (m, 1H), 1.40 (s, 3H), 1.38 (s, 3H), 1.37-1.30 (m, 3H), 1.30-1.21 (m, 4H), 0.95 (dd, J=5.97, 3.23 Hz, 7H), 0.92 (d, J=7.48 Hz, 4H), 0.77 (d, J=7.63 Hz, 3H); $^{13}C$ NMR (100 MHz, $CDCl_3$) δ 158.8, 103.3, 102.3, 90.3, 88.4, 81.1, 80.7, 74.2, 70.0, 61.6, 52.7, 51.2, 44.9, 43.2, 37.5, 37.3, 36.7, 36.6, 34.6, 34.3, 30.4, 30.0, 29.1, 26.1, 25.8, 25.0 24.7, 24.7, 24.6, 20.3, 19.9, 13.6, 12.7; ESI-HRMS m/z $(M+H)^+$ for $C_{33}H_{52}NO_9$ calc. 606.3637. Found=606.3636.

Synthesis of 2C-dimer O-allyl oxime 30

The desired compound was prepared in a similar manner to dimer oxime 28 as described above, substituting O-allyl hydroxylamine hydrochloride hydrate for hydroxylamine hydrochloride. The crude product consisted of a single oxime diastereomer. Gradient elution on silica gel (0 to 40% ethyl acetate in hexanes) afforded the desired diastereomerically pure product as a colorless amorphous solid: yield (8.2 mg, 75%); $^1H$ NMR (300 MHz, $CDCl_3$) δ 6.04-5.91 (m, J=15.99, 10.61, 6.75, 5.43, 5.43, 5.18 Hz, 1H), 5.63 (d, J=6.85 Hz, 1H), 5.40 (s, 1H), 5.36 (s, 1H), 5.26 (dd, J=17.31, 1.71 Hz, 1H), 5.13 (dd, J=10.37, 1.52 Hz, 1H), 4.62-4.52 (m, 2H), 2.94-2.75 (m, 2H), 2.55 (dd, J=14.67, 8.51 Hz, 1H), 2.46 (dd, J=14.67, 3.91 Hz, 1H), 2.38-2.24 (m, J=13.98, 13.98, 13.73, 4.38 Hz, 2H), 2.05-1.94 (m, 3H), 1.92-1.84 (m, 1H), 1.83-1.76 (m, 1H), 1.76-1.69 (m, 2H), 1.69-1.60 (m, 3H), 1.59-1.50 (m, 1H), 1.50-1.41 (m, 1H), 1.39 (d, J=4.99 Hz, 6H), 1.36-1.30 (m, 2H), 1.30-1.19 (m, 3H), 0.96 (d, J=3.57 Hz, 3H), 0.95 (d, J=4.11 Hz, 3H), 0.91 (d, J=7.48 Hz, 3H), 0.79 (d, J=7.63 Hz, 2H); $^{13}C$ NMR (100 MHz, $CDCl_3$) δ 159.1, 134.8, 116.5, 103.3, 102.2, 90.4, 90.4, 88.6, 88.5, 81.1, 80.7, 74.6, 73.9, 70.0, 52.6, 51.2, 44.9, 43.2, 37.6, 37.3, 36.7, 36.6, 34.6, 34.3, 30.3, 30.1, 29.2, 26.1, 25.7, 25.1, 24.7, 20.3, 19.9, 13.5, 12.7; ESI-HRMS m/z $(M+H)^+$ for $C_{35}H_{54}NO_9$ calc. 632.3793. Found=632.3797; FT-IR (cm$^{-1}$) 2991, 2969, 2920, 1665, 1454, 1376, 1114, 1092, 1056, 1011, 983, 945, 880, 755; $[\alpha]_D^{25}$+50.15 (c=0.40, CHCl$_3$).

Synthesis of dimer O-methylcyclopropyl oxime 31

The desired compound was prepared in a similar manner to dimer oxime 28 as described above, substituting O-methylcyclopropyl hydroxylamine hydrochloride for hydroxylamine hydrochloride. Gradient elution on silica gel (0 to 40% ethyl acetate in hexanes) afforded the desired diastereomerically pure product as a colorless amorphous solid: yield (9.9 mg, 74%);

Synthesis of dimer O-isobutyl oxime 32

The desired compound was prepared in a similar manner to dimer oxime 28 as described above, substituting 0-isobutyl hydroxylamine hydrochloride for hydroxylamine hydrochloride. The crude product consisted of a single oxime diastereomer. Gradient elution on silica gel (0 to 40% ethyl acetate in hexanes) afforded the desired diastereomerically pure product as a colorless amorphous solid: yield (10.8 mg, 80%);

Synthesis of dimer O-isobutyl oxime 33

The desired compound was prepared in a similar manner to dimer oxime 28 as described above, substituting 0-tert-butyl hydroxylamine hydrochloride for hydroxylamine hydrochloride. The crude product consisted of a single oxime diastereomer. Gradient elution on silica gel (0 to 40% ethyl acetate in hexanes) afforded the desired diastereomerically pure product as a colorless amorphous solid: yield (10.5 mg, 72%);

Synthesis of dimer propargyl oxime 34

To a 1 dram vial were added dimer oxime 28 (4.8 mg, 0.01 mmol, 1.0 eq) and tetrahydrofuran (THF, 1 mL). The stirring solution was cooled to 0° C. in an ice bath, and sodium hydride (NaH, 0.3 mg, 1.5 eq) was added as a dry powder, and the reaction mixture was stirred for 20 min. At that time, propargyl bromide (2 μL, 1.5 eq) was added and the reaction mixture was stirred overnight, gradually warming to room temperature. Upon completion the reaction mixture was quenched with water and diluted with EtOAc. The organic layer was washed with sat. aq. NH$_4$Cl and brine, extracted, dried over Na$_2$SO$_4$, filtered, and the solvent was removed under reduced pressure. The residue was purified directly on silica gel. Gradient elution (0 to 50% ethyl acetate in hexanes) afforded the desired product as a colorless amorphous solid: yield (4.1 mg, 60%); $^1$H NMR (300 MHz, CDCl$_3$) δ 5.60 (d, J=6.88 Hz, 1H), 5.41 (s, 1H), 5.36 (s, 1H), 4.71-4.60 (m, J=15.85, 3.47, 2.40, 2.40 Hz, 2H), 4.58 (td, J=5.73, 3.00 Hz, 1H), 2.95-2.78 (m, 2H), 2.58 (dd, J=14.53, 8.59 Hz, 1H), 2.51-2.44 (m, J=14.53, 3.66 Hz, 1H), 2.39 (t, J=2.40 Hz, 1H), 2.38-2.25 (m, J=14.04, 14.04, 13.77, 4.39 Hz, 2H), 2.07-1.94 (m, 2H), 1.93-1.85 (m, 1H), 1.85-1.78 (m, 1H), 1.78-1.70 (m, 1H), 1.70-1.65 (m, 1H), 1.65-1.59 (m, 4H), 1.59-1.49 (m, 2H), 1.48-1.42 (m, 1H), 1.40 (d, J=6.25 Hz, 7H), 1.38-1.30 (m, 4H), 1.30-1.20 (m, 3H), 0.97 (dd, J=6.03, 3.06 Hz, 7H), 0.93 (d, J=7.52 Hz, 4H), 0.82 (d, 3H); $^{13}$C NMR (100 MHz, CDCl$_3$) δ 160.4, 103.3, 102.3, 90.4, 88.5, 81.1, 80.7, 80.5, 74.0, 73.7, 70.0, 61.3, 52.6, 51.2, 44.9, 43.2, 37.6, 37.3, 36.7, 36.6, 34.6, 34.2, 30.3, 30.1, 29.2, 26.1, 25.7, 25.1, 24.7, 20.3, 19.9, 13.6, 12.7; ESI-HRMS m/z (M+H)$^+$ for $C_{35}H_{52}NO_9$ calc. 630.3637. Found=630.3613.

Synthesis of dimer oxime dimethylcarbamate 35

The desired compound was prepared in a similar manner to propargyl oxime 34 as described above, substituting dimethylcarbamyl chloride for propargyl bromide. Gradient elution on silica gel (10 to 100% ethyl acetate in hexanes) afforded the desired diastereomerically pure product as a colorless amorphous solid: yield (4.1 mg, 76%); $^1$H NMR (300 MHz, CDCl$_3$) δ 5.73 (d, J=6.88 Hz, 1H), 5.47 (s, 1H), 5.38 (s, 1H), 4.60-4.52 (m, 1H), 2.98 (s, 6H), 2.94-2.85 (m, 2H), 2.85-2.78 (m, 1H), 2.51 (dd, J=13.96, 2.27 Hz, 1H), 2.38-2.24 (m, 2H), 2.08-1.95 (m, 3H), 1.91-1.80 (m, 2H), 1.80-1.72 (m, 2H), 1.72-1.62 (m, 7H), 1.56-1.46 (m, 2H), 1.46-1.41 (m, 1H), 1.41-1.37 (m, 8H), 1.37-1.33 (m, 2H), 1.33-1.18 (m, 5H), 1.00-0.93 (m, 10H), 0.86 (d, J=7.64 Hz, 3H); $^{13}$C NMR (100 MHz, CDCl$_3$) δ 156.5, 155.3, 103.4, 102.4, 90.7, 88.3, 81.1, 80.7, 73.9, 70.4, 52.7, 51.1, 44.8, 43.2, 37.5, 36.6, 36.6, 36.0, 35.9, 34.5, 34.1, 30.5, 30.3, 30.1, 25.7, 24.9, 24.6, 24.6, 20.3, 19.9, 13.7, 12.6; ESI-HRMS m/z (M+Na)' for $C_{35}H_{54}N_2O_{10}$ calc. 685.3671. Found=685.3680.

Synthesis of dimer oxime acetate 36

The desired compound was prepared in a similar manner to propargyl oxime 34 as described above, substituting acetyl chloride for propargyl bromide. Gradient elution on silica gel (10 to 80% ethyl acetate in hexanes) afforded the desired product as a colorless amorphous solid: yield (8.5 mg, 99%); $^1$H NMR (300 MHz, CDCl$_3$) δ 5.67 (d, J=6.88 Hz, 1H), 5.43 (s, 1H), 5.37 (s, 1H), 4.59-4.52 (m, 1H), 2.92-2.81 (m, 2H), 2.76 (dd, J=14.02, 9.66 Hz, 1H), 2.54 (dd, J=14.02, 2.72 Hz, 1H), 2.36-2.26 (m, 2H), 2.16 (s, 3H), 2.06-1.95 (m, 3H), 1.87 (ddd, J=10.22, 6.74, 3.38 Hz, 1H), 1.84-1.81 (m, 1H), 1.81-1.761 (m, 1H), 1.76-1.70 (m, J=13.46, 3.60, 3.60, 3.47 Hz, 1H), 1.68-1.62 (m, 2H), 1.53 (dt, J=13.63, 4.46 Hz, 1H), 1.49-1.43 (m, 1H), 1.43-1.35 (m, 7H), 1.35-1.29 (m, 3H), 1.29-1.18 (m, 3H), 1.00-0.95 (m, 6H), 0.94 (d, J=7.14 Hz, 6H), 0.81 (d, J=7.64 Hz, 3H); $^{13}$C NMR (100 MHz, CDCl$_3$) δ 168.5, 168.04, 103.4, 102.4, 90.4, 88.3, 81.0, 80.7, 73.9, 70.4, 52.7, 51.1, 44.8, 43.2, 37.5, 36.6, 36.6, 34.5, 34.1, 30.4, 30.3, 30.0, 25.7, 25.0, 24.6, 24.6, 20.3, 19.9, 19.8, 13.7, 12.6; ESI-HRMS m/z (M+H)$^+$ for $C_{34}H_{52}NO_{10}$ calc. 634.3586. Found=634.3564.

Synthesis of dimer oxime dimethyl phosphate 37

To a 1 dram vial were added dimer oxime 28 (7.0 mg, 0.01 mmol, 1.0 eq) and dichloromethane (CH$_2$Cl$_2$, 1 mL), followed by triethylamine (Et$_3$N, 3 μL, 0.02 mmol, 2.0 eq) and dimethyl chlorophosphate (3 μL, 0.02 mmol, 2.0 eq). The reaction mixture was stirred overnight at rt. Upon completion the reaction mixture is further diluted with DCM and washed with sat. aq. NH$_4$Cl and brine. The organic layer was extracted, dried over Na$_2$SO$_4$, filtered, and the solvent was removed under reduced pressure. The residue was purified directly on silica gel. Gradient elution (10 to 100% ethyl acetate in hexanes) afforded the desired product as a colorless amorphous solid: yield (2.8 mg, 37%); $^1$H NMR (300 MHz, CDCl$_3$) δ 5.72 (d, J=6.88 Hz, 1H), 5.40 (s, 1H), 5.38 (s, 1H), 4.52 (ddd, J=9.39, 6.02, 3.41 Hz, 1H), 3.96-3.84 (m, 6H), 2.97-2.89 (m, J=15.28, 7.83, 7.58 Hz, 1H), 2.89-2.83 (m, 1H), 2.68 (dd, J=14.08, 9.47 Hz, 1H), 2.59 (dd, J=14.15, 3.35 Hz, 1H), 2.39-2.24 (m, 2H), 2.06-1.97 (m, 3H), 1.92-

1.83 (m, 2H), 1.83-1.79 (m, 1H), 1.79-1.71 (m, 2H), 1.71-1.62 (m, 10H), 1.56 (ddd, J=14.04, 4.82, 4.71 Hz, 1H), 1.51-1.42 (m, 1H), 1.40 (s, 4H), 1.36 (s, 4H), 1.35-1.30 (m, 2H), 1.30-1.21 (m, 5H), 0.97 (dd, J=5.97, 3.88 Hz, 8H), 0.93 (d, J=7.52 Hz, 4H), 0.85 (d, J=7.58 Hz, 3H); $^{13}$C NMR (100 MHz, CDCl$_3$) δ 168.5, 168.4, 103.2, 102.3, 90.4, 88.3, 81.0, 80.6, 73.44, 70.0, 64.6, 64.6, 54.8, 54.2, 52.7, 51.1, 44.7, 43.2, 37.5, 37.3, 36.7, 36.6, 34.6, 34.2, 30.2, 30.0, 29.7, 26.1, 25.7, 25.0, 24.8, 24.7, 20.3, 19.8, 13.5, 12.6; ESI-HRMS m/z (M+H)$^+$ for C$_{34}$H$_{55}$NO$_{12}$P calc. 700.3456. Found=700.3487.

Synthesis of dimer oxime diethyl phosphate 38

The desired compound was prepared in a similar manner to 2C-dimer-oxime-diethyl phosphate 37 as described above, substituting diethyl chlorophosphate for dimethyl chlorophosphate. Gradient elution on silica gel (10 to 100% ethyl acetate in hexanes) afforded the desired product as a colorless amorphous solid: yield (5.4 mg, 63%); $^1$H NMR (300 MHz, CDCl$_3$) δ 5.70 (d, J=6.92 Hz, 1H), 5.39 (s, 1H), 5.37 (s, 1H), 4.52 (ddd, J=9.15, 5.83, 3.44 Hz, 1H), 4.35-4.17 (m, 4H), 2.99-2.80 (m, 2H), 2.75-2.64 (m, J=14.13, 9.04 Hz, 1H), 2.57 (dt, J=14.18, 3.44 Hz, 1H), 2.41-2.24 (m, 2H), 2.06-1.95 (m, 3H), 1.93-1.83 (m, 2H), 1.83-1.76 (m, 2H), 1.75-1.63 (m, 5H), 1.61-1.50 (m, 1H), 1.50-1.41 (m, 1H), 1.41-1.33 (m, 14H), 1.33-1.20 (m, 5H), 1.01-0.95 (m, 7H), 0.93 (d, J=7.49 Hz, 4H), 0.85 (d, J=7.58 Hz, 3H); $^{13}$C NMR (100 MHz, CDCl$_3$) δ 168.6, 168.4, 103.3, 102.3, 90.4, 88.3, 81.1, 80.6, 73.44, 70.0, 65.1, 65.0, 64.6, 64.6, 52.7, 51.1, 44.7, 43.2, 37.5, 37.3, 36.7, 36.6, 34.6, 34.2, 30.2, 30.0, 29.7, 26.1, 25.7, 25.0, 24.8, 24.7, 20.3, 19.8, 16.2, 13.5, 12.6; ESI-HRMS m/z (M+Na)$^+$ for C$_{36}$H$_{58}$NNaO$_{12}$P calc. 750.3589. Found=750.3618.

TABLE 3

Relevant $^1$H NMR chemical shifts and coupling constants

| Cmpd Info | Structure | C5 δ | C5' δ | C10 δ | $J_{C10}$ | C10' δ | $J_{C10}'$ |
|---|---|---|---|---|---|---|---|
| 20 | 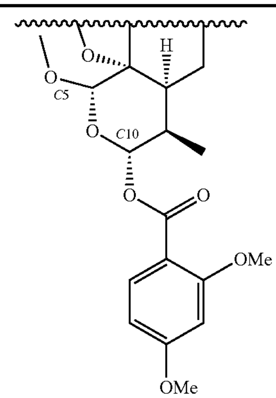 | 5.47 | — | 5.96 | 9.8 Hz | — | — |
| 21 | 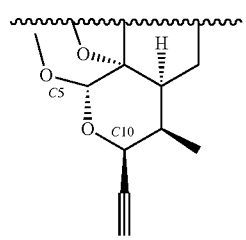 | 5.56 | — | 4.73 | 5.7 Hz | — | — |
| 22 | 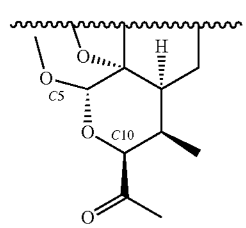 | 5.65 | — | 4.75 | 6.8 Hz | — | — |
| 24 | 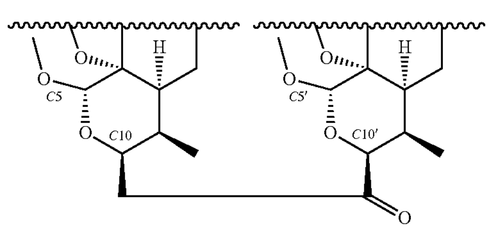 | 5.57 | 5.30 | 4.57 | 6.3 Hz | 4.84 | 9.5 Hz, 6.2 Hz, 3.8 Hz |

TABLE 3-continued

Relevant $^1$H NMR chemical shifts and coupling constants

| Cmpd Info | Structure | C5 δ | C5' δ | C10 δ | $J_{C10}$ | C10' δ | $J_{C10'}$ |
|---|---|---|---|---|---|---|---|
| 28 | (structure with N—OH) | 5.39 | 5.37 | 5.68 | 6.9 Hz | 4.53 | 9.1 Hz<br>5.9 Hz<br>3.3 Hz |
| Less polar-Z-29 | (structure with N—OMe) | 5.41 | 5.35 | 5.56 | 6.9 Hz | 4.55 | 8.9 Hz<br>5.9 Hz<br>4.4 Hz |
| More polar-E-29 | (structure with MeO—N) | 5.62 | 5.35 | 5.09 | 6.4 Hz | 4.58 | buried |
| 30 | (structure with N—O-allyl) | 5.40 | 5.36 | 5.63 | 6.9 Hz | 4.56 | buried |

Example 4

The following 2-carbon-bridged trioxane dimers also can be prepared by the presently disclosed methods:

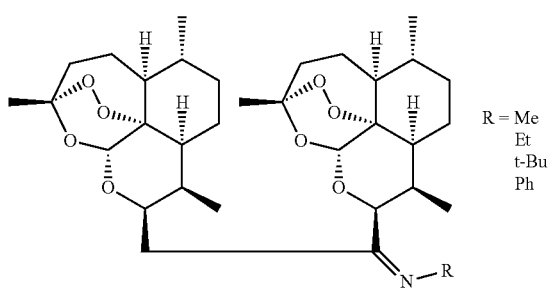

R = Me
Et
t-Bu
Ph

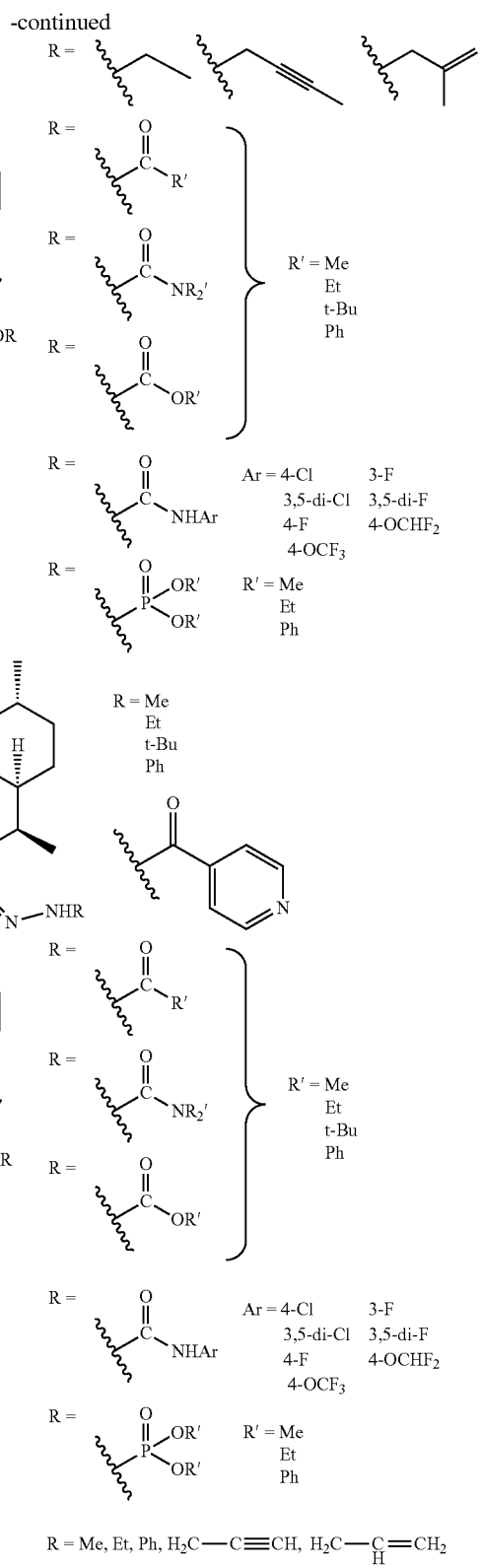

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

W.H.O. Malaria fact sheet No. 94. http://www.who.int/mediacentre/factsheets/fs094/en/index.html (accessed Aug. 13, 2012).

Frey, C.; Traore, C.; De Allegri, M.; Kouyate, B.; Muller, O., Compliance of young children with ITN protection in rural Burkina Faso. *Malaria J.* 2006, 5 (70), 1-8.

The RTS, S.; Clincal; Trials; Partnership, First Results of Phase 3 Trial of RTS,S/AS01 Malaria Vaccine in African Children. *N Engl J Med* 2011, 365 (20), 1863-1875.

Schlitzer, M., Malaria chemotherapeutics. Part I: History of antimalarial drug development, currently used therapeutics, and drugs in clinical development. *Chem. Med. Chem.* 2007, 2, 944-986.

Miller, L. H.; Su, X.-z., Artemisinin: Discovery from the Chinese Herbal Garde. *Cell* 2011, 146, 855-858.

He, R.; Mott, B. T.; Rosenthal, A. S.; Genna, D. T.; Posner, G. H.; Arav-Boger, R., An Artemisinin-Derived Dimer Has Highly Potent Anti-Cytomegalovirus (CMV) and Anti-Cancer Activities. *PLoS One* 2011, 6 (8), e24334.

Kyle, D. E.; Teja-Isavadharm, P.; Li, Q.; Leo, K., Pharmacokinetics and pharmacodynamics of qinghaosu derivatives: how do they impact on the choice of drug and the dosage regimens? *Med. Trop.* 1998, 58, 38-44.

G.S.K. Coartem®. http://www.coartem.com/coartem-riamet.htm (accessed Sep. 6, 2012).

M.M.V. Pyramax® (pyronaridine-artesunate). http://www.mmv.org/research-development/project-portfolio/pyramax % C2% AE-pyronaridine-artesunate (accessed Sep. 6, 2012).

Haynes, R. K.; Fugmann, B.; Stetter, J.; Rieckmann, K.; Hans-Dietrich, H.; Chan, H.-W.; Cheung, M.-K.; Lam, W.-L.; Wong, H.-N.; Croft, S. L.; Vivas, L.; Rattray, L.; Stewart, L.; Peters, W.; Robinson, B. L.; Edstein, M. D.; Kotecka, B.; Kyle, D. E.; Beckermann, B.; Gerisch, M.; Radtke, M.; Schmuck, G.; Steinke, W.; Wollborn, U.; Schmeer, K.; Romer, A., Artemisone—a highly active antimalarial drug of the artemisinin class. *Angew. Chem. Int. Ed.* 2006, 45, 2082-2088.

Araujo, N. C. P.; Barton, V.; Jones, M.; Stocks, P. A.; Ward, S. A.; Davies, J.; Bray, P. G.; Shone, A. E.; Cristiano, M. L. S.; O'Neill, P. M., Semi-synthetic and synthetic 1,2,4-trioxaquines and 1,2,4-trioxolaquines: synthesis, preliminary SAR and comparison with acridine endoperoxide conjugates. *Bioorg. Med. Chem. Lett.* 2009, 19, 2038-2043.

Pacorel, B.; Leung, S. C.; Stachulski, A. V.; Davies, J.; Vivas, L.; Lander, H.; Ward, S. A.; Kaiser, M.; Brun, R.; O'Neill, P. M., Modular Synthesis and in Vitro and in Vivo Antimalarial Assessment of C-10 Pyrrole Mannich Base Derivatives of Artemisinin. *J. Med. Chem.* 2010, 53, 633-640.

Chadwick, J.; Jones, M.; Mercer, A. E.; Stocks, P. A.; Ward, S. A.; Park, B. K.; O'Neill, P. M., Design, synthesis and antimalarial/anticancer evaluation of spermidine linked artemisinin conjugates designed to exploit polyamine transporters in *Plasmodium falciparum* and HL-60 cancer cell lines. *Bioorg. Med. Chem.* 2010, 18, 2586-2597.

Begue, J. P.; Bonnet-Delpon, D., Fluoroartemisinins: metabolically more stable antimalarial artemisinin derivatives. *Chem. Med. Chem.* 2007, 2, 608-624.

Singh, C.; Hassam, M.; Verma, V. P.; Singh, A. S.; Naikade, N. K.; Puri, S. K.; Maulik, P. R.; Kant, R., Bile Acid-Based 1,2,4-Trioxanes: Synthesis and Antimalarial Assessment. *J. Med. Chem.* 2012, 55, 10662-10673.

Dong, Y.; Chollet, J.; Matile, H.; Charman, S. A.; Chiu, F. C. K.; Charman, W. N.; Scorneaux, B.; Urwyler, H.; Tomas, J. S.; Schuerer, C.; Snyder, C.; Dorn, A.; Wang, X.; Karle, J. M.; Tang, Y.; Wittlin, S.; Brun, R.; Vennerstrom, J. L., Spiro and Dispiro-1,2,4-trioxolanes as Antimalarial Peroxides: Charting a Workable Structure-Activity Relationship Using Simple Prototypes. *J. Med. Chem.* 2005, 48, 4953-4961.

Charman, S. A.; Arbe-Barnes, S.; Bathurst, I. C.; Brun, R.; Campbell, M.; Charman, W. N.; Chiu, F. C. K.; Chollet, J.; Craft, J. C.; Creek, D. J.; Dong, Y.; Matile, H.; Maurer, M.; Morizzi, J.; Nguyen, T.; Papastogiannidis, P.; Scheurer, C.; Shackleford, D. M.; K., S.; Stingelin, L.; Tang, Y.; Urwyler, H.; Wang, X.; White, K. L.; Wittlin, S.; Zhou, L.; Vennerstrom, J. L., Synthetic ozonide drug candidate OZ439 offers new hope for a single-dose cure of uncomplicated malaria. *Proc. Nat. Acad. Sci.* 2011, 108, 4400-4405.

Slack, R. D.; Jacobine, A. M.; Posner, G. H., Antimalarial peroxides: advances in drug discovery and design. *Med. Chem. Commun.* 2012, 3 (281-297).

Moon, D. K.; Tripathi, J.; Sullivan, D.; Siegler, M. A.; Parkin, S.; Posner, G. H., A single, low, oral dose of a 5-carbon-linked trioxane dimer orthoester plus mefloquine cures malaria-infected mice. *Bioorg. Med. Chem. Lett.* 2011, 21, 2773-2775.

Paik, I.-H.; Xie, S.; Shapiro, T. A.; Labonte, T.; Narducci-Sarjeant, A. A.; Baege, A. C.; Posner, G. H., Second Generation, Orally Active, Antimalarial, Artemisinin-Derived Trioxane Dimers with High Stability, Efficacy, and Anticancer Activity. *J. Med. Chem.* 2006, 49, 2731-2734.

Rosenthal, A. S.; Chen, X.; Liu, J. O.; West, D. C.; Hergenrother, P. J.; Shapiro, T. A.; Posner, G. H., Malaria-Infected Mice Are Cured by a Single Oral Dose of New Dimeric Trioxane Sulfones Which Are Also Selectively and Powerfully Cytotoxic to Cancer Cells. *J. Med. Chem.* 2009, 52, 1198-1203.

Woodard, L. E.; Chang, W.; Chen, X.; Liu, J. O.; Shapiro, T. A.; Posner, G. H., Malaria-Infected Mice Live until at Least Day 30 after a New Monomeric Trioxane Combined with Mefloquine Are Administered Together in a Single Low Oral Dose. *J. Med. Chem.* 2009, 52, 7458-7462.

Posner, G. H.; Murray, C.; O'Dowd, H.; Xie, S.; Shapiro, T. A. Preparation of artemisinin analogs having antimalarial, antiproliferative, and antitumor activities. 2000.

Galal, A. M.; Ahmad, M. S.; El-Feraly, F. S.; McPhail, A. T., Preparation and Characterization of a New Artemisinin-Derived Dimer. *J. Nat. Prod.* 1996, 59, 917-920.

Pu, Y. M.; Ziffer, H., Synthesis and Antimalarial Activities of 12.beta.-Allyldeoxoartemisinin and Its Derivatives. *J. Med. Chem.* 1995, 38, 613-616; (b) Ma, J.; Katz, E.; Kyle, D. E.; Ziffer, H., Syntheses and Antimalarial Activities of 10-Substituted Deoxoartemisinins. *J. Med. Chem.* 2000, 43, 4228-4232.

Jung, M.; Lee, K.; Kendrick, H.; Robinson, B. L.; Croft, S. L., Synthesis, Stability, and Antimalarial Activity of New Hydrolytically Stable and Water-Soluble (+)-Deoxoartelinic Acid. *J. Med. Chem.* 2002, 45, 4940-4944.

Posner, G. H.; Ploypradith, P.; Parker, M. H.; O'Dowd, H.; Woo, S.-H.; Northrop, J.; Krasavin, M.; Dolan, P.; Kensler, T. W.; Xie, S.; Shapiro, T. A., Antimalarial, Antiproliferative, and Antitumor Activities of Artemisinin-Derived, Chemically Robust, Trioxane Dimers. *J. Med. Chem.* 1999, 42, 4275-4280.

Hevia, E.; Chua, J. Z.; Garcia-Alvarez, P.; Kennedy, A. R.; McCall, M. D., Exposing the hidden complexity of stoichiometric and catalytic metathesis reactions by elucidation of Mg—Zn hybrids. *Proc. Nat. Acad. Sci.* 2010, 107, 5294-5299.

Hatano, M.; Suzuki, S.; Ishihara, K., Highly Chemoselective Stoichiometric Alkylation of Ketones with Grignard Reagent Derived Zinc(II) Ate Complexes. *Synlett* 2010, 2, 321-324.

Lepore, S. D.; Mondal, D., Recent advances in heterolytic nucleofugal leaving groups. *Tetrahedron* 2007, 63, 5103-5122.

Corey, E. J.; Bakshi, R. K.; Shibata, S., Highly Enantioselective Borane Reduction of Ketones Catalyzed by Chiral Oxazaborolidines. Mechanism and Synthetic Implications. *J. Am. Chem. Soc.* 1987, 109, 5551-5553.

Musilek, K.; Dolezal, M.; Gunn-Moore, F.; Kuca, K., Design, evaluation and structure-activity relationship studies of the AChE reactivators against organophosphorus pesticides. *Med. Res. Rev.* 2009, 31, 548-575.

Krivogorksy, B.; Grundt, P.; Yolken, R.; Jones-Brando, L., Inhibition of *Toxoplasma gondii* by Indirubin and Tryptanthrin Analogs. *Antimicrob. Agents Chemother.* 2008, 52, 4466-4469.

Gibson, C. L.; Huggan, J. K.; Kennedy, A.; Kiefer, L.; Lee, J. H.; Suckling, C. J.; Clements, C.; Harvey, A. L.; Hunter, W. N.; Tulloch, L. B., Diversity oriented syntheses of fused pyrimidines designed as potential antifolates. *Org. Biomol. Chem.* 2009, 7, 1829-1842.

Huttunen, K. M.; Kumpulainen, H.; Leppanen, J.; Rautio, J.; Jarvinen, T.; Vepsalainen, J., Efficient strategy to prepare water-soluble prodrugs of ketones. *Synlett* 2006, 5, 701-704.

Venhuis, B. J.; Dijkstra, D.; Wustrow, D.; Meltzer, L. T.; Wise, L. D.; Johnson, S. J.; Wikstrom, H. V., Orally Active Oxime Derivatives of the Dopaminergic Prodrug 6-(N,N-Di-n-propylamino)-3,4,5,6,7,8-hexahydro-2H-naphthalen-1-one. Synthesis and Pharmacological Activity. *J. Med. Chem.* 2003, 46, 4136-4140.

Kumpulainen, H.; Mahonen, N.; Laitinen, M.-L.; Jaurakkajarvi, M.; Raunio, H.; Juvonen, R. O.; Vepsalainen, J.; Jarvinen, T.; Rautio, J., Evaluation of Hydroxyimine as Cytochrome P450-Selective Prodrug Structure. *J. Med. Chem.* 2006, 49, 1207-1211.

Prokai, L.; Wu, W.-M.; Somogyi, G.; Bodor, N., Ocular Delivery of the β-Adrenergic Antagonist Alprenolol by Sequential Bioactivation of Its Methoxime Analogue. *J. Med. Chem.* 1995, 38, 2018-2020.

Haynes, R. K.; Chan, H.-W.; Cheung, M.-K.; Lam, W.-L.; Soo, M.-K.; Tsang, H.-W.; Voerste, A.; Williams, I. D., C-10 Ester and Ether Derivatives of Dihydroartemisinin-10-α Artesunate, Preparation of Authentic 10-â Artesunate, and of Other Ester and Ether Derivatives Bearing Potential Aromatic Intercalating Groups at C-10. *Eur. J. Org. Chem.* 2002, 2002, 113-132.

Karplus, M., Contact Electron-Spin Coupling of Nuclear Magnetic Moments. *J. Chem. Phys.* 1959, 30, 11-15.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of Formula (I):

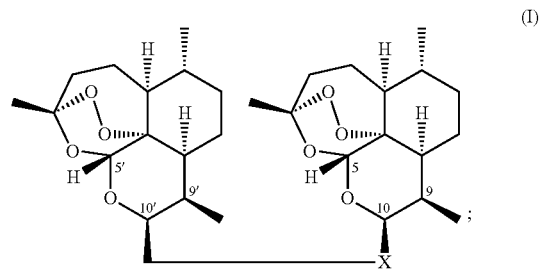

wherein:

X is selected from the group consisting of C(=O); C=NR$_1$; C=NOR$_2$; C=NNHR$_3$; and CH—O—R$_4$;

R$_1$ is selected from the group consisting of substituted or unsubstituted linear or branched alkyl, substituted or unsubstituted cycloalkyl, substituted or unsubstituted cycloheteroalkyl, substituted or unsubstituted aryl, and substituted or unsubstituted heteroaryl;

R$_2$ is selected from the group consisting of H, substituted or unsubstituted linear or branched alkyl, substituted or unsubstituted alkenyl, substituted or unsubstituted alkynyl, —P(=O)(OR$_5$)(OR$_5$), wherein each R$_5$ is independently lower linear or branched alkyl, aryl or heteroaryl, and —C(=O)R$_6$, wherein R$_6$ is substituted or unsubstituted linear or branched alkyl, substituted or unsubstituted cycloalkyl, alkoxyl, aryloxyl, substituted or unsubstituted cycloheteroalkyl, substituted or unsubstituted aryl, substituted or unsubstituted heteroaryl, and NR$_7$R$_8$, wherein R$_7$ and R$_8$ are each independently selected from the group consisting of H, substituted or unsubstituted linear or branched alkyl, substituted or unsubstituted cycloalkyl, substituted or unsubstituted cycloheteroalkyl, substituted or unsubstituted aryl, substituted or unsubstituted heteroaryl;

R$_3$ is selected from the group consisting of substituted or unsubstituted linear or branched alkyl, substituted or unsubstituted cycloalkyl, substituted or unsubstituted cycloheteroalkyl, substituted or unsubstituted aryl, substituted or unsubstituted heteroaryl, and —(C=O)R$_9$, wherein R$_9$ is selected from the group consisting of substituted or unsubstituted linear or branched alkyl, substituted or unsubstituted cycloalkyl, substituted or unsubstituted cycloheteroalkyl, substituted or unsubstituted aryl, substituted or unsubstituted heteroaryl;

R$_4$ is selected from the group consisting of H, substituted or unsubstituted linear or branched alkyl, substituted or unsubstituted alkenyl, substituted or unsubstituted alkynyl, substituted or unsubstituted aryl, substituted or unsubstituted heteroaryl, —P(=O)(OR$_5$)(OR$_5$), wherein each R$_5$ is independently lower linear or branched alkyl, aryl or heteroaryl, and —C(=O)R$_{10}$, wherein R$_{10}$ is substituted or unsubstituted linear or branched alkyl, substituted or unsubstituted cycloalkyl, alkoxyl, aryloxyl, substituted or unsubstituted cycloheteroalkyl, substituted or unsubstituted aryl, substituted or unsubstituted heteroaryl, and NR$_{11}$R$_{12}$, wherein R$_{11}$ and R$_{12}$ are each independently selected from the group consisting of H, substituted or unsubstituted linear or branched alkyl, substituted or unsubstituted cycloalkyl, substituted or unsubstituted cycloheteroalkyl, substituted or unsubstituted aryl, substituted or unsubstituted heteroaryl;

or an enantiomer, diastereomer, racemate or pharmaceutically acceptable salt, prodrug, or solvate thereof.

2. The compound of claim 1, wherein X is C(=O) and the compound of Formula (I) is:

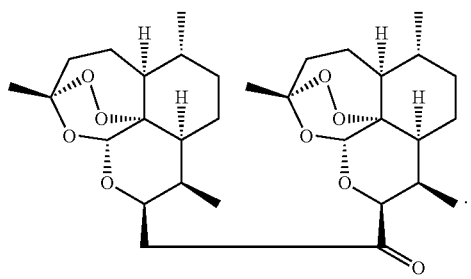

24

3. The compound of claim 1, wherein X is C=NR₁ and the compound of Formula (I) is selected from the group consisting of:

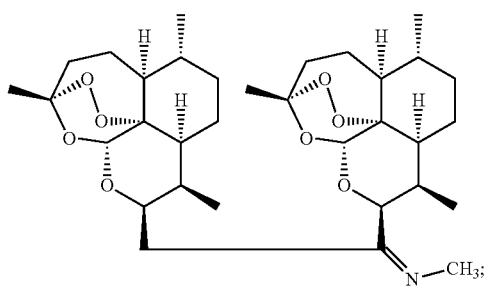

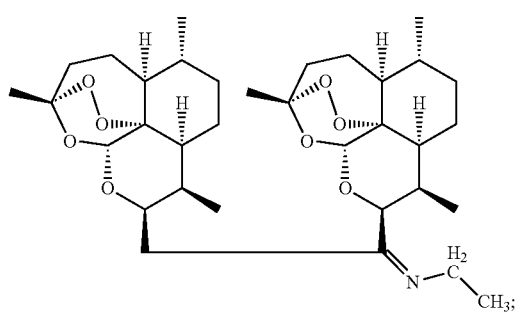

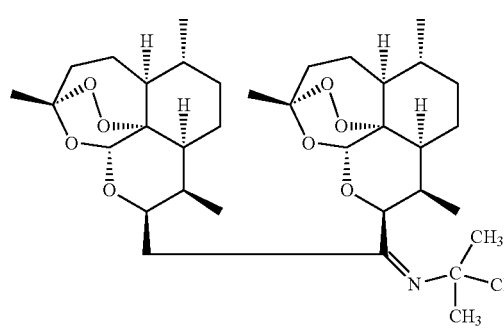

-continued

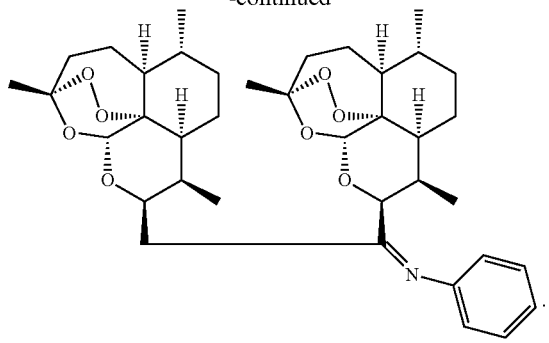

4. The compound of claim 1, wherein X is C=NOR₂ and the compound of Formula (I) is selected from the group consisting of:

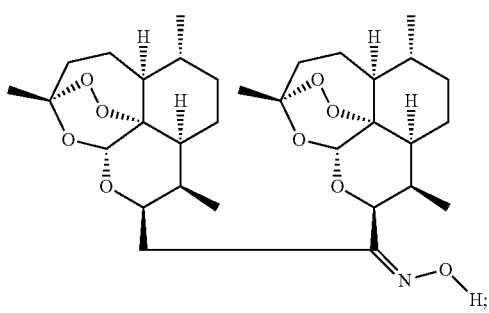

28

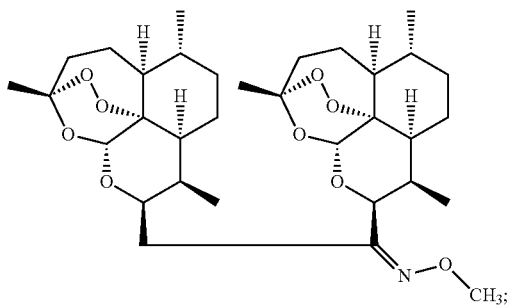

29

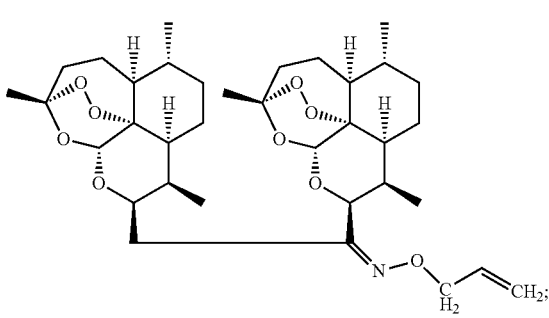

30

31
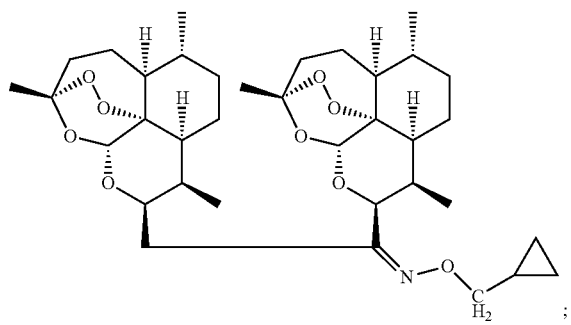
32
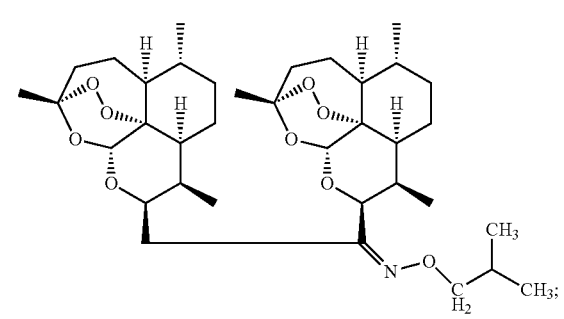
33
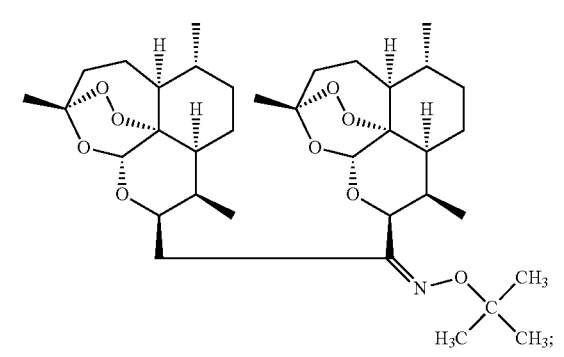
34
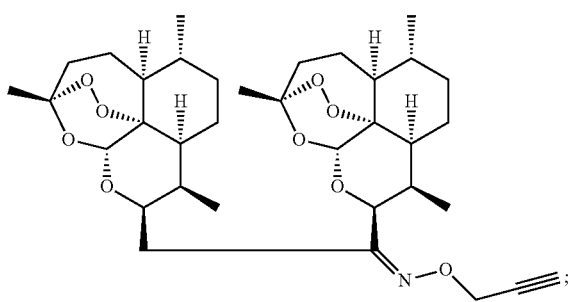
35
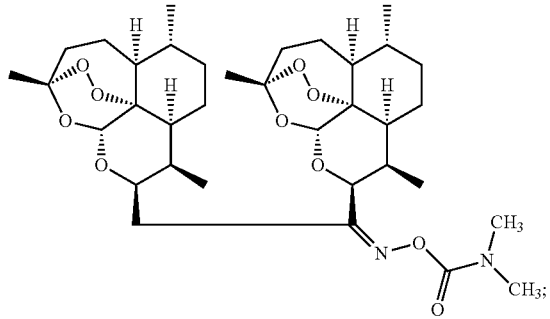
36
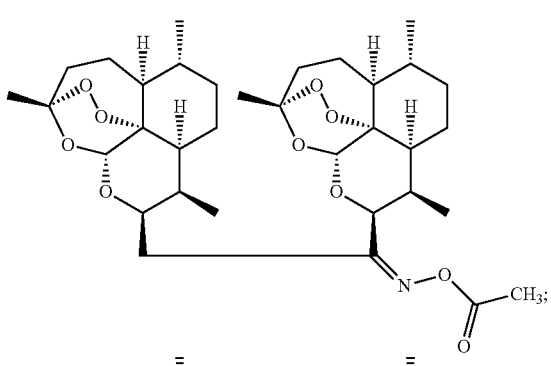
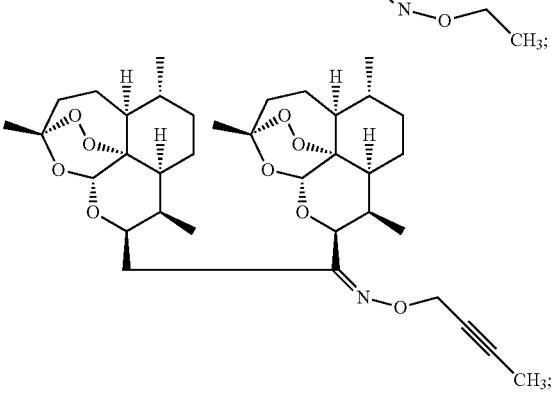
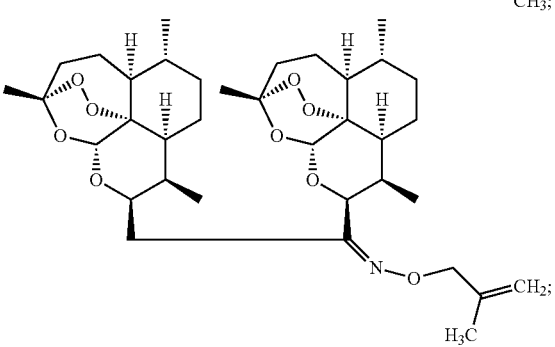

81 -continued
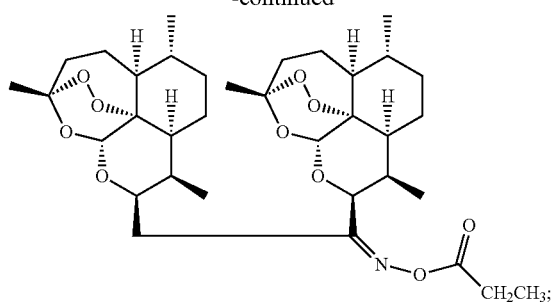
82 -continued
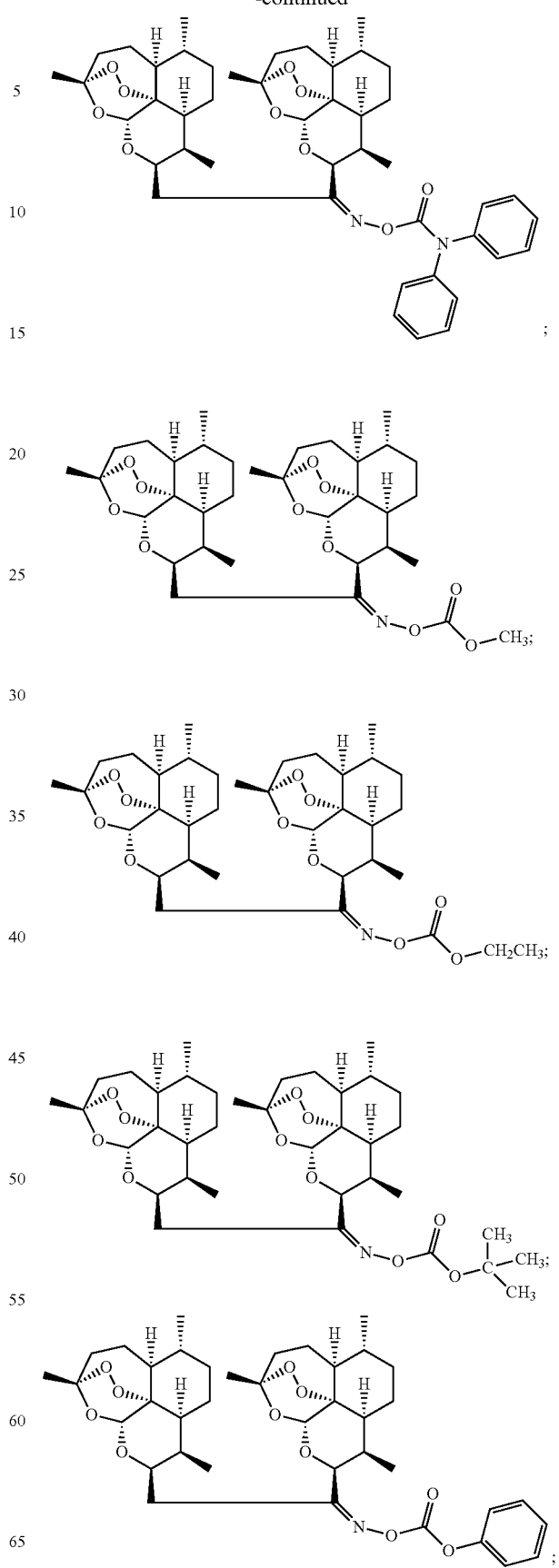

83
-continued
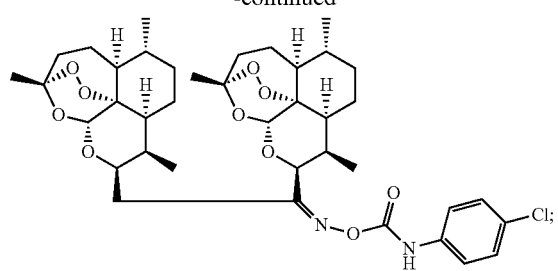
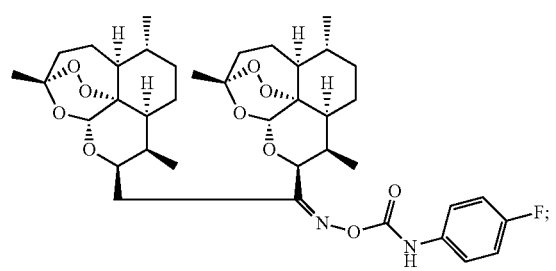
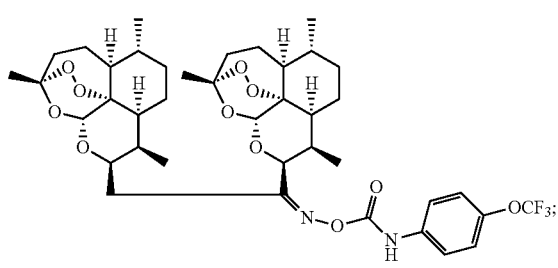
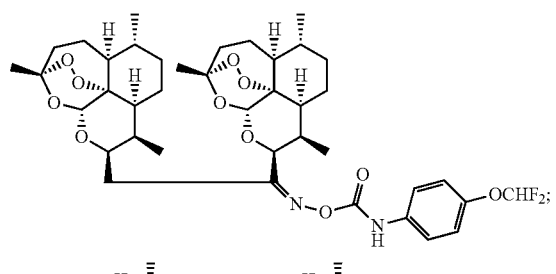
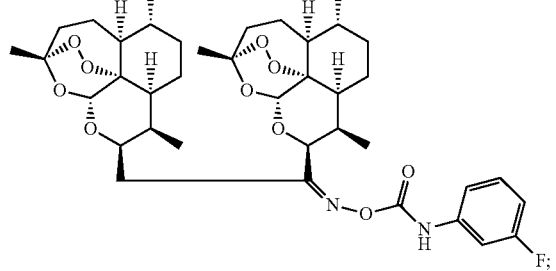
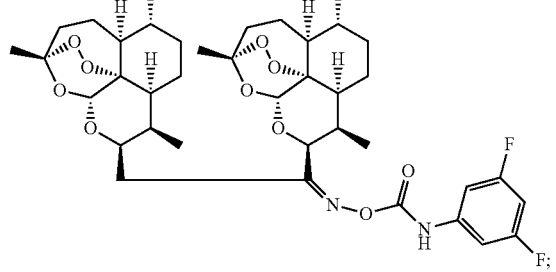
84
-continued
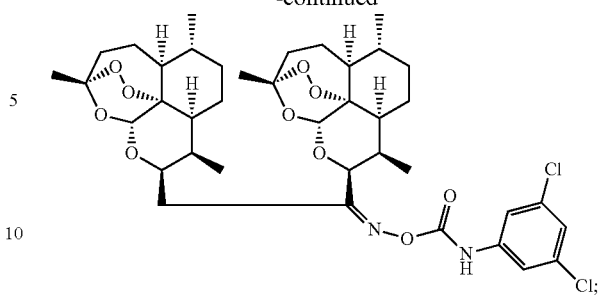
37
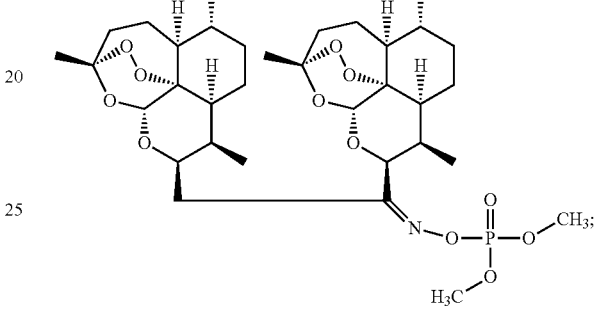
38
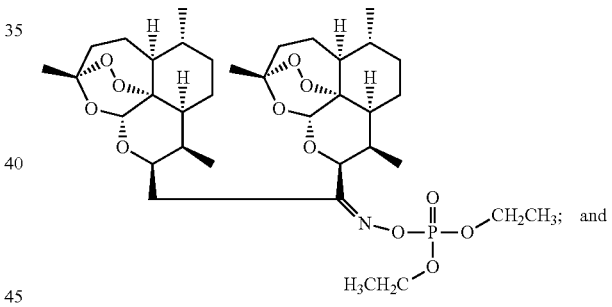
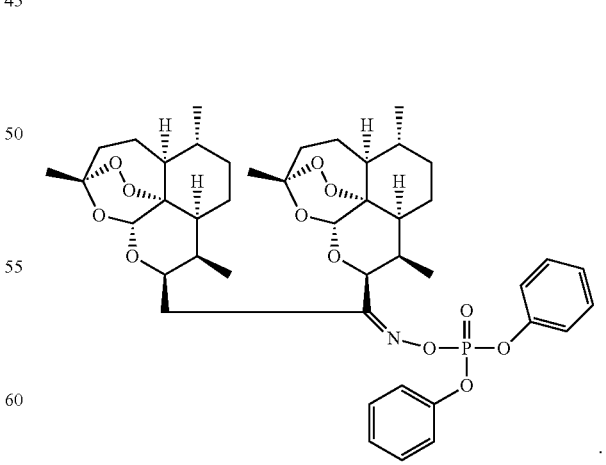
5. The compound of claim 1, wherein X is C=NNHR$_3$ and the compound of Formula (I) is selected from the group consisting of:

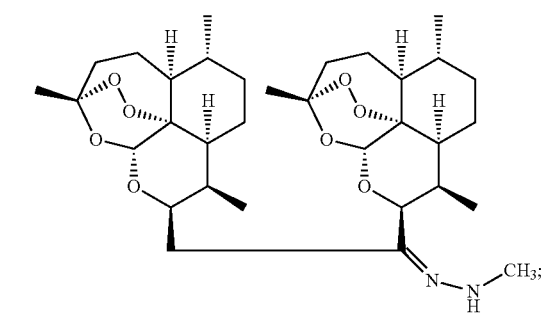
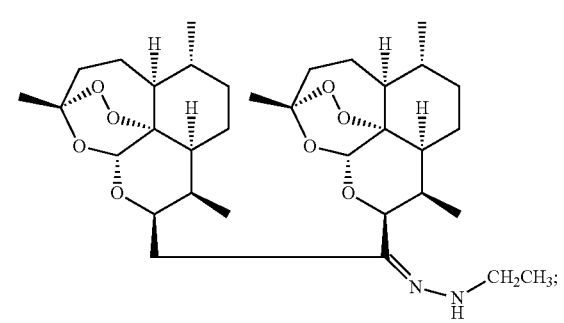
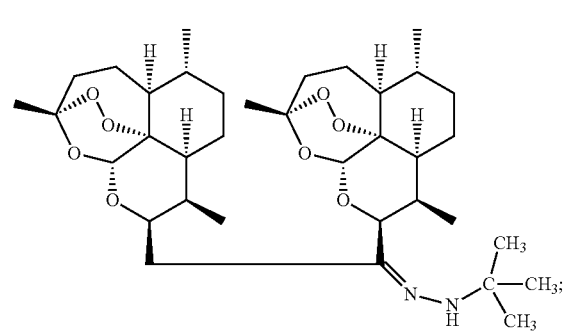
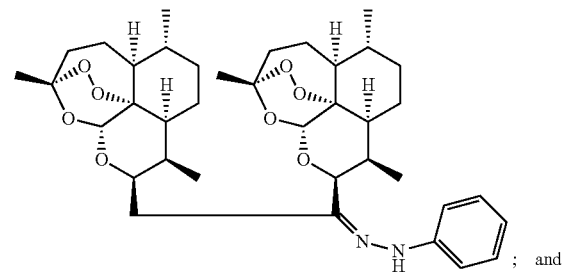
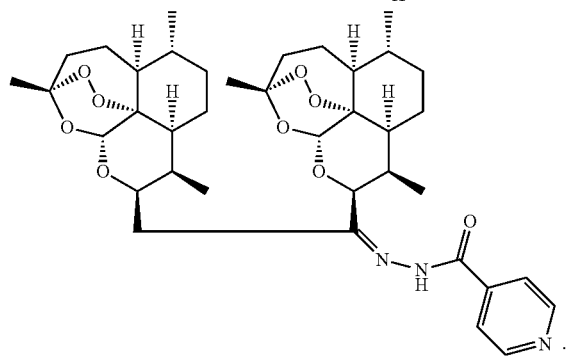
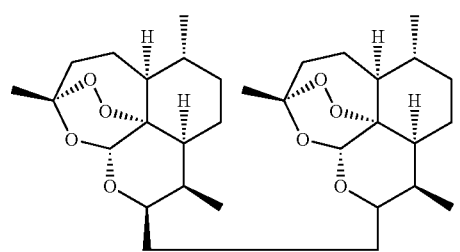
R-25
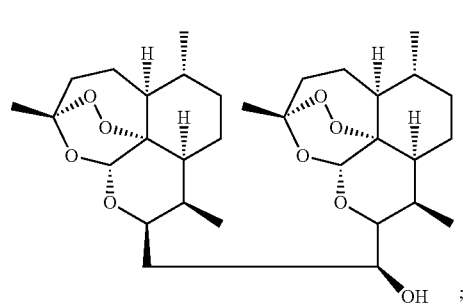
S-26
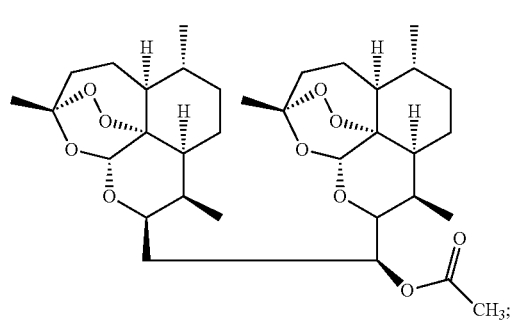
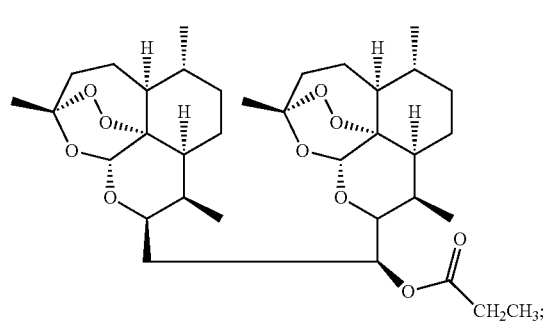
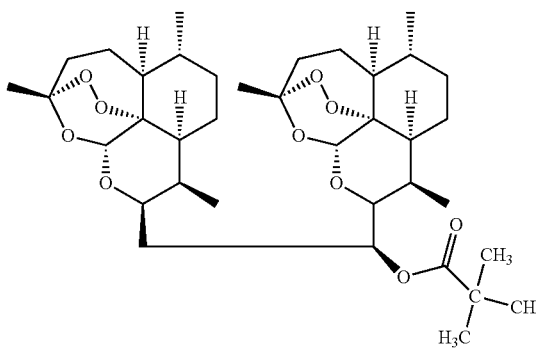
6. The compound of claim 1, wherein X is CH—O—R$_4$ and the compound of Formula (I) is selected from the group consisting of:

87
-continued
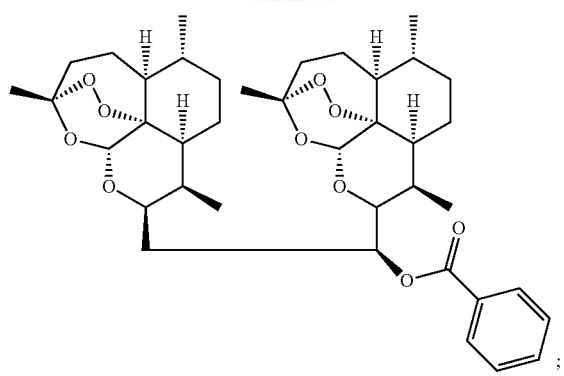
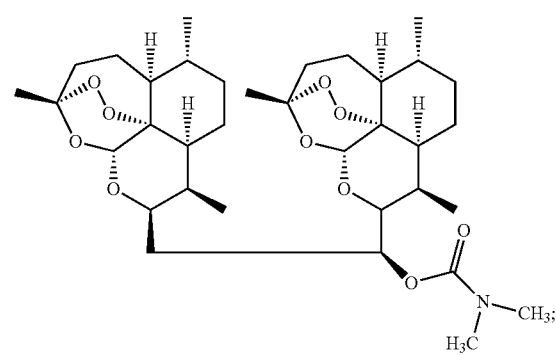
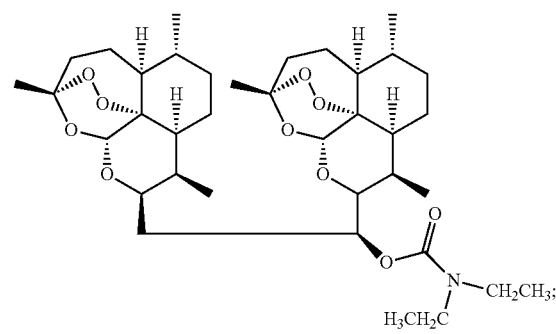
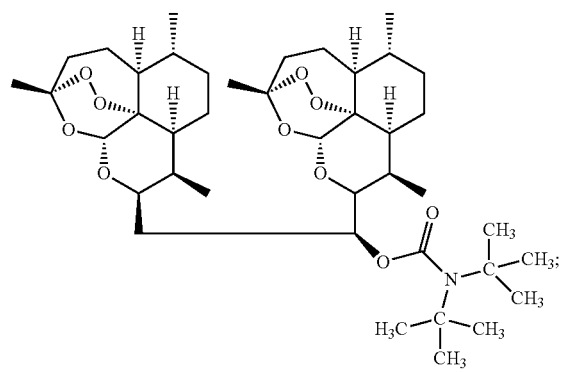
88
-continued
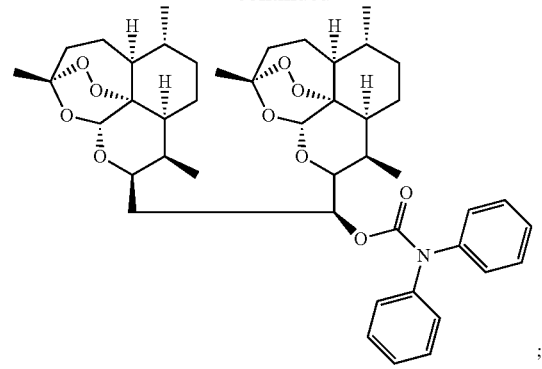
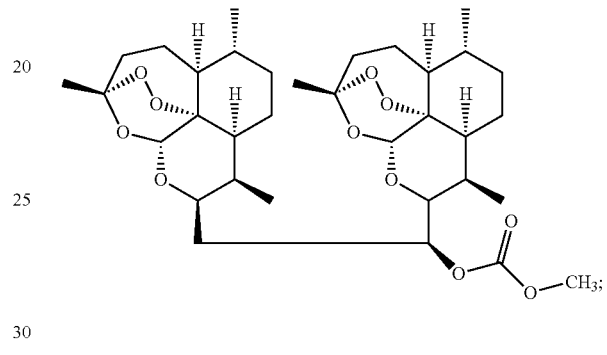
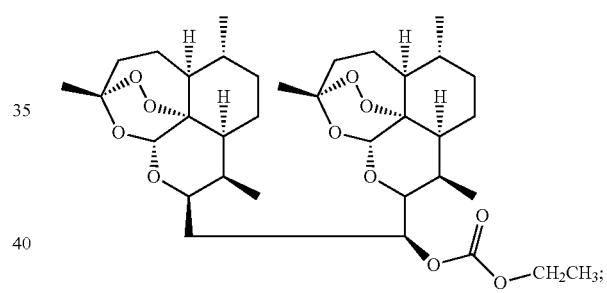
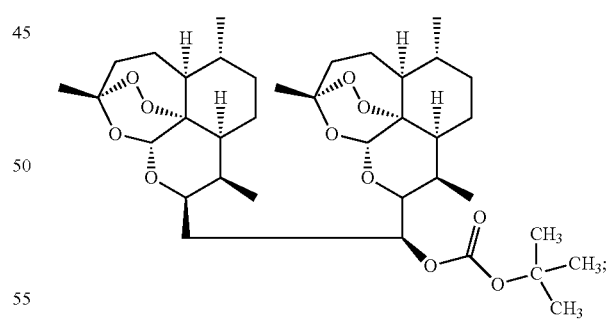
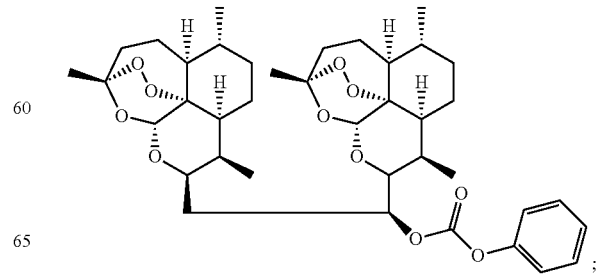

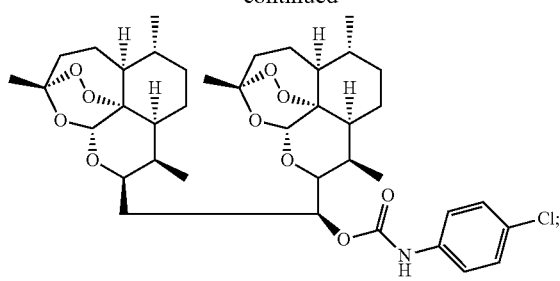
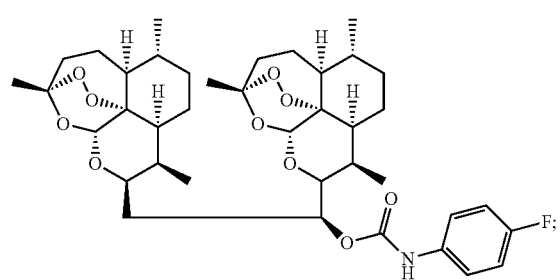
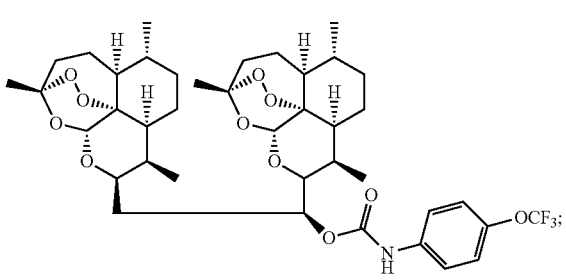
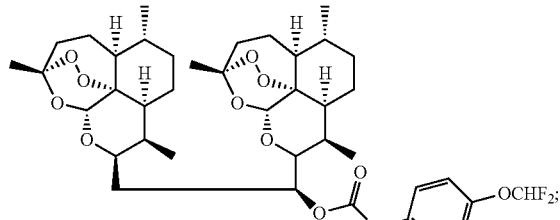
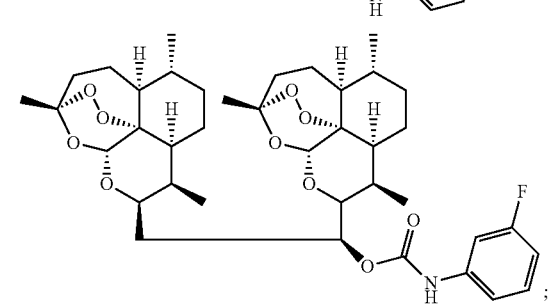
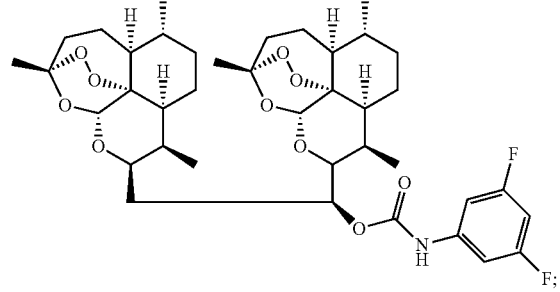
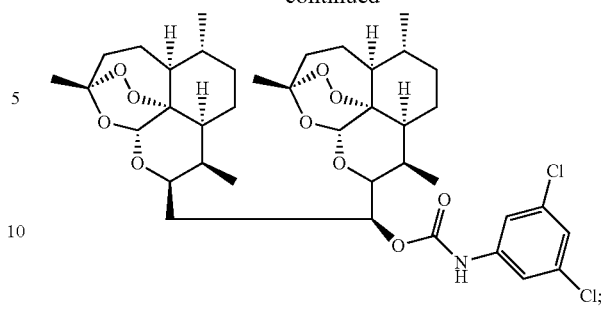
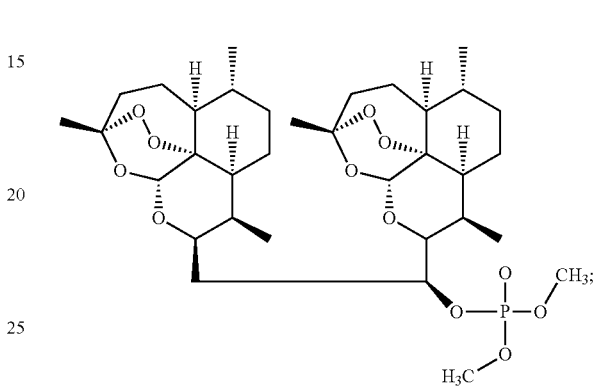
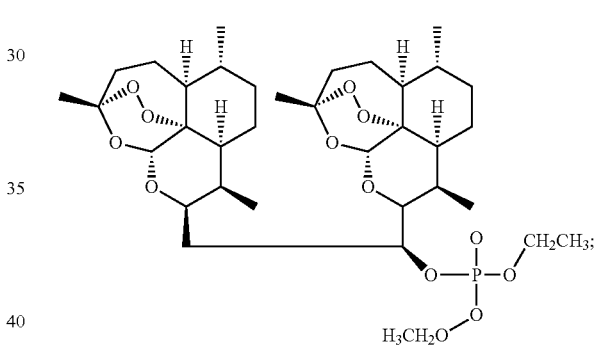
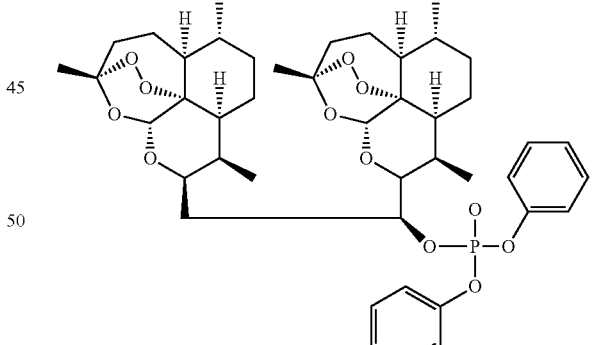
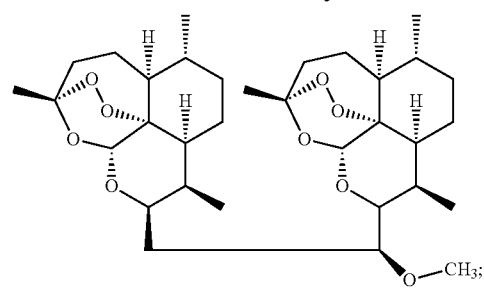

-continued

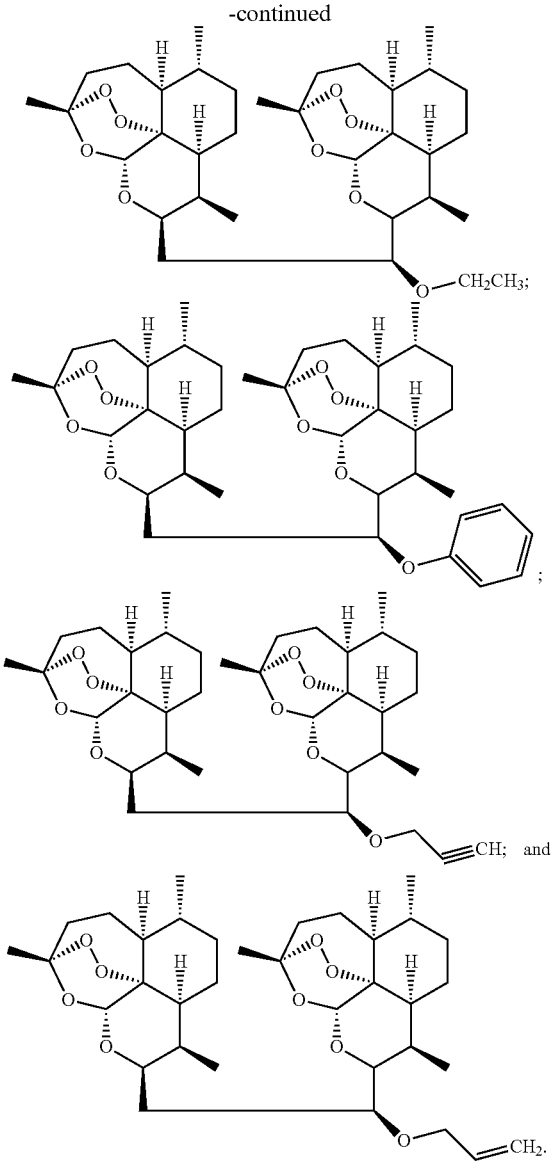

7. A pharmaceutical composition comprising a compound of claim 1.

8. A method for preventing, controlling or treating an infectious disease in a subject in need of such treatment, the method comprising administering to the subject a therapeutically-effective amount of a compound of Formula (I) according to claim 1, or an enantiomer, diastereomer, racemate or pharmaceutically acceptable salt, prodrug, or solvate thereof.

9. The method of claim 8, wherein the infectious disease comprises a parasitic disease selected from the group consisting of a plasmodia parasite infection, a *T. gondii* infection, a trypanosome parasite infection, and a *Cryptosporidium* parasite infection.

10. The method of claim 8, further comprising administering to the subject a quinoline anti-malarial drug, an antifolate, and/or lumefantrine concurrently or sequentially with the compound of Formula (I).

11. The method of claim 10, wherein the quinoline anti-malarial drug is selected from the group consisting of chloroquine, quinine, mefloquine, and primaquine.

12. A method for treating a psychiatric disorder associated with a *toxoplasma* infection in a subject in need of treatment thereof, the method comprising administering to the subject a therapeutically-effective amount of a compound of Formula (I) according to claim 1, or an enantiomer, diastereomer, racemate or pharmaceutically acceptable salt, prodrug, or solvate thereof.

13. The method of claim 12, wherein the psychiatric disorder is schizophrenia.

14. The method of claim 12, further comprising administering to the subject one or more antipsychotic drugs selected from the group consisting of chlorpromazine, haloperidol, fluphenazine, thiothixene, trifluoperazine, perphenazine, and thioridazine, clozapine, risperidone, olanzapine, quetiapine, ziprasidone, and aripiprazole concurrently or sequentially with the compound of Formula (I).

* * * * *

UNITED STATES PATENT AND TRADEMARK OFFICE
CERTIFICATE OF CORRECTION

PATENT NO. : 9,487,538 B2
APPLICATION NO. : 14/761699
DATED : November 8, 2016
INVENTOR(S) : Gary H. Posner and Bryan T. Mott Page 1 of 1

It is certified that error appears in the above-identified patent and that said Letters Patent is hereby corrected as shown below:

In the Specification

Column 1, Line 15, Replace the second paragraph as follows:
STATEMENT OF GOVERNMENTAL INTEREST
This invention was made with government support under AI034885, awarded by the National Institutes of Health. The government has certain rights in the invention.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*